US010413290B1

(12) United States Patent
Robert, III

(10) Patent No.: US 10,413,290 B1
(45) Date of Patent: Sep. 17, 2019

(54) COMBINED NEEDLE HOLDER SCISSORS

(71) Applicant: Kearny Quinn Robert, III, Metairie, LA (US)

(72) Inventor: Kearny Quinn Robert, III, Metairie, LA (US)

( * ) Notice: Subject to any disclaimer, the term of this patent is extended or adjusted under 35 U.S.C. 154(b) by 366 days.

(21) Appl. No.: 14/586,284

(22) Filed: Dec. 30, 2014

Related U.S. Application Data

(60) Provisional application No. 61/922,004, filed on Dec. 30, 2013.

(51) Int. Cl.
*A61B 17/062* (2006.01)
*A61B 17/04* (2006.01)
*A61B 17/285* (2006.01)
*A61B 17/28* (2006.01)

(52) U.S. Cl.
CPC ........ *A61B 17/062* (2013.01); *A61B 17/0467* (2013.01); *A61B 17/282* (2013.01); *A61B 17/285* (2013.01); *A61B 17/2833* (2013.01); *A61B 17/2841* (2013.01)

(58) Field of Classification Search
CPC . A61B 17/282; A61B 17/2833; A61B 17/285; A61B 17/062; A61B 17/0467; A61B 17/2841
See application file for complete search history.

(56) References Cited

U.S. PATENT DOCUMENTS

| 1,918,700 | A | * | 7/1933 | Harris | A61B 17/3201 30/134 |
| 2,679,249 | A | * | 5/1954 | Weihmann | A61B 17/32 30/124 |
| 3,175,556 | A | * | 3/1965 | Wood | A61B 17/122 30/124 |
| 3,443,313 | A | * | 5/1969 | Profy | A61B 17/0467 30/134 |
| 3,651,811 | A | * | 3/1972 | Hildebrandt | A61B 17/3201 606/51 |
| 4,423,729 | A | | 1/1984 | Gray | |
| 4,452,246 | A | * | 6/1984 | Bader | A61B 17/0467 30/131 |

(Continued)

FOREIGN PATENT DOCUMENTS

EP 2444007 4/2012

*Primary Examiner* — Hwei-Siu C Payer
(74) *Attorney, Agent, or Firm* — Garvey, Smith & Nehrbass, Patent Attorneys, L.L.C.; Seth M. Nehrbass; Mackenzie D. Rodriguez

(57) ABSTRACT

The invention involves an instrument with a set of grasping jaws such as found on surgical needle drivers, hemostats, grasping forceps, and clamps. In addition to the grasping jaws for holding and grasping material, it includes a set of cutting shears or scissors that operate in the same main working jaws. It functions as a standard needle holder with grasping and locking functions with the use of two main actuating limbs. When desired, the instrument is easily converted by a simple action of the operator from a grasping device into a cutting device and then can be used in a familiar fashion, such as employed for scissors, to repeatedly cut sutures or material. Again, with a simple action by the operator, the instrument can be converted back to a grasping device. Both grasping and cutting functions take place in the same location on the device.

11 Claims, 46 Drawing Sheets

(56) References Cited

U.S. PATENT DOCUMENTS

| | | | | |
|---|---|---|---|---|
| 4,478,221 | A | * | 10/1984 | Heiss ................... A61B 17/04 606/145 |
| 4,527,331 | A | | 7/1985 | Lasner et al. |
| 4,600,007 | A | * | 7/1986 | Lahodny ............... A61B 17/04 30/131 |
| 4,949,717 | A | * | 8/1990 | Shaw ................ A61B 17/0467 606/147 |
| 5,002,554 | A | * | 3/1991 | Korber ............... A61B 17/3201 30/120 |
| 5,176,696 | A | * | 1/1993 | Saunders ........... A61B 17/3201 30/340 |
| 5,342,381 | A | | 8/1994 | Tidemand |
| 5,728,112 | A | * | 3/1998 | Yoon ...................... A61B 17/04 606/139 |
| 5,797,958 | A | | 8/1998 | Yoon |
| 6,024,744 | A | | 2/2000 | Kese et al. |
| 6,051,004 | A | * | 4/2000 | Gill ...................... A61B 17/062 606/147 |
| 6,146,399 | A | * | 11/2000 | Lee ...................... A61B 17/282 30/124 |
| 6,301,787 | B2 | * | 10/2001 | Mock ...................... B26B 13/16 30/252 |
| 6,976,992 | B2 | | 12/2005 | Sachatello et al. |
| 7,131,970 | B2 | * | 11/2006 | Moses ................ A61B 18/1442 606/205 |
| 7,410,494 | B2 | | 8/2008 | Kalmann et al. |
| 8,313,495 | B2 | * | 11/2012 | Bates ................ A61B 17/0467 30/194 |
| 8,398,673 | B2 | | 3/2013 | Hinchliffe et al. |
| 8,491,617 | B2 | * | 7/2013 | Reschke ............. A61B 17/285 606/167 |
| 8,496,682 | B2 | | 7/2013 | Guerra et al. |
| 2002/0058965 | A1 | * | 5/2002 | Andrews ............ A61B 17/0206 606/205 |
| 2006/0079891 | A1 | * | 4/2006 | Arts .................. A61B 17/2812 606/51 |
| 2008/0195129 | A1 | | 8/2008 | Weber |
| 2009/0112246 | A1 | * | 4/2009 | Weisshaupt ......... A61B 17/285 606/174 |
| 2009/0163950 | A1 | * | 6/2009 | Waldman ........... A61B 17/0467 606/222 |
| 2011/0054468 | A1 | | 3/2011 | Dycus |
| 2013/0018372 | A1 | * | 1/2013 | Sims ................... A61B 17/285 606/45 |

\* cited by examiner

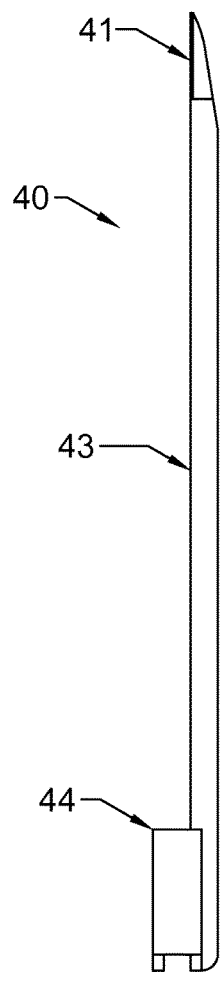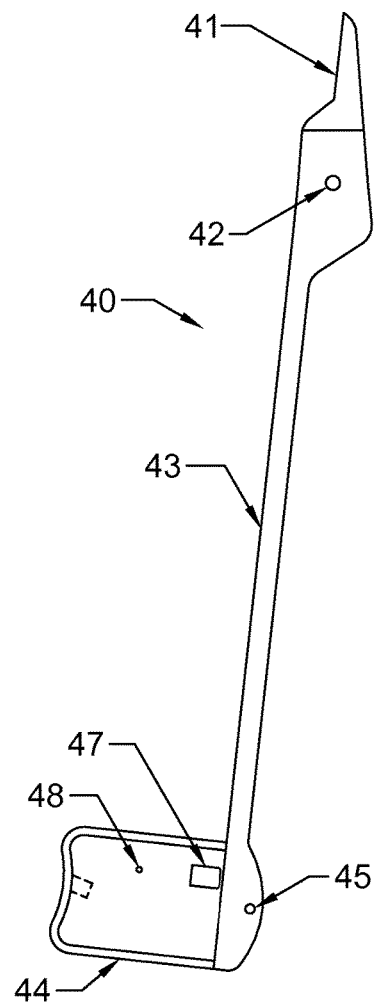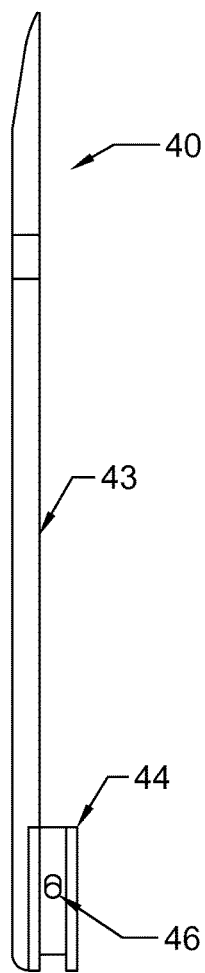
FIG. 14    FIG. 15    FIG. 16
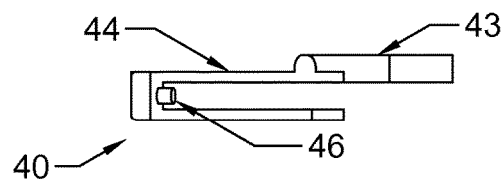
FIG. 17

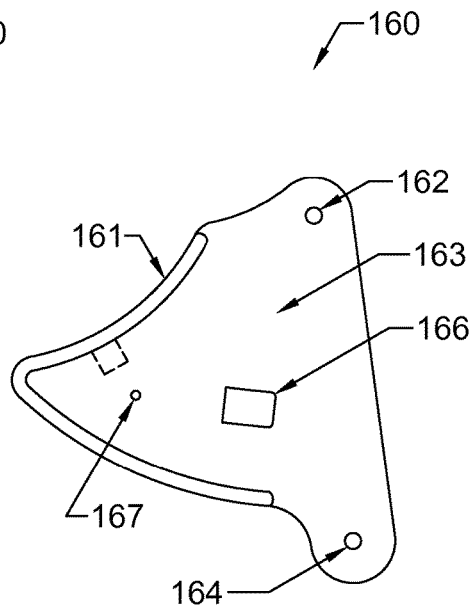
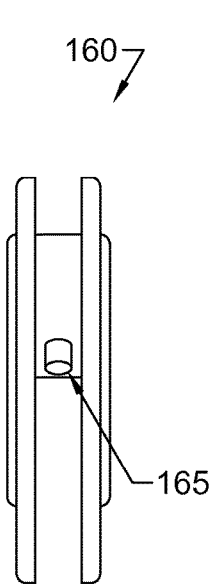
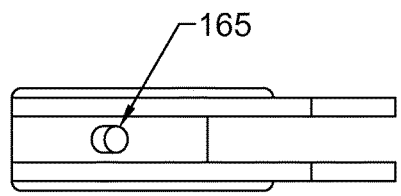
FIG. 35  FIG. 36  FIG. 37
FIG. 38

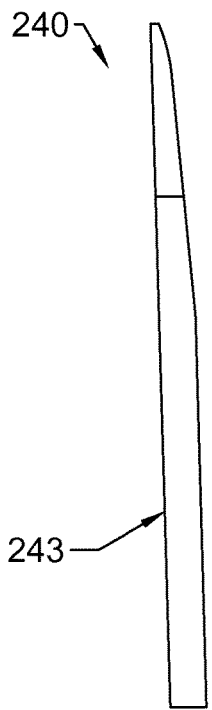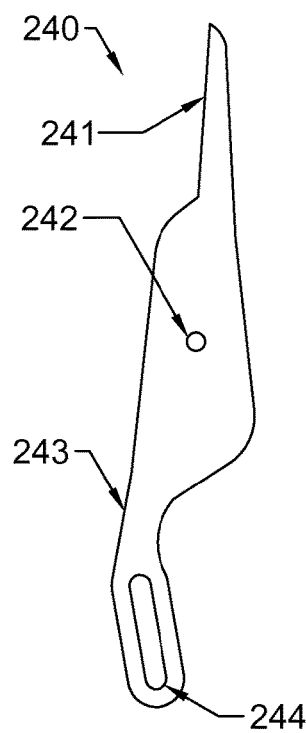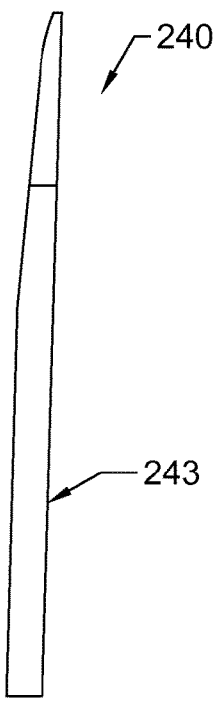
FIG. 53     FIG. 54     FIG. 55
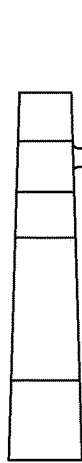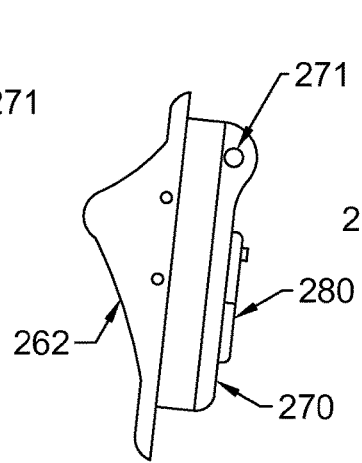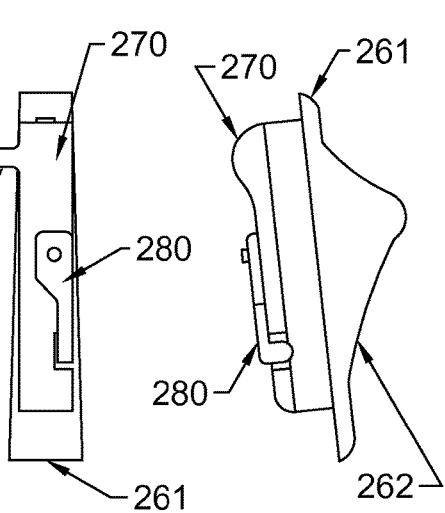
FIG. 56     FIG. 57     FIG. 58     FIG. 59

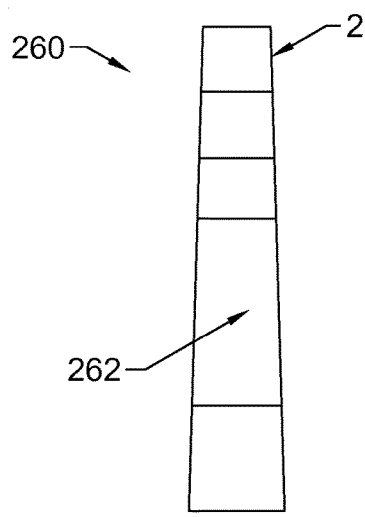
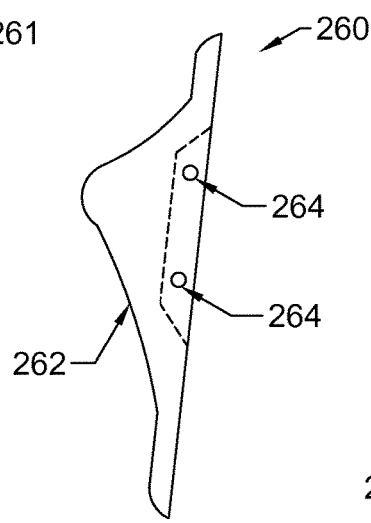
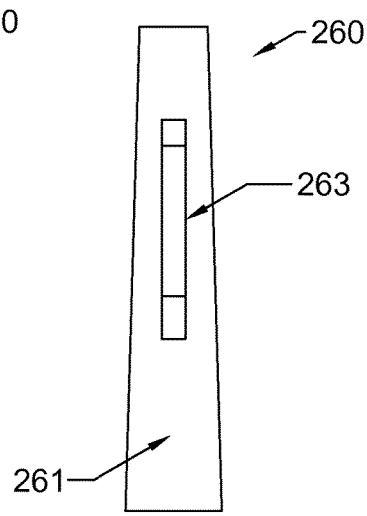
FIG. 60  FIG. 61  FIG. 62
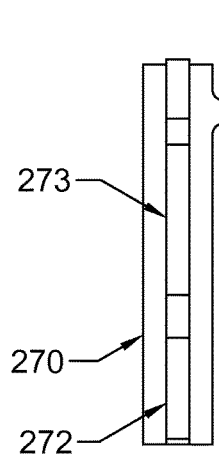
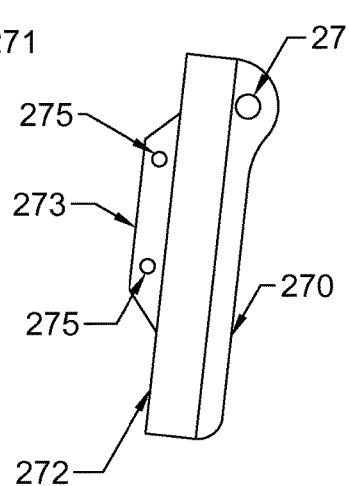
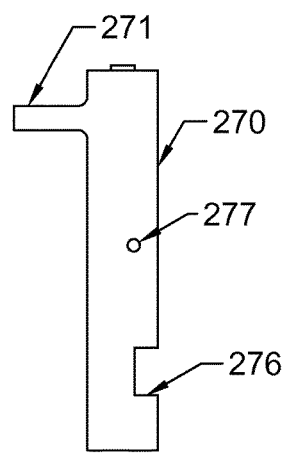
FIG. 63  FIG. 64  FIG. 65
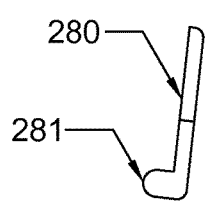
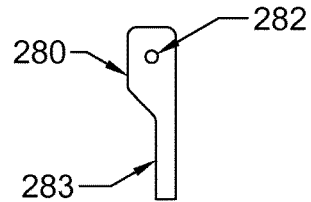
FIG. 66  FIG. 67

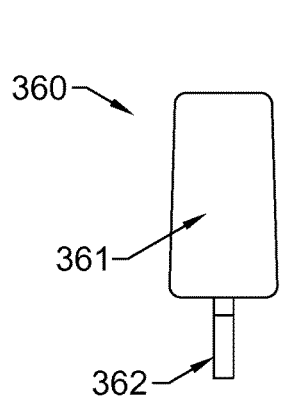
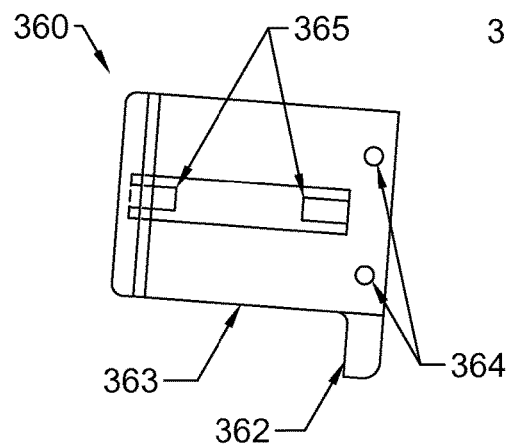
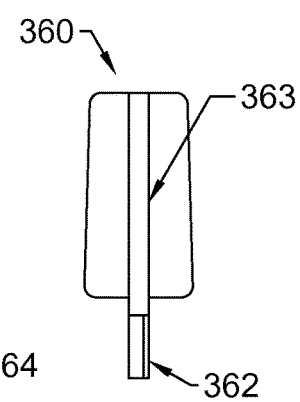
FIG. 87    FIG. 88    FIG. 89
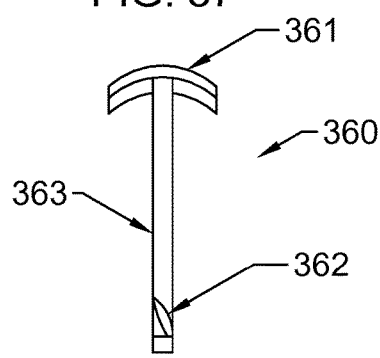
FIG. 90
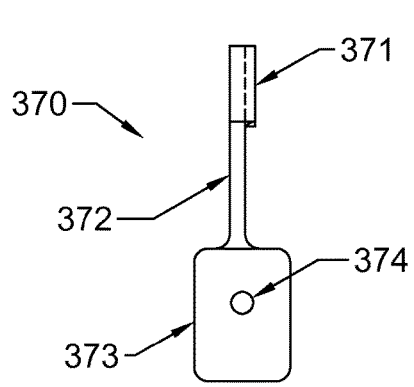
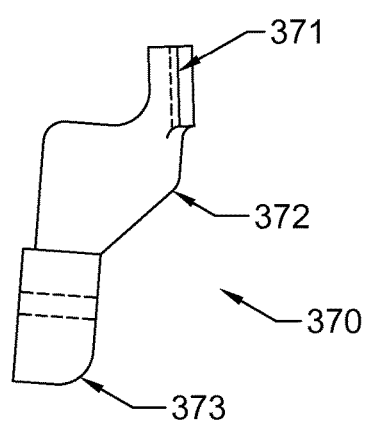
FIG. 91    FIG. 92

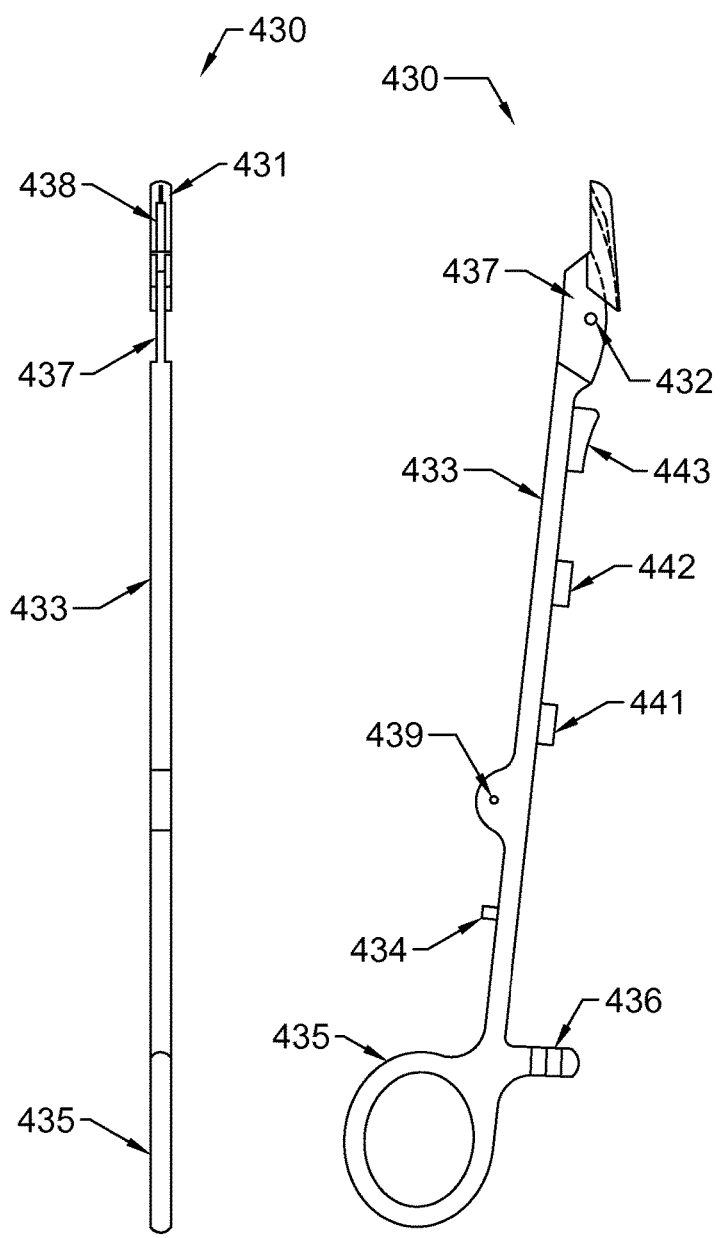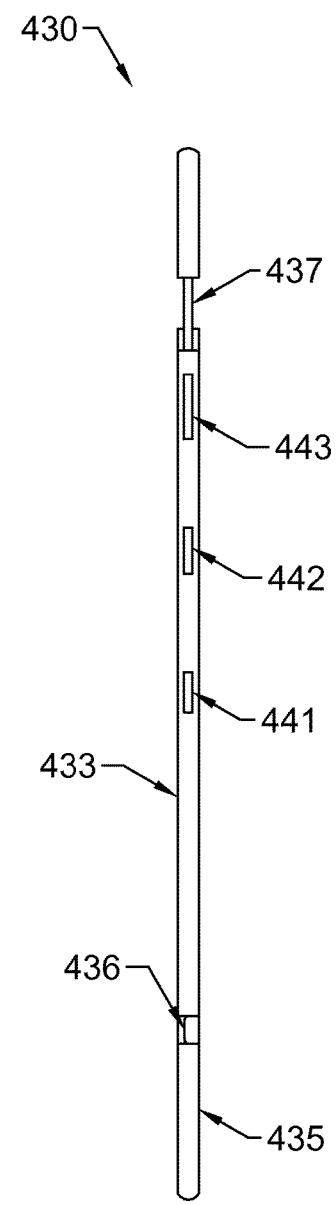
FIG. 102  FIG. 103  FIG. 104

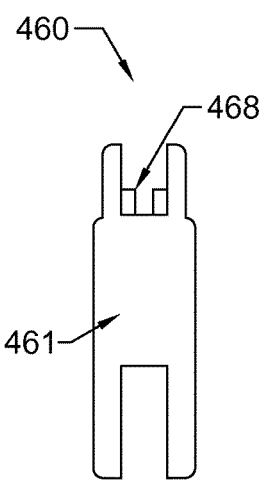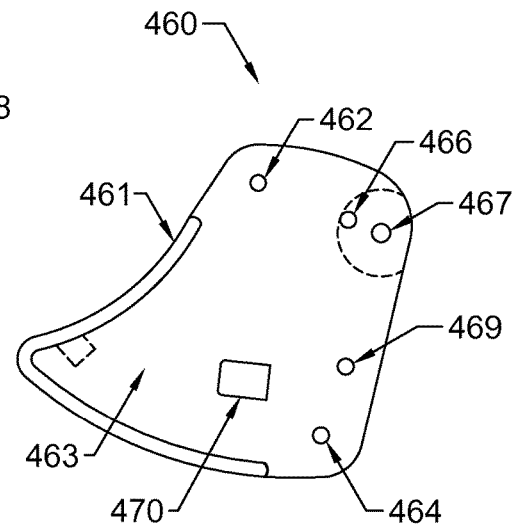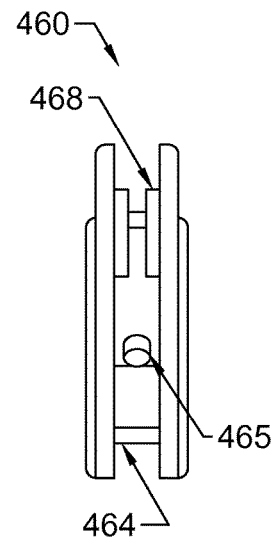
FIG. 108  FIG. 109  FIG. 110
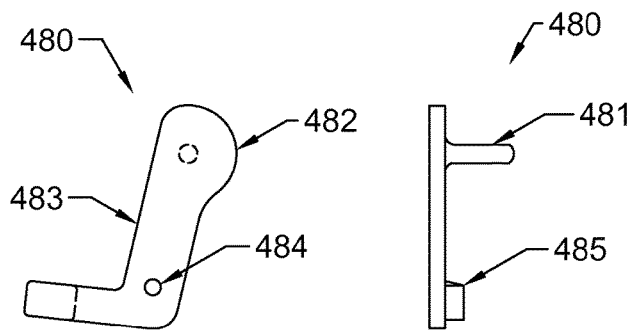
FIG. 111  FIG. 112
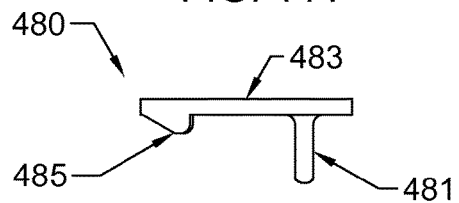
FIG. 113

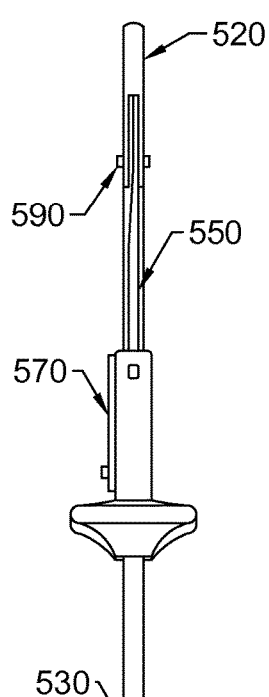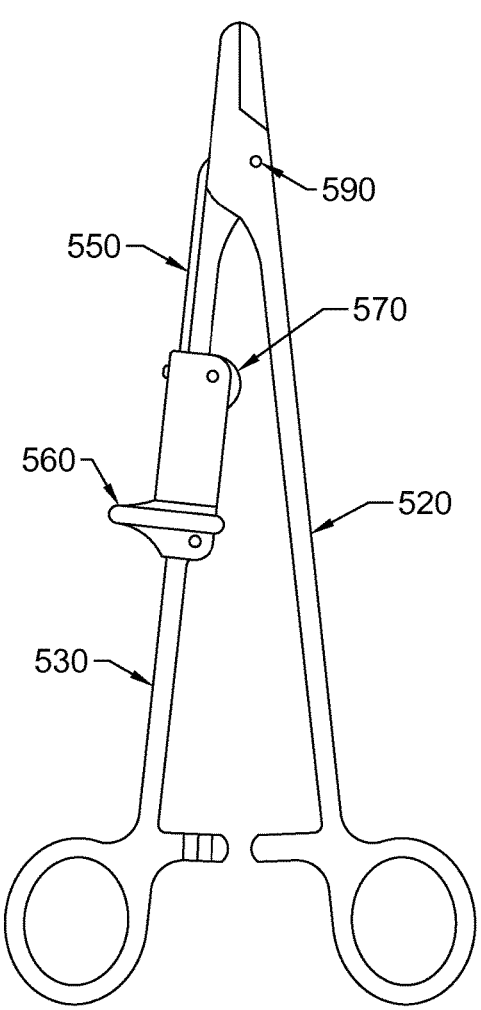
FIG. 116  FIG. 117  FIG. 118

COMBINED NEEDLE HOLDER SCISSORS

CROSS-REFERENCE TO RELATED APPLICATIONS

Priority of my U.S. Provisional Patent Application Ser. No. 61/922,004, filed on 30 Dec. 2013, hereby incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a multi-purpose medical device. More particularly, the present invention relates to a combination grasping and cutting surgical device. The present invention preferably includes at least a pair of grippers for a suture needle and a suture cutter.

2. General Background of the Invention

The present invention includes means for grasping and means for cutting in one device. The novel design allows the operator to both grasp and cut with the same instrument in the critical working area near the end of the main jaws. It is different from prior similar grippers/cutters in that the needle can be gripped at the very end of the grippers (the end distal from the operator), and the working material, i.e. the suture, is also cut at the very end of the grippers. In related prior art, the grippers are at the end of the device, with the cutters closer to the operator, or vice versa (the cutters at the end of the device, with the grippers closer to the operator). Either prior art scenario is not as good, as ideally the gripping and cutting should occur at the very end of the gripping and cutting means, encompassing the same working area of the instrument as a whole. The novel design of the present invention differs from prior inventions which include scissors and needle drivers in one device in that the new invention allows cutting and grasping at the tip of the device in the same working jaws. In previous designs the cutting scissors are proximal to the working jaws of the instrument similar to pliers with a cutting area near the hinge. That design is poorly suited to surgical applications as it requires the operator to open the jaws of the device widely to open the proximal scissors and then advance the instrument into the depth of the wound or working area to apply the cutting surface to the desired target. Passing the device in such manner is often risky as it exposes surrounding tissues or other structures to damage from the intrusion and motion of the tips of the device. Optimum surgical technique dictates that the tips of scissors be employed for cutting, allowing the best visualization of the structure being divided while minimizing risk to other structures from the remainder of the device. Other prior inventions describe combined grasping and cutting devices with the scissor function employed and operating on a separate area of the device such as the back side of the jaws or with the jaws shearing in a plane perpendicular to that of the grasping jaws. The use of such devices would require the operator to adjust, move or flip the instrument to perform the cutting operation, imposing undue difficulty in use and potential danger from the position of end of the device. These delays and risks are minimized with the current invention as it allows the grasping and cutting functions in the same main working area of the instrument at the end of the jaws and with a preferred natural scissor type cutting motion performed by the operator in the same plane or direction as for cutting. Importantly the new device is truly convertible in that it can only cut when the operator has activated the mechanism; otherwise the blade is protected from contacting the material for grasping. Still other combined grasping and cutting instruments have a blade in a channel meant to divide the material being grasped by the jaws. Those devices require two steps for cutting material each time. First the material must be grasped by the instrument. Then, secondly, the cutting blade is activated and caused to traverse the area down the channel and divide the desired material. The steps need to be repeated each time cutting is desired. Again, the current invention differs in that it is effectively and quickly converted into a scissor type cutting device to allow repeated cutting with the device by simply opening and closing the jaws while it is converted for cutting.

The following U.S. Patents are incorporated herein by reference: U.S. Pat. Nos. 4,423,729; 4,527,331; 5,342,381; 5,797,958; 6,024,744; 6,976,992; 7,410,494; 8,398,673; 8,496,682; 8,496,682. Also incorporated herein by reference are U.S. Patent Publications Serial Nos. 2008/0195129; 2011/0054468 and European Patent Publication No. EP2444007A1.

BRIEF SUMMARY OF THE INVENTION

This new invention describes a surgical instrument with combined features for grasping and cutting materials. Most currently used instruments involve one function only requiring the operator or an assistant to switch instruments to perform the next function. The invention involves an instrument with a set of grasping jaws such as found on surgical needle drivers, hemostats, grasping forceps, and clamps. In addition to the grasping jaws for holding and grasping material, it includes at least one cutting shear or scissors that operate in the same main working jaws. It then allows the operator to select either the grasping function or cutting function in the same device. This is useful for many activities such as driving surgical needles into tissue (suturing) as well as tying knots with the instrument. The new device will then allow the operator to cut the suture or other material as desired without changing instruments. It functions as a standard needle holder with grasping and locking functions with the use of two main actuating limbs. Preferably there are rings on the operator end to allow passage of fingers for holding the device. While in use as a needle holder or clamp it will function fully. Importantly it will allow the critical functions of such a device, including firm grasping, and locking onto materials such as surgical needles without slipping to properly pass them through tissue, as well as grasping surgical suture to tie and secure surgical knots. Other actions occasionally employed would function in a standard manner as well such as grasping and maneuvering surgical wire, pins, or tissues. Once the grasping and tying maneuvers are complete and cutting is desired, a separate limb adjacent to the jaws is preferably engaged that moves into position forming a cutting shear to be used in the same main functioning jaws of the instrument. Similarly, when the grasping function is once again desired the cutting mechanism is disengaged and the device can safely be employed as a grasper.

This device allows the operator to perform two important functions in surgery of grasping and cutting in one device. Unlike prior devices this new invention allows both functions in the same critical area of the working jaws distally including near the tip. It is also operated with the use of the same working limbs proximally such that the natural and familiar motion of cutting with scissors in the same location and plane of action of grasping is reproduced. The design allows for efficient and safe operation of the instrument for both functions, as importantly the cutting mechanism is protected from action while it is disengaged. The trigger activation offers an intuitive and ergonomic action to actuate the cutting function. It is anticipated that the design will allow expeditious adoption in use, as the apparatus has a similar feel and basic action to commonly available devices for grasping as well as devices for cutting.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 14 shows a left side view of the first embodiment cutting limb and shear;

FIG. 15 shows a front view of the first embodiment cutting limb and shear;

FIG. 16 shows a right side view of the first embodiment cutting limb and shear;

FIG. 17 shows a bottom view of the first embodiment cutting limb and shear;

FIG. 35 shows a left side view of the second embodiment trigger housing;

FIG. 36 shows a front view of the second embodiment trigger housing;

FIG. 37 shows a right side view of the second embodiment trigger housing;

FIG. 38 shows a bottom view of the second embodiment trigger housing;

FIG. 53 shows a left side view of the third embodiment cutting limb and shear;

FIG. 54 shows a front view of the third embodiment cutting limb and shear;

FIG. 55 shows a right side view of the third embodiment cutting limb and shear;

FIG. 56 shows a left side view of the third embodiment slide activation assembly;

FIG. 57 shows a front view of the third embodiment slide activation assembly;

FIG. 58 shows a right side view of the third embodiment slide activation assembly;

FIG. 59 shows a back view of the third embodiment slide activation assembly;

FIG. 60 shows a left side view of the third embodiment slide activation finger cap;

FIG. 61 shows a front view of the third embodiment slide activation finger cap;

FIG. 62 shows a right side view of the third embodiment slide activation finger cap;

FIG. 63 shows a left side view of the third embodiment slide body;

FIG. 64 shows a front view of the third embodiment slide body;

FIG. 65 shows a right side view of the third embodiment slide body;

FIG. 66 shows a front view of the third embodiment slide detent spring;

FIG. 67 shows a right side view of the third embodiment slide detent spring;

FIG. 87 shows a left side view of the fourth embodiment push button;

FIG. 88 shows a front view of the fourth embodiment push button;

FIG. 89 shows a right side view of the fourth embodiment push button;

FIG. 90 shows a bottom view of the fourth embodiment push button;

FIG. 91 shows a left side view of the fourth embodiment bypass latch;

FIG. 92 shows a front view of the fourth embodiment bypass latch;

FIG. 102 shows a left side view of the fifth embodiment convertible grasping limb;

FIG. 103 shows a front view of the fifth embodiment convertible grasping limb;

FIG. 104 shows a right side view of the fifth embodiment convertible grasping limb;

FIG. 108 shows a left side view of the fifth embodiment trigger mechanism;

FIG. 109 shows a front view of the fifth embodiment trigger mechanism;

FIG. 110 shows a right side view of the fifth embodiment trigger mechanism;

FIG. 111 shows a front view of the fifth embodiment combined retaining pin and feedback spring;

FIG. 112 shows a right side view of the fifth combined retaining pin and feedback spring;

FIG. 113 shows a bottom view of the fifth embodiment combined retaining pin and feedback spring;

FIG. 116 shows a left side view of the sixth embodiment combined needle holder with sliding blade located within the jaw hinge;

FIG. 117 shows a front view of the sixth embodiment with the grasping jaws closed;

FIG. 118 shows a right side view of the sixth embodiment;

FIG. 119 shows a front view of the sixth embodiment with the grasping jaws open;

FIG. 120 shows a front view of the sixth embodiment with the grasping jaws open and the cutting blade partially deployed;

FIG. 121 shows a front view of the sixth embodiment with the grasping jaws open and the cutting blade fully deployed;

FIG. 122 shows a front view of the sixth embodiment with the cutting blade deployed and the device in the cutting position;

FIG. 123 shows a left side view of the sixth embodiment standard grasping limb;

FIG. 124 shows a front view of the sixth embodiment standard grasping limb;

FIG. 125 shows a right side view of the sixth embodiment standard grasping limb;

FIG. 126 shows a left side view of the sixth embodiment convertible grasping limb;

FIG. 127 shows a front view of the sixth embodiment convertible grasping limb;

FIG. 128 shows a right side view of the sixth embodiment convertible grasping limb;

FIG. 129 shows a left side view of the sixth embodiment cutting limb and blade;

FIG. 130 shows a front view of the sixth embodiment cutting limb and blade;

Figures 129, 130, 131, 132:
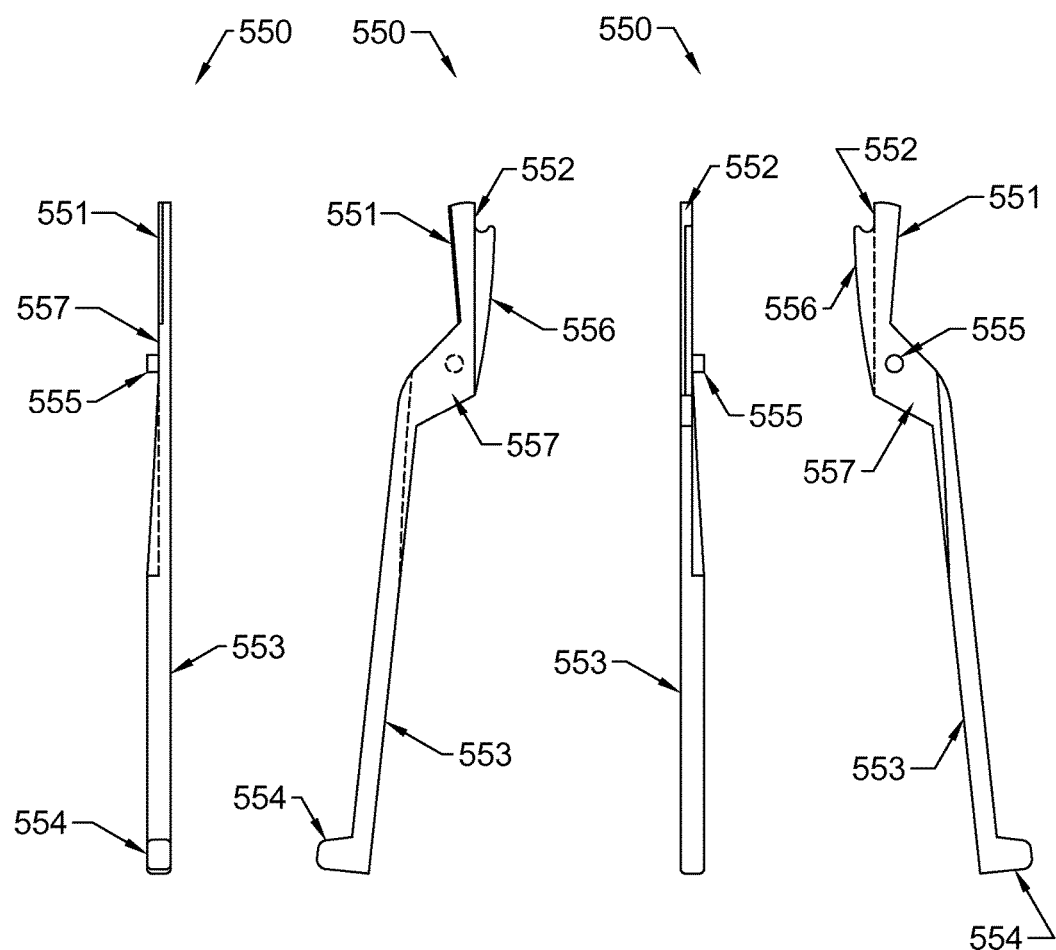
Figures 133, 134, 135:
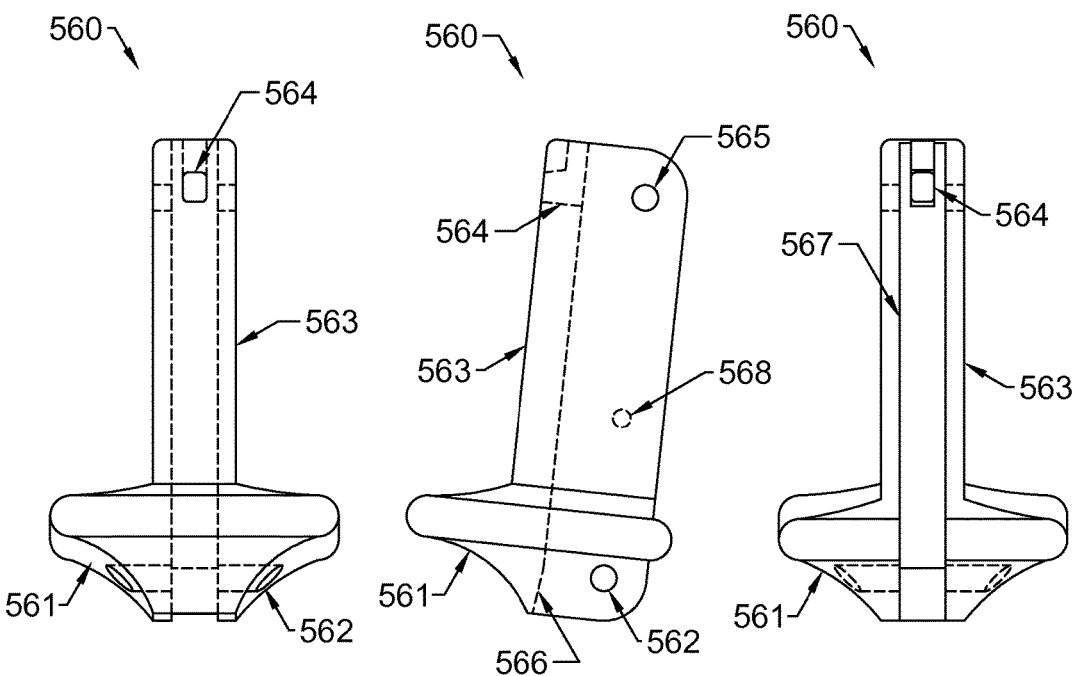
Figures 136, 137:
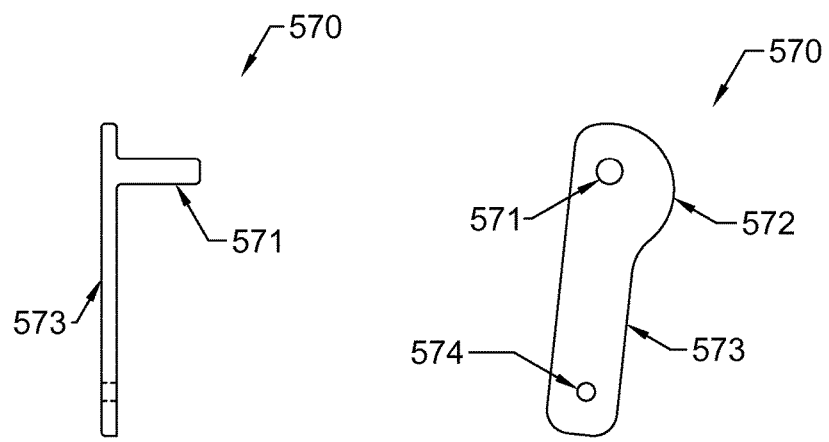
Figure 138:
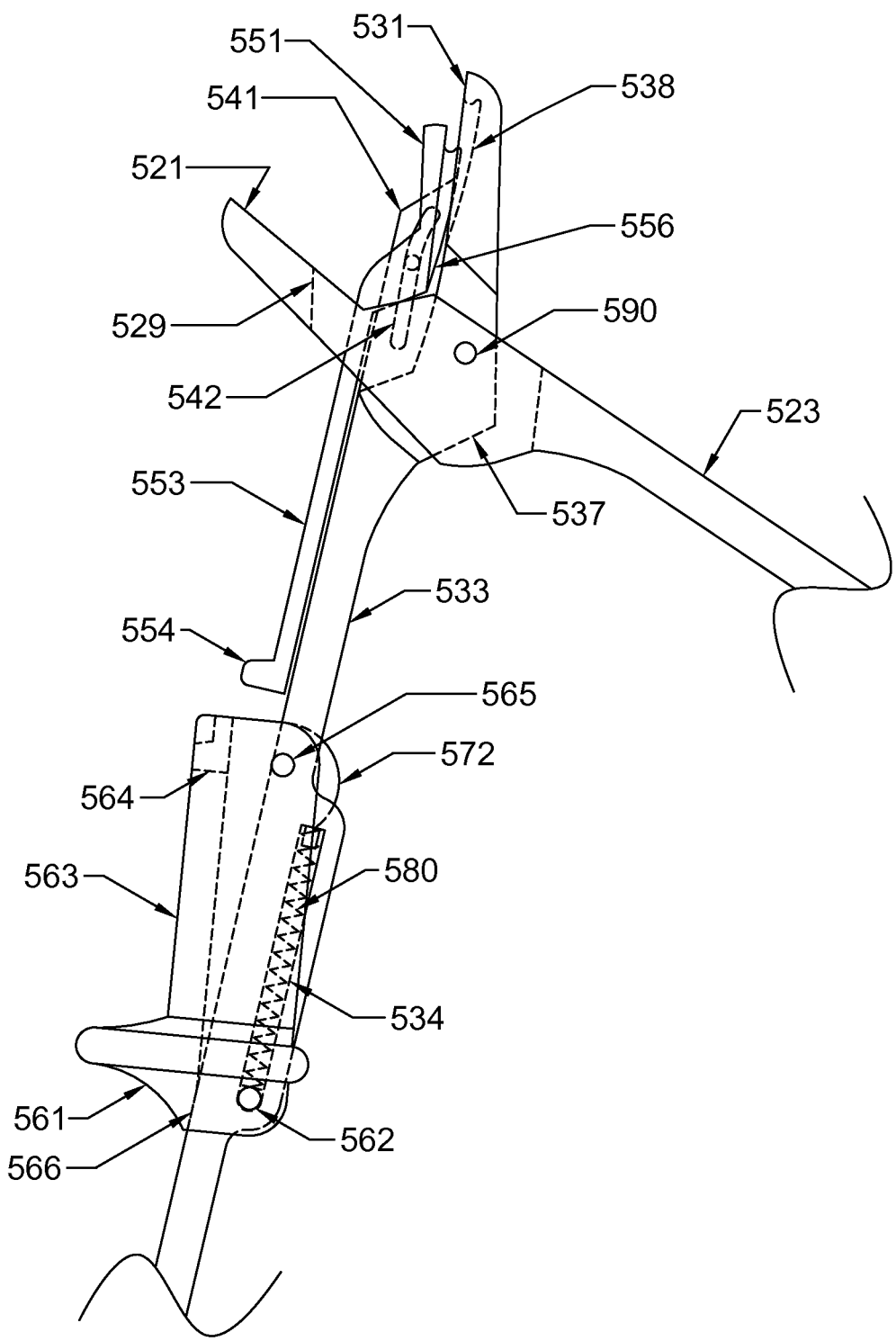
Figures 139, 140, 141:
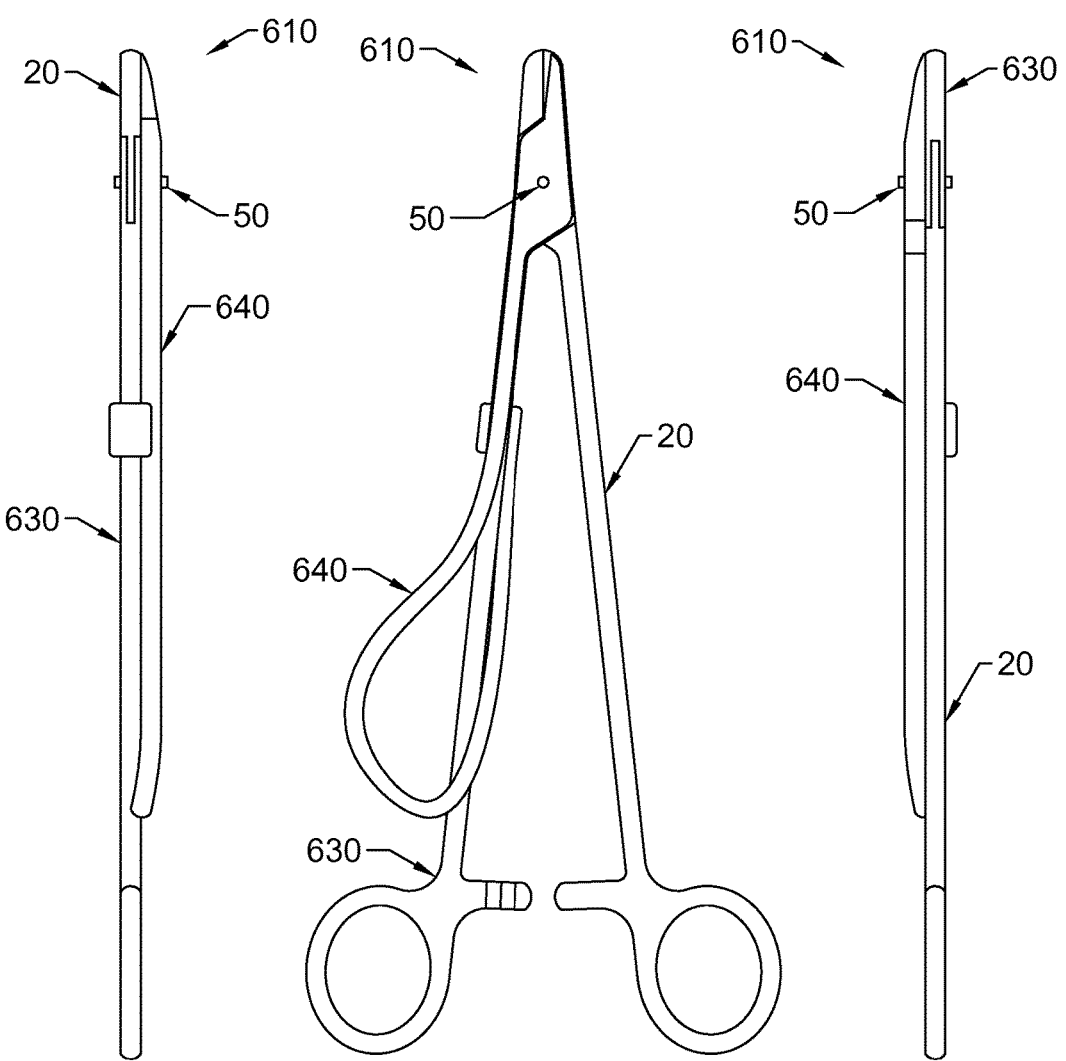
Figure 142:
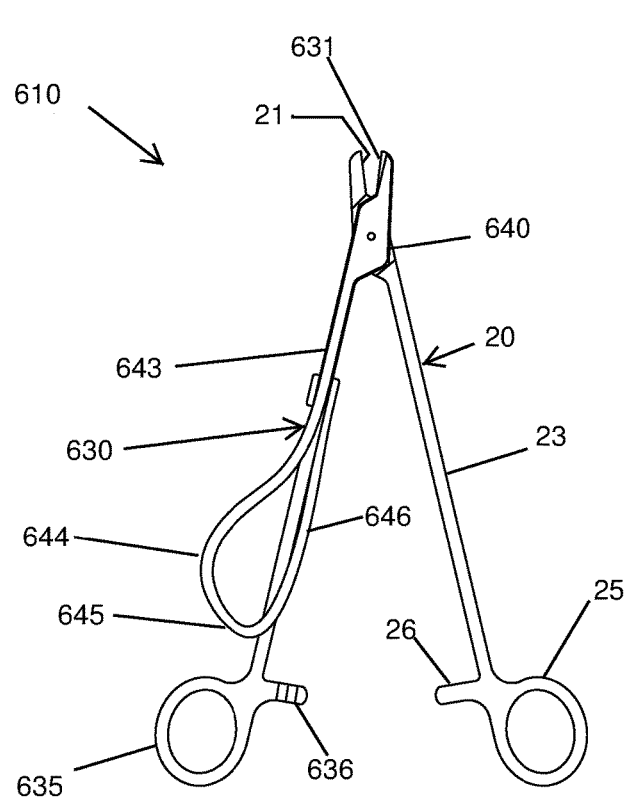
Figure 143:
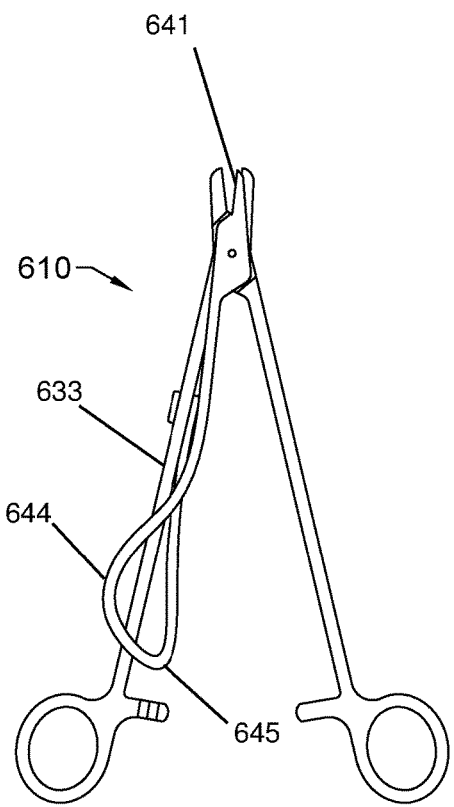
Figure 144:
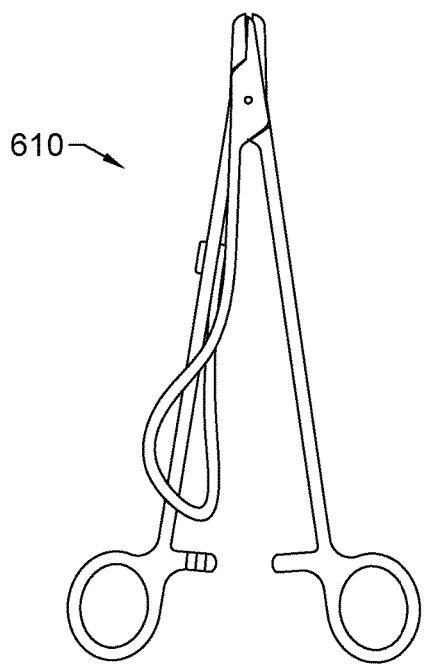
Figure 145:
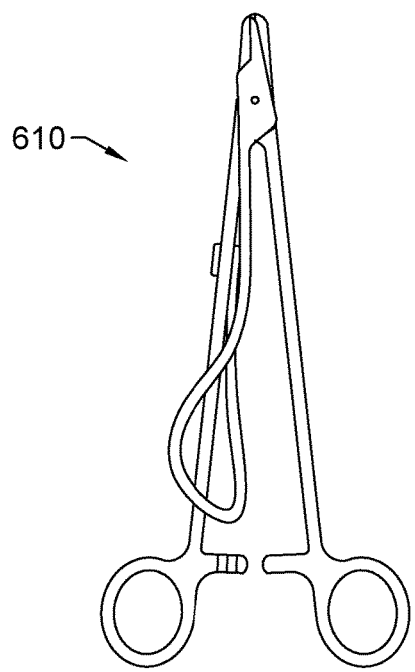
Figure 146:
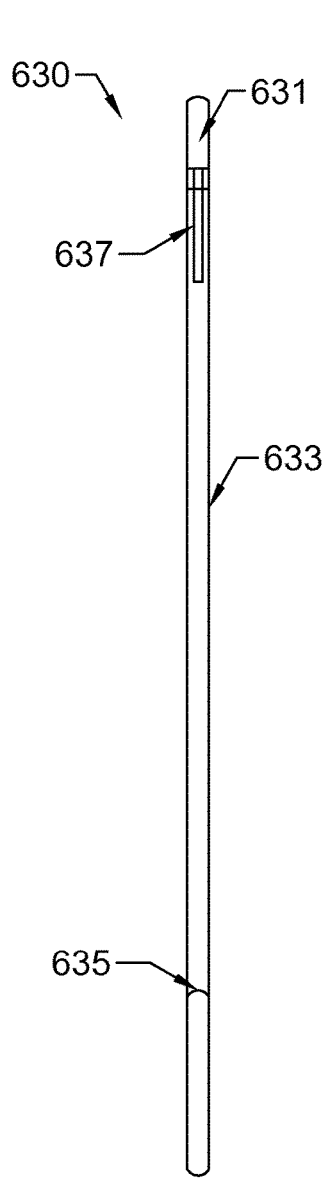
Figure 147:
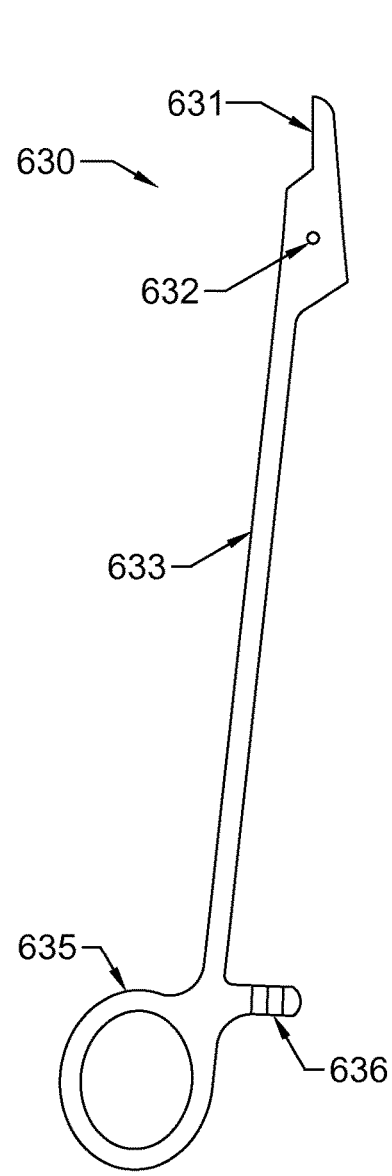
Figure 148:
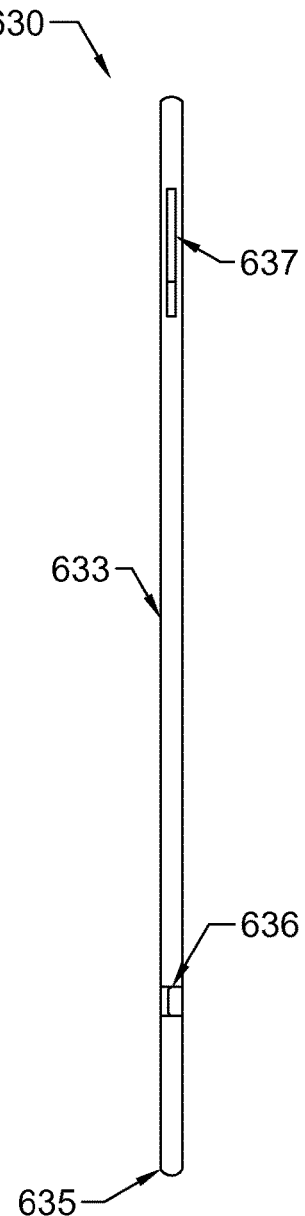
Figure 149:
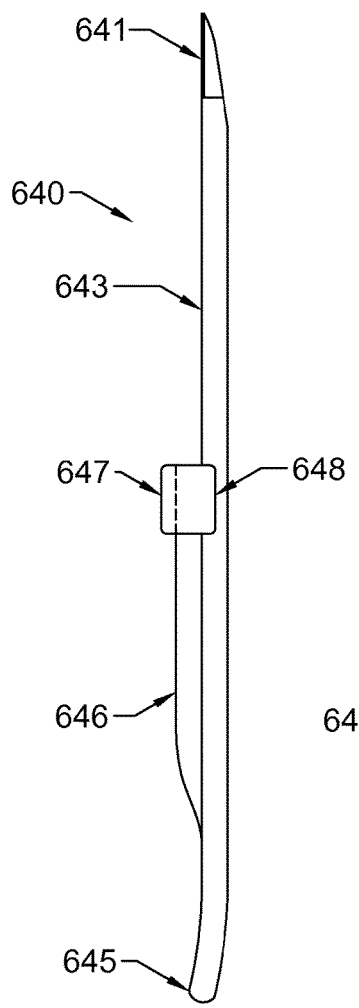
Figure 150:
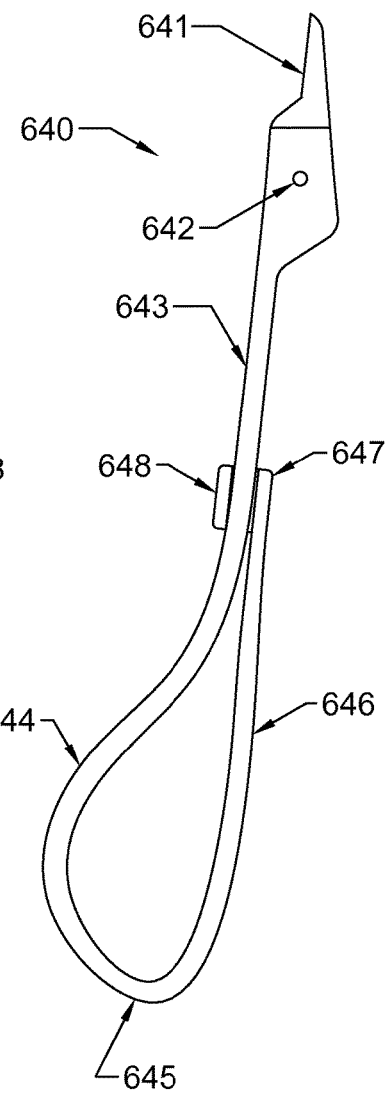
Figure 151:
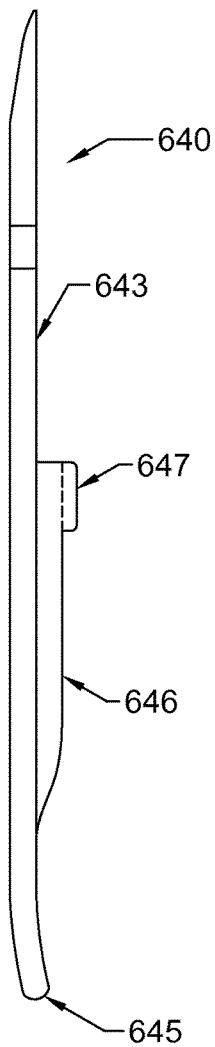

FIG. 131 shows a right side view of the sixth embodiment cutting limb and blade;

FIG. 132 shows a back view of the sixth embodiment cutting limb and blade;

FIG. 133 shows a left side view of the sixth embodiment trigger mechanism;

FIG. 134 shows a front view of the sixth embodiment trigger mechanism;

FIG. 135 shows a right side view of the sixth embodiment trigger mechanism;

FIG. 136 shows a left side view of the sixth embodiment retaining pin and spring;

FIG. 137 shows a front view of the sixth embodiment retaining pin and spring;

FIG. 138 shows a detail view of the sixth embodiment combined needle holder with the jaws wide open to allow cutting blade replacement, and the cutting blade released with the trigger mechanism opened;

FIG. 139 shows a left side view of the seventh embodiment of a combined needle holder with cutting mechanism;

FIG. 140 shows a front view of the seventh embodiment with the grasping mechanism closed;

FIG. 141 shows a right side view of the seventh embodiment;

FIG. 142 shows a front view of the seventh embodiment with the grasping jaws open;

FIG. 143 shows a front view of the seventh embodiment with the grasping jaws open and the cutting mechanism engaged;

FIG. 144 shows a front view of the seventh embodiment with the cutting mechanism engaged and the device cutting distally;

FIG. 145 shows a front view of the seventh embodiment with the cutting mechanism engaged and the grasping jaws closed;

FIG. 146 shows a left side view of the seventh embodiment convertible grasping limb;

FIG. 147 shows a front view of the seventh embodiment convertible grasping limb;

FIG. 148 shows a right side view of the seventh embodiment convertible grasping limb;

FIG. 149 shows a left side view of the seventh embodiment cutting limb and shear;

FIG. 150 shows a front view of the seventh embodiment cutting limb and shear;

FIG. 151 shows a right side view of the seventh embodiment cutting limb and shear.

DETAILED DESCRIPTION OF THE INVENTION

The invention consists of a surgical instrument with two main grasping jaws connected by a hinge. It performs typical functions as grasping locking forceps commonly used as needle holders. The operator employs the instrument for grasping by causing the jaws to open and close. This is typically accomplished by squeezing and opening the proximal end of the device. There are a myriad of sizes shapes and designs applicable to that function. The unique feature of the current invention, however, is that the device can be converted into a cutting instrument that performs the cutting function in the same working area of the device as the grasping function. A cutting shear is outfitted preferably either within or alongside of at least one of the grasping jaws of the device. An additional action of the operator is then employed to activate the cutting shear or blade into position. This can be accomplished by rotating, sliding, twisting or other motions to deploy the cutter into or alongside of the working grasping jaws. After moving into its active position, the cutting shear or shears can then perform the cutting action preferably within the working area of the grasping jaws. Now, when the gasping jaws are closed and then opened, the cutting shear or shears work within the grasping area to cut and divide material present there. Thus the instrument is effectively converted into a scissor type instrument by the action of the operator. The scissors preferably then function in the same working area as was employed for grasping. Similarly, when grasping action is desired the operator can disengage the cutting shear, moving it back into its resting position. The instrument then functions normally as a grasper, as the cutting mechanism is safely retracted from the jaws.

Typical hand held surgical needle holders consist of a pair of limbs attached with a main hinge distally. They are operated proximally by the operator squeezing and releasing the limbs. This invention can be easily applied to such instruments with the addition of at least one cutting limb. The operator can then activate the limb preferably by some mechanism proximally to place the cutting shear into an active position. This invention is also applicable to endoscopic, laparoscopic, or arthroscopic instruments. These instruments are typically elongated allowing the operator to employ the functions of the instrument from an extended end typically outside of the surgical area, often allowing less invasive procedures. The combination grasping jaws and cutting shears of this invention are easily adapted to endoscopic instruments. The typical mechanisms found on such devices are used by the operator manually manipulating the controls on the proximal end which then push or pull on the jaws by a connection down the characteristically long body of the instrument. The cutting shear can preferably be applied adjacent to one of the working jaws of the endoscopic instrument and preferably similarly activated by the operator controlling a separate area on the proximal end pushing, pulling or rotating a control down the body of the instrument. The cutting shear is then activated converting the device from a grasping device into a cutting instrument. Similarly, robotic instruments are employed in surgery for less invasive procedures. This invention is also applicable to robotic instruments. The robotic instruments are used in surgery with the operator controlling them remotely. Via the controls, the operator can use the robotic instruments to perform surgical functions such as grasping, manipulating, and cutting. The current invention can be applied to robotic instruments for combined grasping and cutting functions. The grasping jaws and combined cutting shear can be affixed onto a robotic surgery device to provide both grasping and cutting functions. The device can function in the typical fashion for grasping and manipulation by the via the operator controls. When cutting function is desired, the cutting shear can be moved into an active position by the robotic surgery head. Once the cutting shear is in its active position, it will cut within the main working grasping jaws in the same area that was used for grasping. This will provide the safest and most efficient use of the instrument as a separate cutting instrument is not required to be moved into position. When the cutting function is no longer desired, the operator can preferably deactivate the cutting shear by use of the robotic controls. The shear is then moved back into a safe position by the robotic device. Safe and effective grasping function can then resume.

First Embodiment

Figures 1, 2, 3:
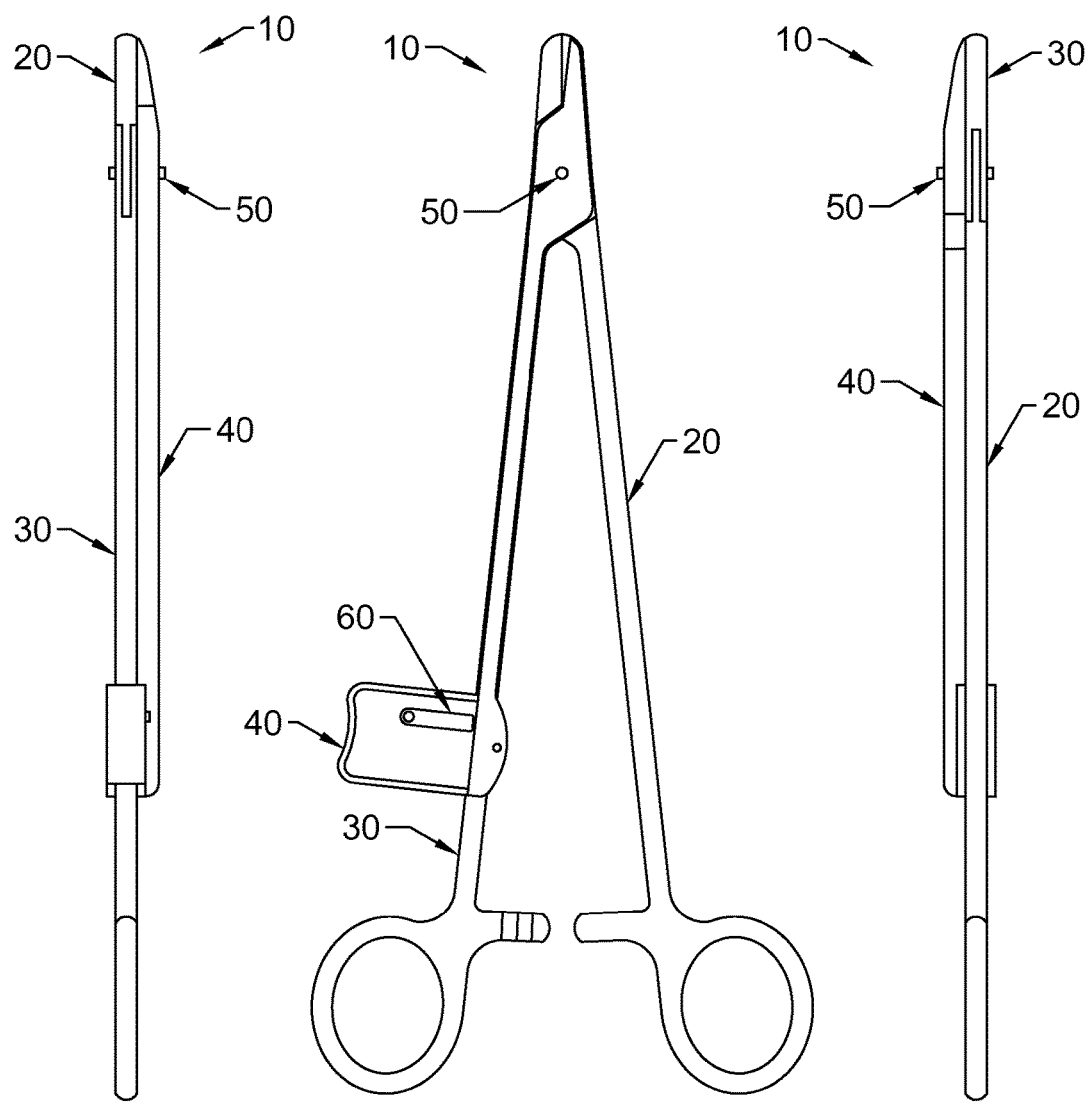
FIG. 1 shows a left side view of the first embodiment of a combined needle holder with cutting mechanism.
FIG. 2 shows a front view of the first embodiment with the grasping mechanism closed.
FIG. 3 shows a right side view of the first embodiment.
Figure 4:
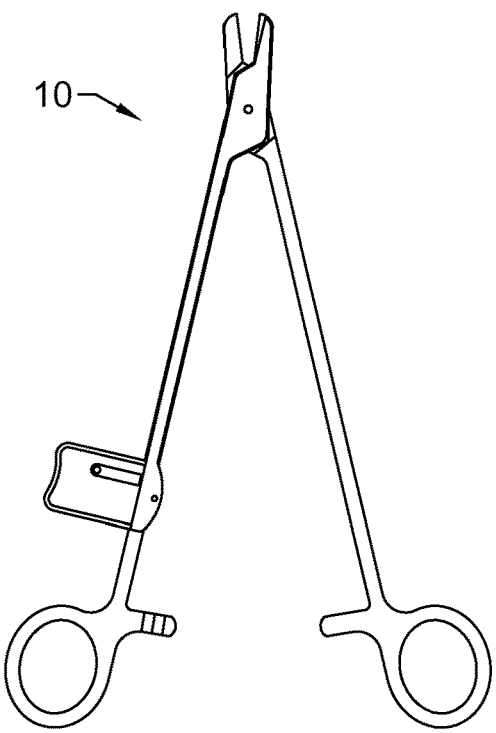
FIG. 4 shows a front view of the first embodiment with the grasping jaws open.
Figure 5:
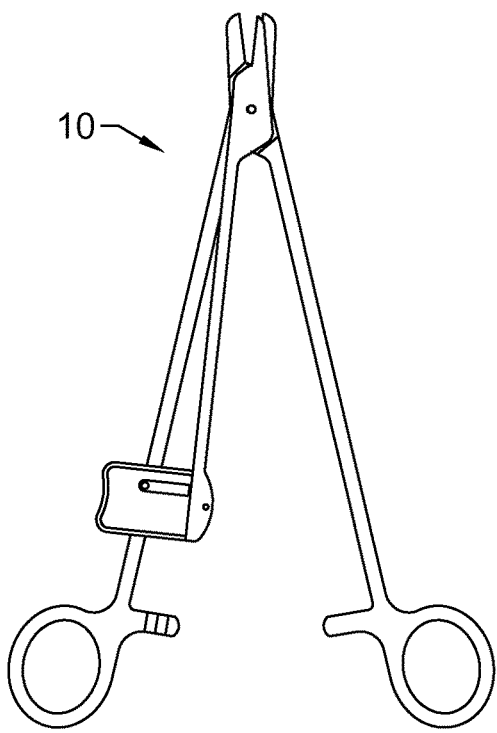
FIG. 5 shows a front view of the first embodiment with the grasping jaws open and the cutting mechanism engaged.
Figure 6:
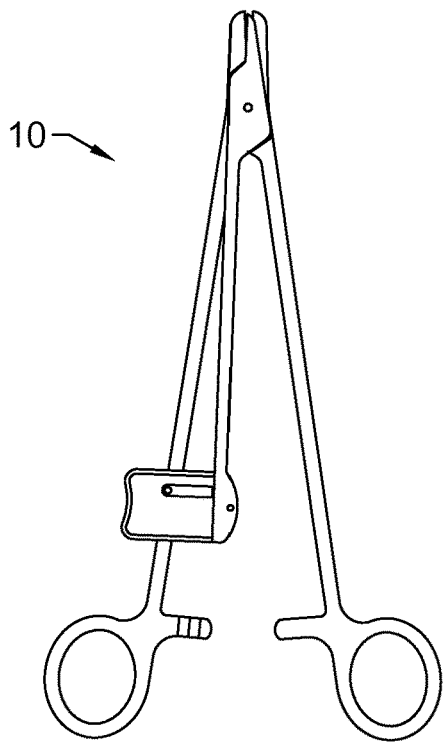
FIG. 6 shows a front view of the first embodiment with the cutting mechanism engaged and the device cutting distally.
Figure 7:
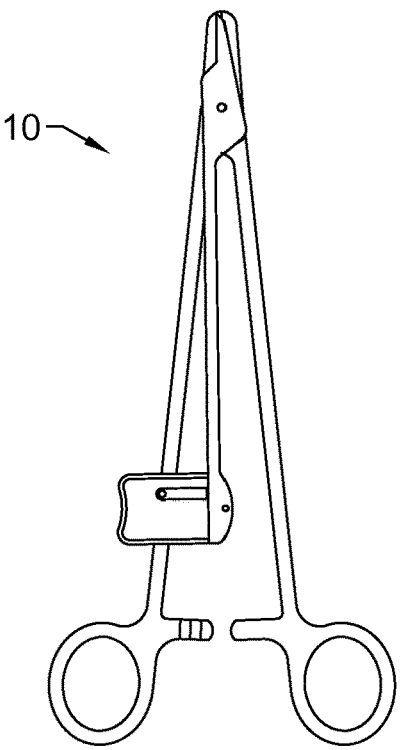
FIG. 7 shows a front view of the first embodiment with the cutting mechanism engaged and the grasping jaws closed.
Figures 8, 9, 10:
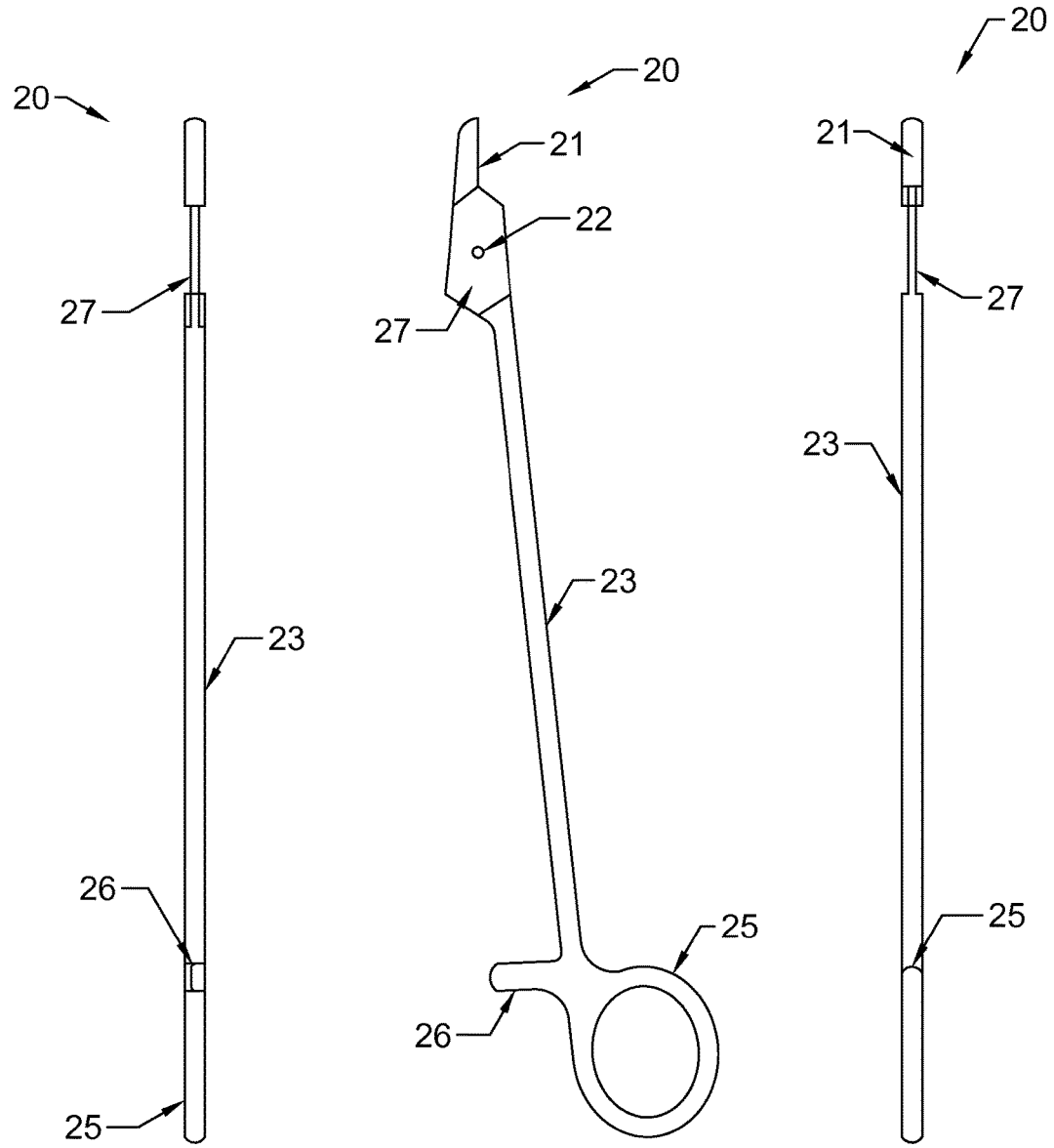
FIG. 8 shows a left side view of the first, second and seventh embodiment standard grasping limb.
FIG. 9 shows a front view of the first, second and seventh embodiment standard grasping limb.
FIG. 10 shows a right side view of the first, second and seventh embodiment standard grasping limb.
Figure 11:
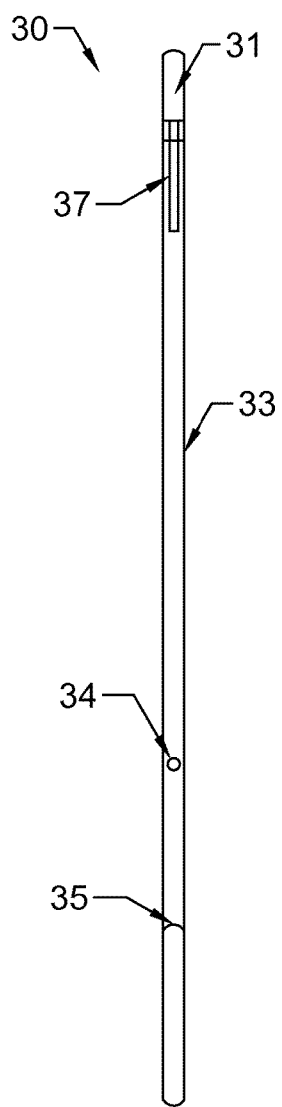
FIG. 11 shows a left side view of the first embodiment convertible grasping limb.
Figure 12:
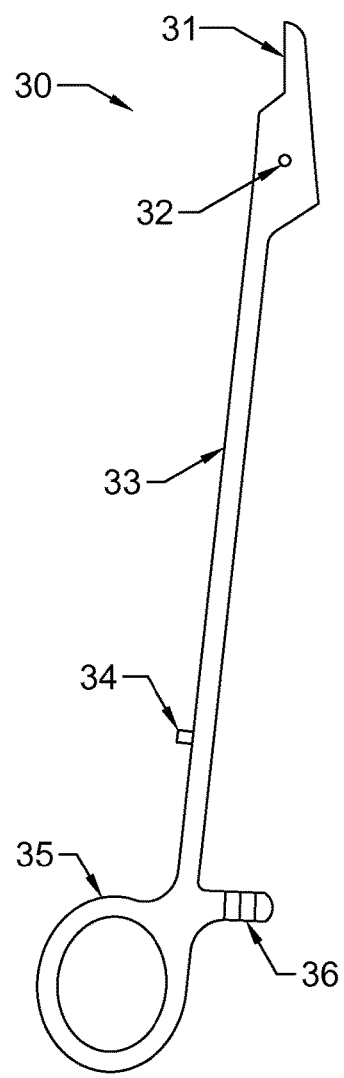
FIG. 12 shows a front view of the first embodiment convertible grasping limb.
Figure 13:
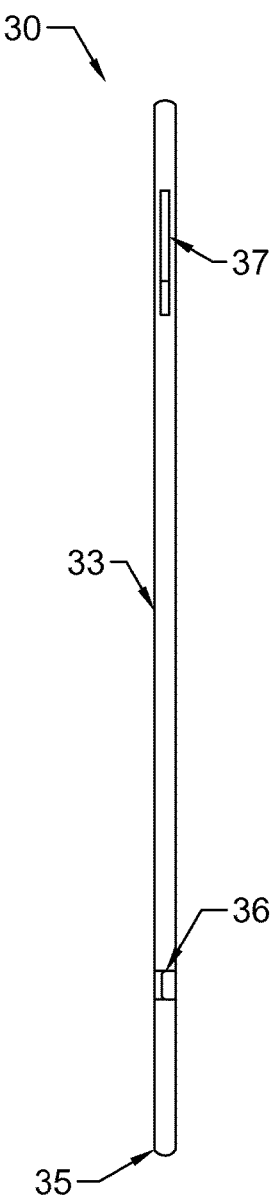
FIG. 13 shows a right side view of the first embodiment convertible grasping limb.
Figure 18:
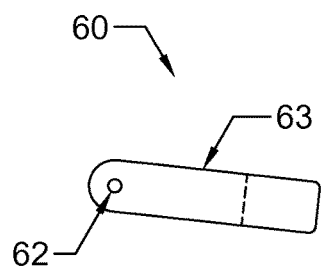
FIG. 18 shows a front view of the first embodiment leaf spring.
Figure 19:
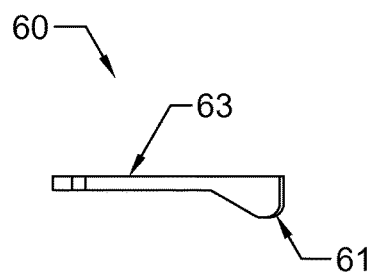
FIG. 19 shows a bottom view of the first embodiment leaf spring.
Figure 21:
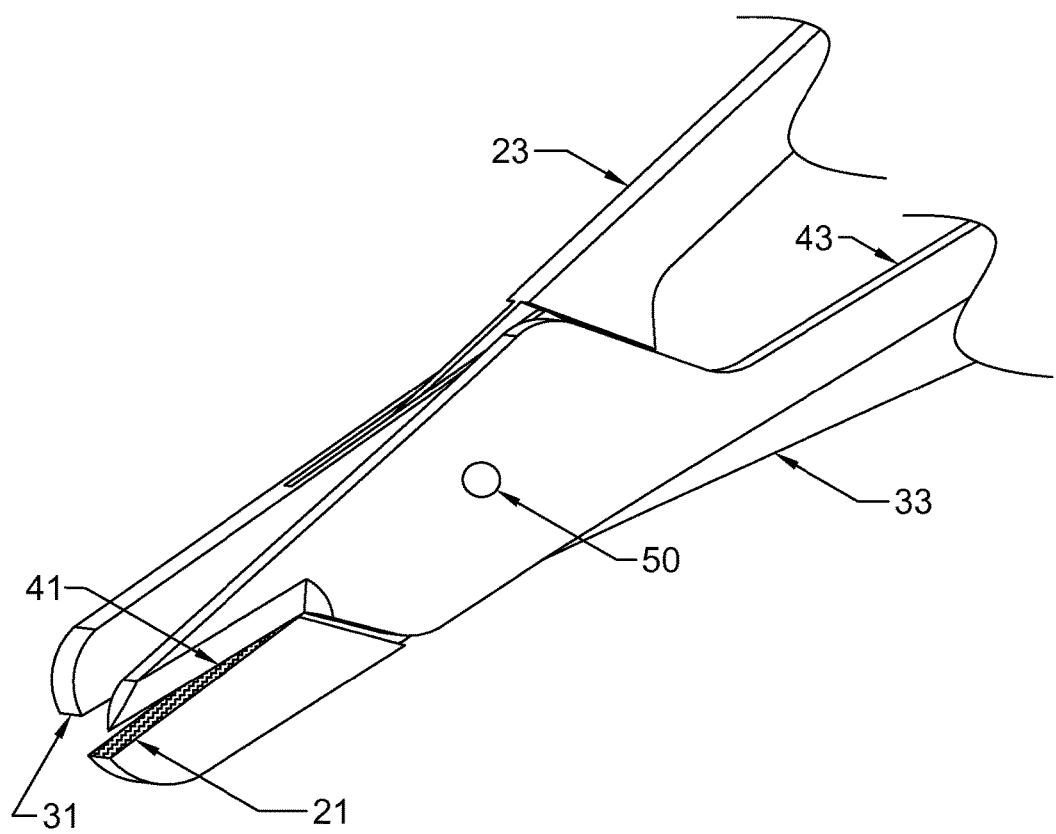
FIG. 21 shows a detail isometric view of the working end of the first embodiment with the jaws open and the cutting shear activated and is representative of the action of the second, third, fourth and seventh embodiments also.

The first embodiment 10 of this invention describes an application of the invention on a standard set of needle holders (or needle drivers.) (FIG. 2) The apparatus consists of a pair of grasping jaws 21, 31 connected by a hinge 50 near the jaws. The proximal ends of the limbs are presented for use by the operator to open and close the grasping jaws of the device. (FIG. 4) Finger rings 25, 35 are most often desired on the proximal end. Separating and opposing the proximal limbs activates the jaws, strongly opening and closing them. Additionally, ratcheting locking teeth 26, 36 on the proximal end are desirable to allow the device to remain "locked" closed when the serrated teeth are engaged. They can be deactivated in the typical fashion by applying pressure slightly perpendicular to the plane of the limbs to disengage the teeth allowing the device to open again. Additionally, the invention employs a cutting device adjacent to the jaws of the instrument. This cutting limb 40 may be attached to and rotate about the main hinge 50 of the device or may be connected about a different axis and or plane of action. When desired, the cutting implement 41 is preferably activated by rotating into position next to the active convertible grasping jaw 31 to lie ahead of the grasping surface in the working jaws. (FIG. 5) While engaged, the shear 41 will then oppose and cut against or cut by the standard grasping jaw 21. Now, when the instrument 10 is used by separating and opposing the proximal limbs, the distal jaw 21 and shear 41 will function as cutting shears or scissors. (FIG. 6) The instrument can then be repeatedly used as a cutting scissor device with standard opening and closing motions. (FIG. 21) Once desired, the cutting shear 41 can be rotated back into its resting position returning the device back into the normal grasping and locking function.

Figure 20:
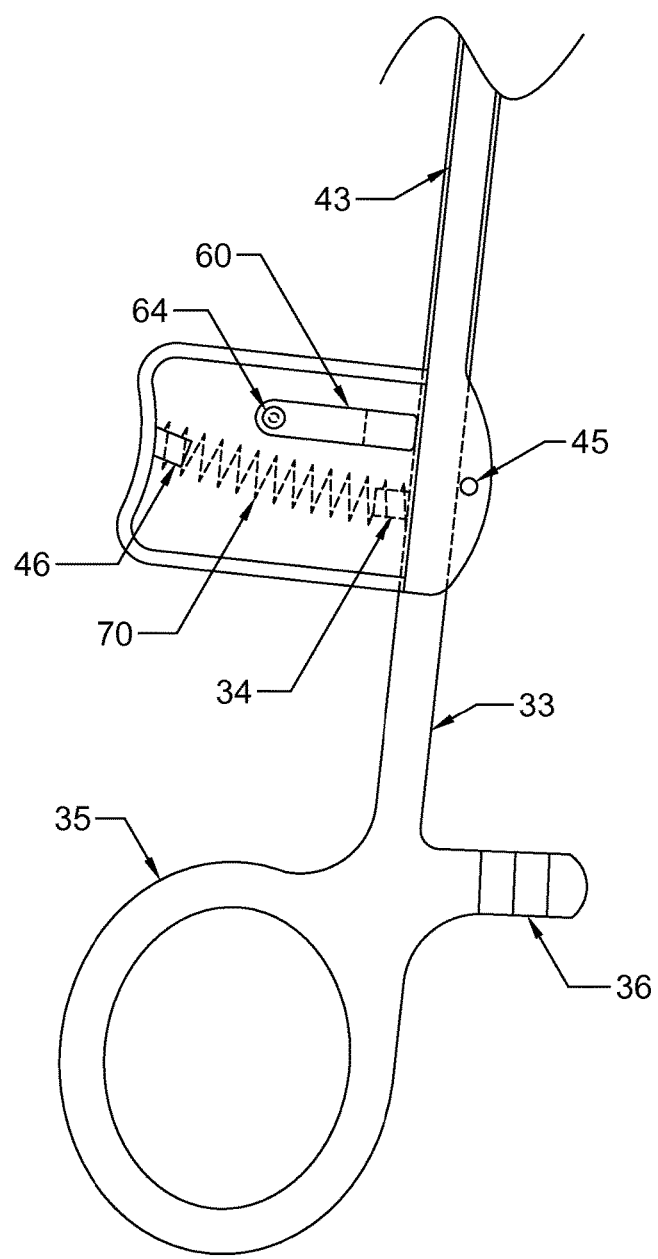
FIG. 20 shows a detail view of the first embodiment activation tab including the internal reset spring.

(FIG. 4) Importantly, once deactivated by rotating the shear 41 into its resting position, it is inherently protected from cutting or damaging other material by resting the shear against the side of the convertible jaw 31. The cutting mechanism is preferably activated by depressing an activation area or tab 44 on the proximal end of the cutting shear limb near the operator. It is suggested that this will be performed with the index finger of the operator as the thumb and ring finger are typically placed in the "finger rings" 25, 35. When the operator depresses the area squeezing it towards the adjacent operating limb, the cutting limb 40 rotates about the main axis of the device. That motion results in the rotation of the cutting shear 41 distally into the jaws of the device. Once in position and activated the operator simply holds the cutting limb 40 rotated into position preferably by maintaining pressure on the activation tab 44. Tactile feedback is desirable and is preferably provided to the operator when the cutting limb 40 is employed. This is preferably accomplished with a small leaf spring 60 attached to the activation tab 44. The attached head 61 passes over the adjacent shaft 33 of the convertible limb of the device as the cutting limb 40 is rotated past it. While the cutting shear 41 is held into an activated position, the device will function similar to a pair of scissors, performing the cutting function in the same main operating area near the end of the instrument as was used for grasping. Once cutting function is no longer desired the operator can simply release the activation tab 44 to rotate the cutting limb 40 back to its inactive position. Automatic and safe return of the device to a grasping function is desirable and accomplished with the use of a reset spring 70 inside the activation tab 44 secured via posts 34, 46. (FIG. 20) The reset spring 70 is preferably compressed during the squeezing action of the operator as the cutting limb 40 rotates into position. When it is released the reset spring 70 expands applying force between the convertible limb shaft 33 and the inside of the activation tab 44. This force separates the two portions rotating the cutting limb automatically back into an inactive position, simultaneously rotating and deactivating the cutting shear 41. Finally as the cutting shear 41 reaches its inactive position the leaf springhead 61 preferably attached to the activation tab 44 preferably passes over the shaft 33 of the convertible limb providing tactile and audible feedback that the device is safely reset back to a grasping function. The instrument 10 can then be used in its usual fashion operating repeatedly as a grasper, including locking until such time as cutting is once more desired. The cutting mechanism can then be reapplied as desired in the same fashion.

Second Embodiment

Figures 22, 23, 24:
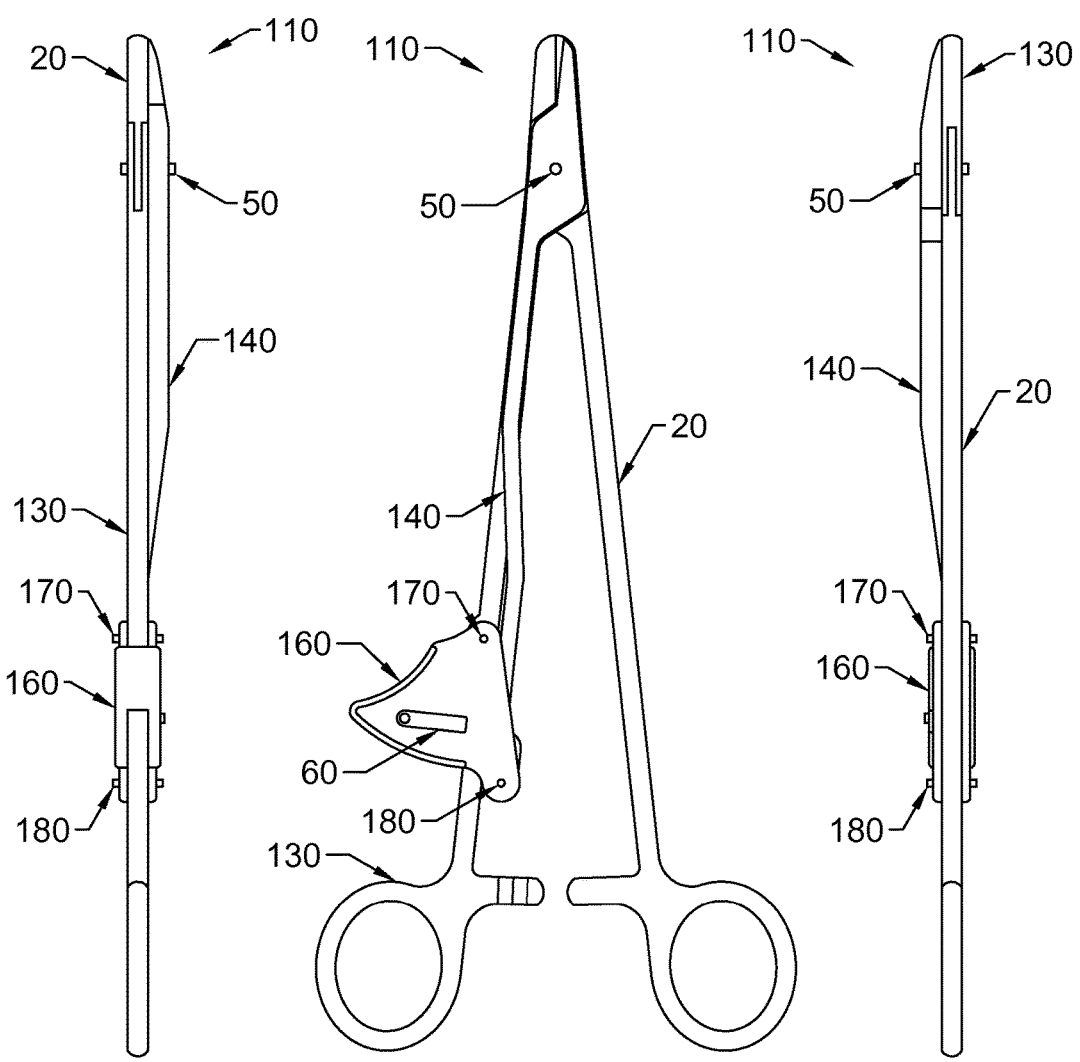
FIG. 22 shows a left side view of the second embodiment combined needle holder with cutting mechanism featuring a trigger activation.
FIG. 23 shows a front view of the second embodiment with the grasping mechanism closed.
FIG. 24 shows a right side view of the second embodiment.
Figure 25:
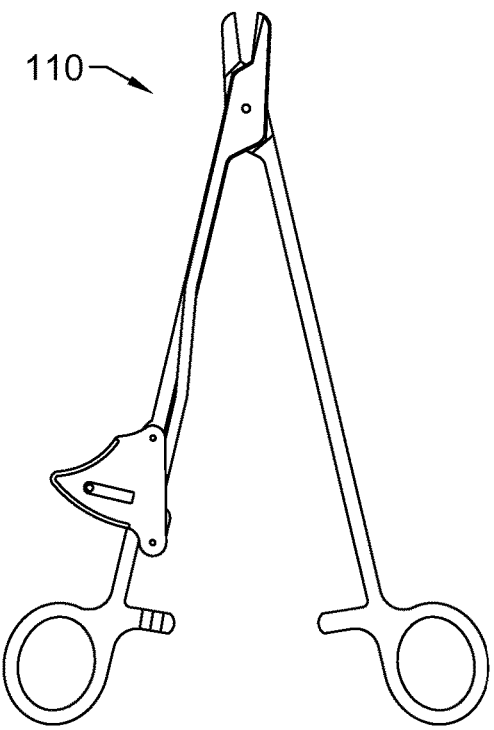
FIG. 25 shows a front view of the second embodiment with the grasping jaws open.
Figure 26:
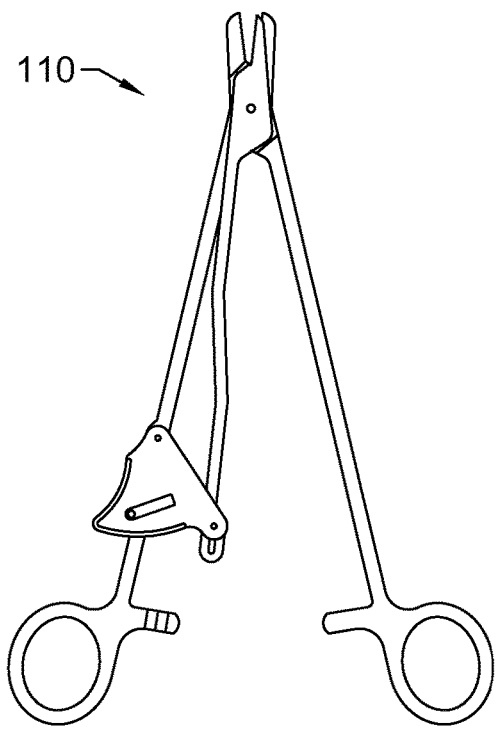
FIG. 26 shows a front view of the second embodiment with the grasping jaws open and the cutting mechanism engaged.
Figure 27:
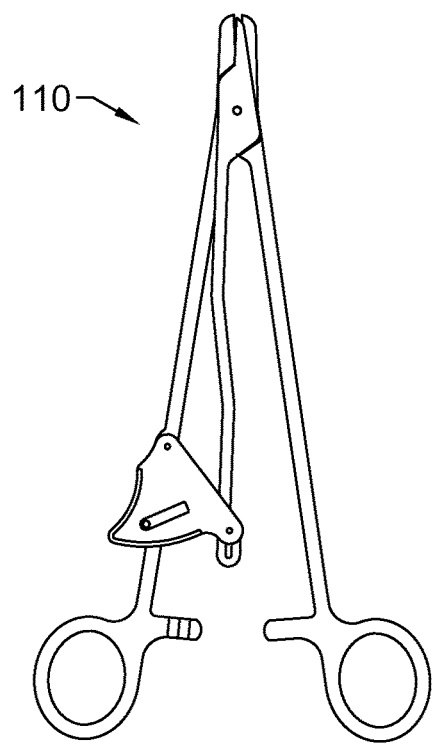
FIG. 27 shows a front view of the second embodiment with the cutting mechanism engaged and the device cutting distally.
Figure 28:
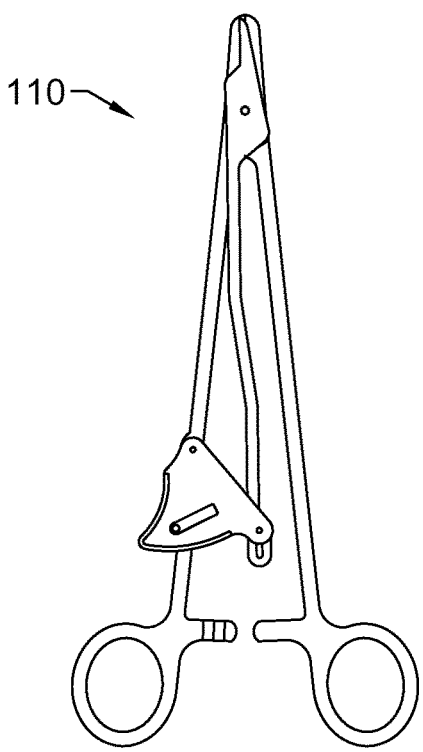
FIG. 28 shows a front view of the second embodiment with the cutting mechanism engaged and the jaws closed.
Figure 29:
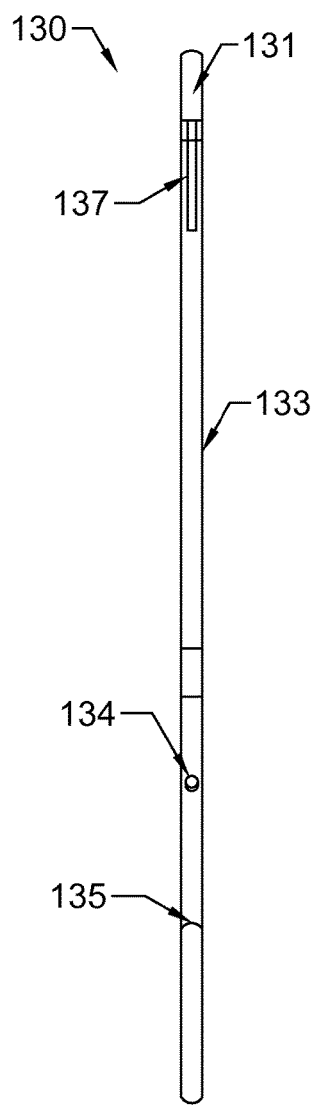
FIG. 29 shows a left side view of the second embodiment convertible grasping limb.
Figure 30:
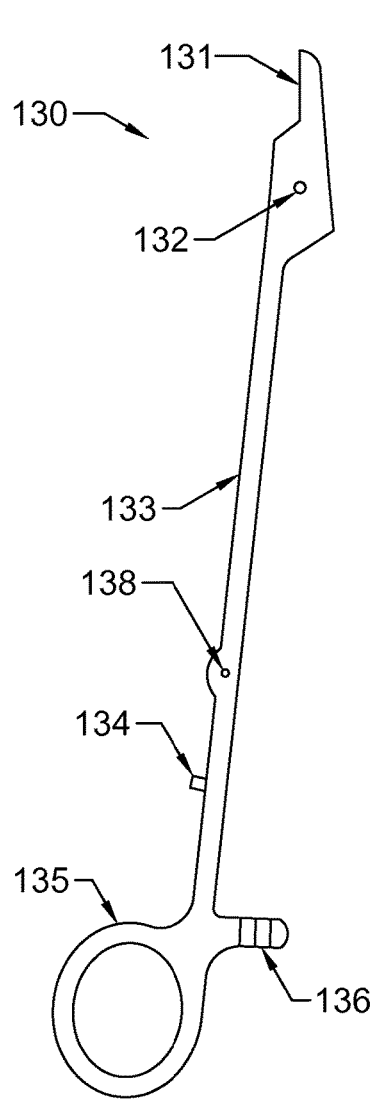
FIG. 30 shows a front view of the second embodiment convertible grasping limb.
Figure 31:
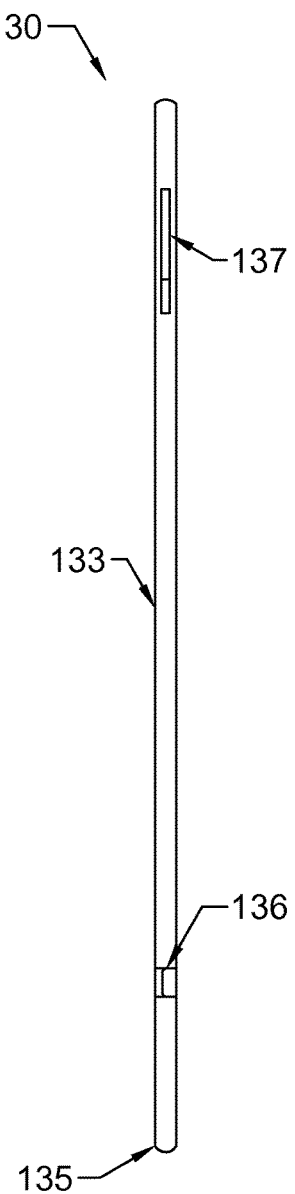
FIG. 31 shows a right side view of the second embodiment convertible grasping limb.
Figure 32:
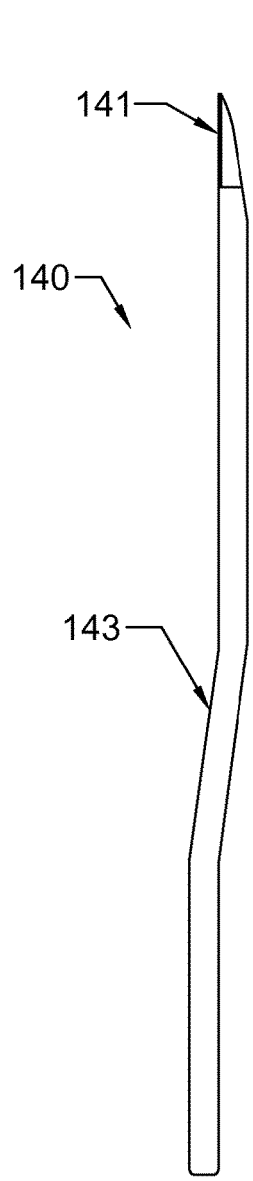
FIG. 32 shows a left side view of the second embodiment cutting limb and shear.
Figure 33:
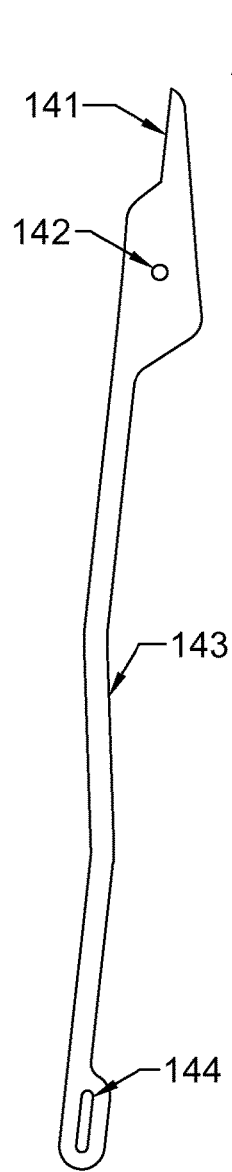
FIG. 33 shows a front view of the second embodiment cutting limb and shear.
Figure 34:
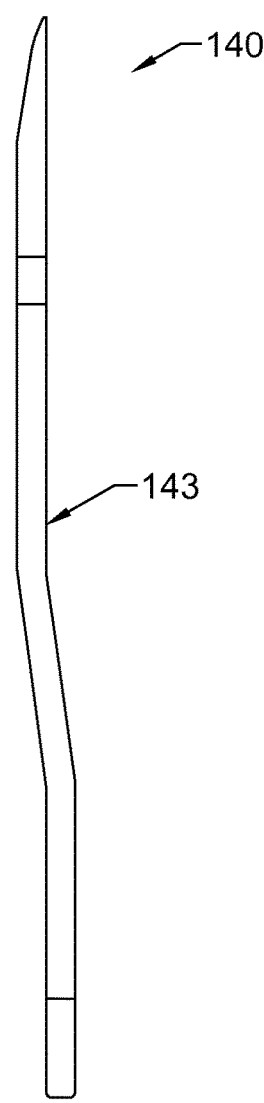
FIG. 34 shows a right side view of the second embodiment cutting limb and shear.
Figure 39:
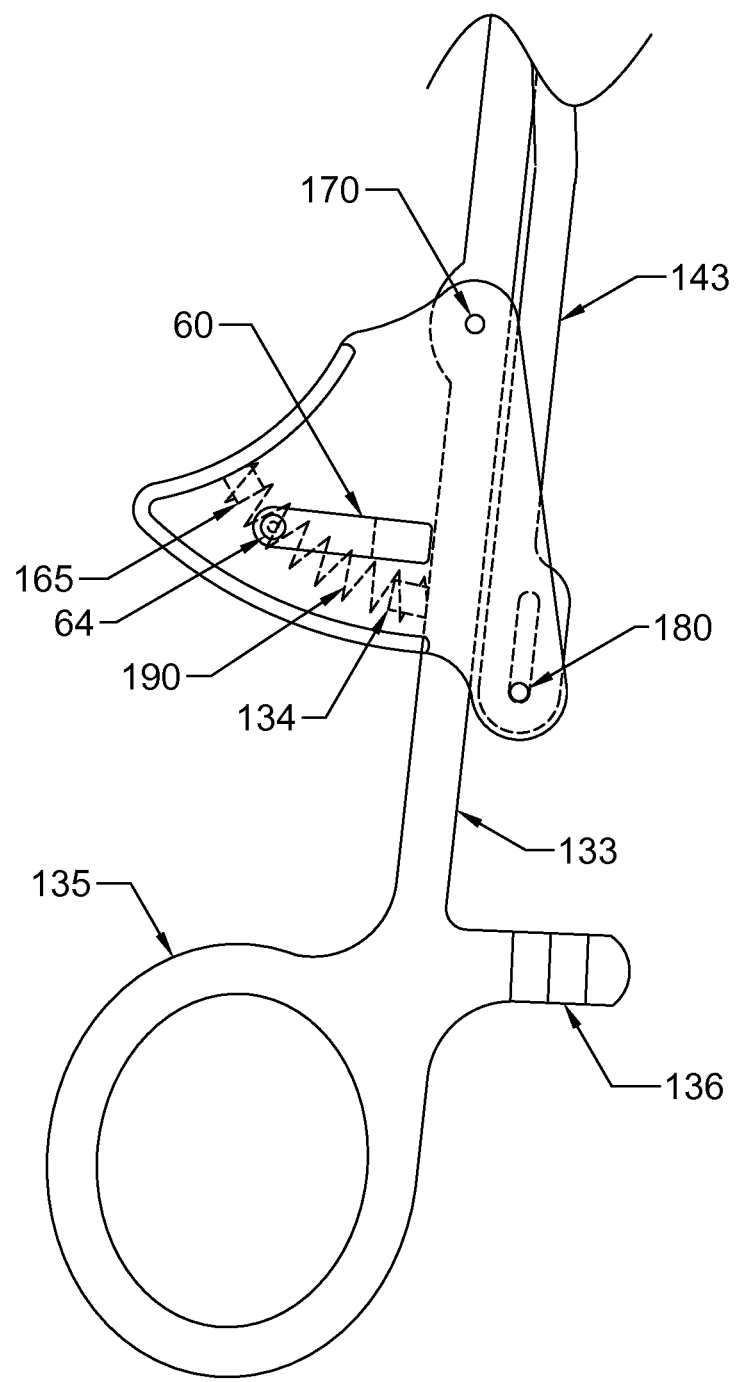
FIG. 39 shows a detail view of the second embodiment trigger mechanism including the internal reset spring.

Surgical instruments including needle drivers come in a wide variety of sizes and lengths. These are advantageous for handling different surgical applications and wound depths from the suturing of skin to the deepest wounds including veterinary applications. A myriad of configurations are required for the enormous scope of tissues being addressed. Needle sizes vary from microscopic to very large and heavy enough to penetrate bone. The current invention is intended for the same wide variety of applications. The geometry of the design can be adjusted to accommodate the wide variety of applications. Specifically, for longer instruments, or for ergonomics, it may be desirable to have a trigger or lever activation of the cutting shear. This embodiment 110 can be accomplished as follows. Similar to the first embodiment the device consists of opposing grasping jaws 21, 131 preferably hinged distally. (FIG. 23) Preferably, finger rings 25, 135 and ratcheting locking teeth 26, 136 are provided proximally. The cutting limb 140 can be similarly attached via the main rotating hinge pin 50. The cutting shear 141 functions in a similar fashion by rotating into position distally into the space between the jaws providing the cutting function. Proximally, however in this embodiment, the cutting limb 140 is preferably activated by the operator depressing a trigger 160 on the convertible limb 130. The trigger 160 is attached to the convertible limb 130 distal to the operator's holding point with a hinge pin 170. The trigger 160 preferably protrudes outward from the convertible limb similar to the activation tab 44 in the first embodiment. The cutting limb 140 preferably courses proximally from the main hinge 50 adjacent to the convertible limb 130. Once clear of the main hinge 50 the cutting limb 140 then courses around parallel to the inside of the shaft 133 of the convertible limb. Then it progresses proximally to the medial portion of the trigger housing, where it is connected via a bearing pin 180 into a longitudinal slot 144 on the cutting limb 140. The trigger housing is formed in a wrap-around shape, able to pivot on the hinge pin 170 on the convertible limb and rotate around the shaft 133 of the convertible limb. It then preferably forms a clevis around the slotted end of the cutting limb 144. Additionally, the trigger housing 160 preferably includes an attached a feedback leaf spring 60. This second embodiment 110 is employed in a similar fashion to the first 10. The instrument 110 functions fully as a standard grasping locking needle driver. (FIG. 25) When cutting function is desired, the operator then depresses the trigger 160, rotating it around the hinge pin 170 on the convertible limb 130. As it is depressed and rotated, the feedback leaf spring head 61 passes over the convertible limb shaft 133 giving the operator tactile feedback of engagement of the cutting device 141. Furthermore, on rotation it compresses the reset spring 190 inside the trigger housing 160 situated between the housing spring post 165 and the convertible limb post 134. (FIG. 39) Upon rotation of the trigger housing the bearing pin 180 applies pressure in the slot 144 of the cutting limb 140, forcing it to rotate into an activated position. The bearing pin 180 slides slightly proximally in the slot of the cutting limb 140 on full rotation. With that motion, the resulting rotation of the cutting limb moves the cutting shear 141 distally into an activated position. (FIG. 26) The operator will simply hold the trigger 160 depressed to use the cutting function. The instrument can then be used repeatedly as desired as a scissor device allowing cutting in the main working area at the distal end of the jaws. (FIG. 27) When cutting function is no longer desired, the cutting shear 141 is deactivated by the operator simply releasing the trigger 160. Once activating pressure is removed from the trigger 160, the reset spring 190 under compression expands forcing rotation of the trigger 160 into its resting position. With rotation of the trigger housing, the bearing pin 180 forces the cutting limb 140 and cutting shear 141 to rotate into an inactivated position, with the pin 180 sliding distally in the provided slot 144. Finally, as the trigger housing returns to its inactive position the feedback leaf spring head 161 passes over the shaft 133 of the convertible limb affording the operator tactile and audible feedback that the cutting device 141 is deactivated. Safe grasping and holding function can then commence. (FIG. 25)

This invention has the advantage of quickly transforming from a grasping to a cutting instrument and back with a simple intuitive motion by the operator. This will save procedural time and add simplicity and safety by utilizing a single instrument for two common and repeated functions.

The operator can now employ the same device used to pass sutures and tie knots to cut the sutures. This eliminates the need for the operator to obtain a different instrument to perform the cutting action. Although in many cases an assistant is available to perform the cutting function, the operating surgeon typically has the best view and occasionally the only clear view of the field to perform the cutting action, particularly when operating under loupe magnification or an operating microscope. These designs also have the significant advantage of a familiar overall shape and function to existing instruments. It is desirable for the addition of the cutting mechanism to be low profile and it does not extend beyond the main driver limbs except for the trigger or activation mechanism. Similarly, on the sides it is low profile and hugs close to the operating jaws, hinge, and limbs, minimizing any potential snagging or interference with operation.

Third Embodiment

Figures 40, 41, 42:
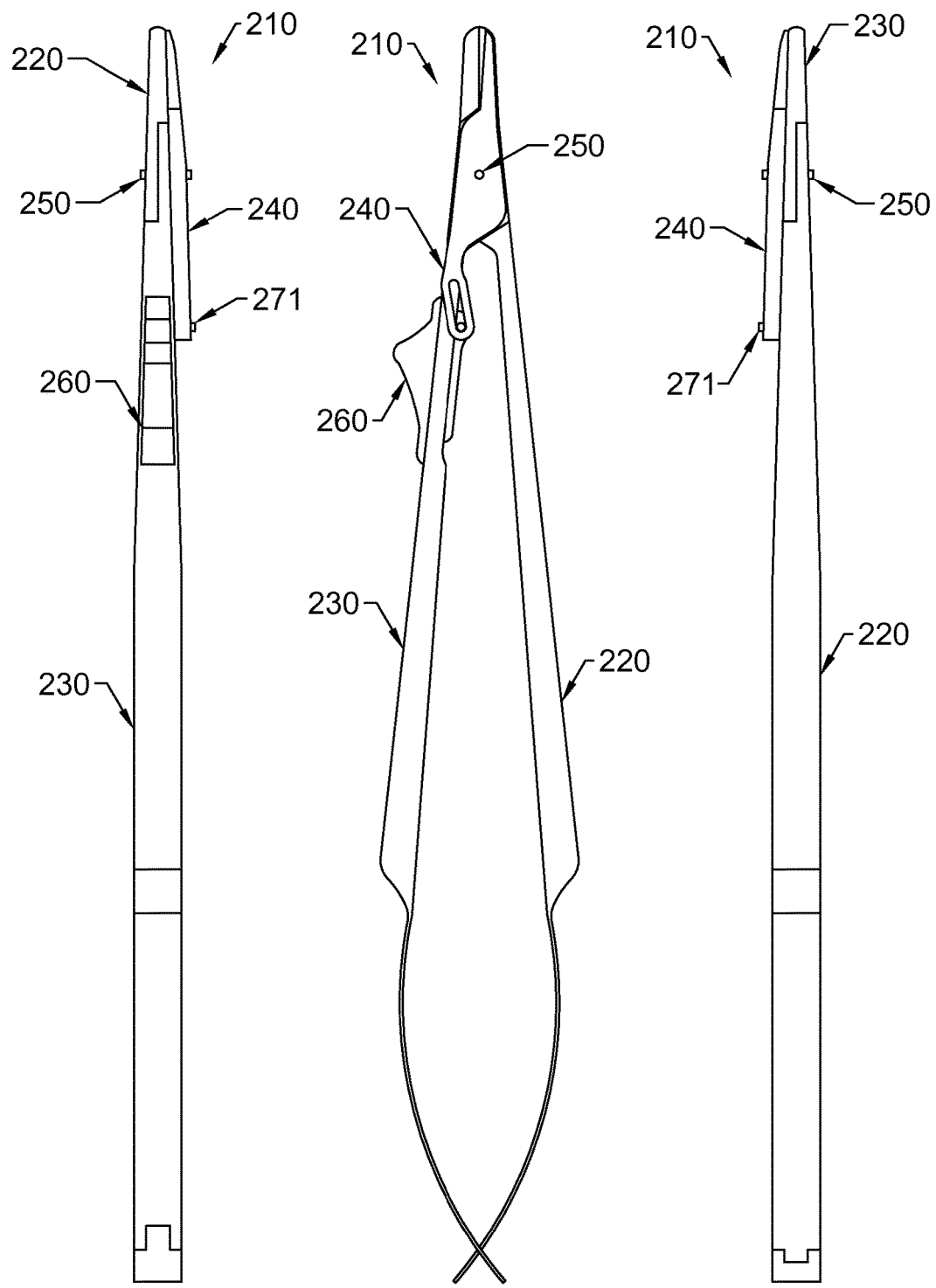
FIG. 40 shows a left side view of the third embodiment microsurgical type combined needle holder with cutting mechanism incorporating a slide activation mechanism.
FIG. 41 shows a front view of the third embodiment with the grasping mechanism closed.
FIG. 42 shows a right side view of the third embodiment.
Figure 43:
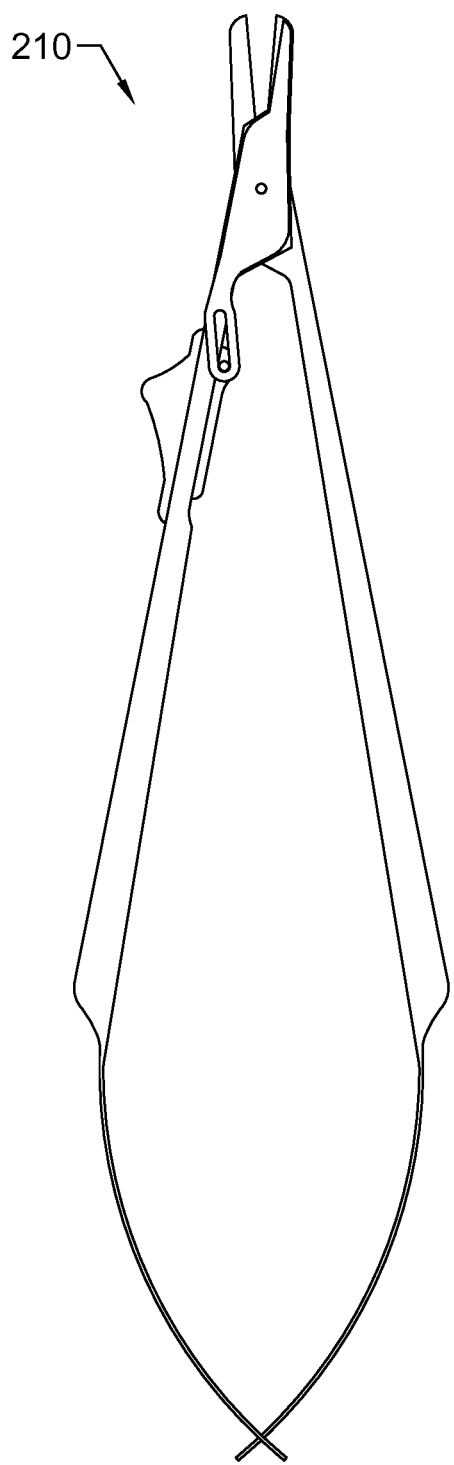
FIG. 43 shows a front view of the third embodiment with the grasping jaws open.
Figure 44:
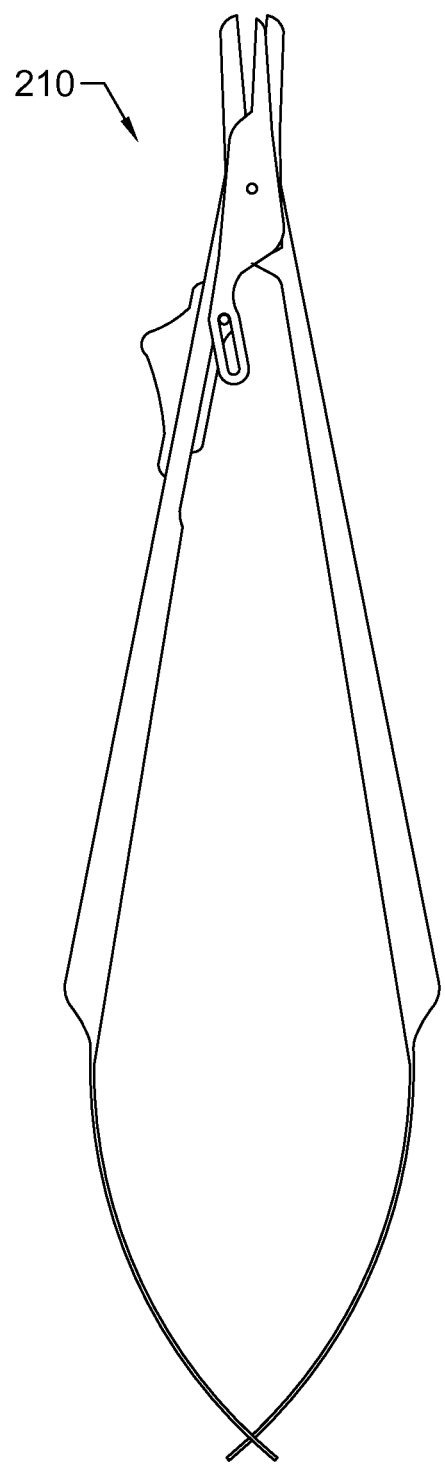
FIG. 44 shows a front view of the third embodiment with the grasping jaws open and the cutting mechanism engaged.
Figure 45:
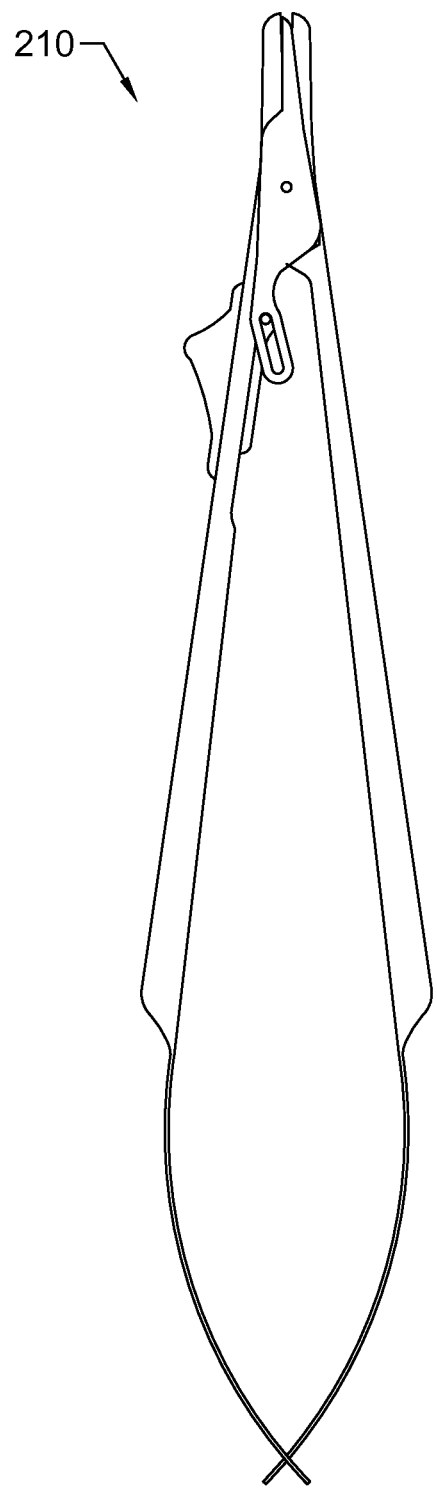
FIG. 45 shows a front view of the third embodiment with the cutting mechanism engaged and the device cutting distally.
Figure 46:
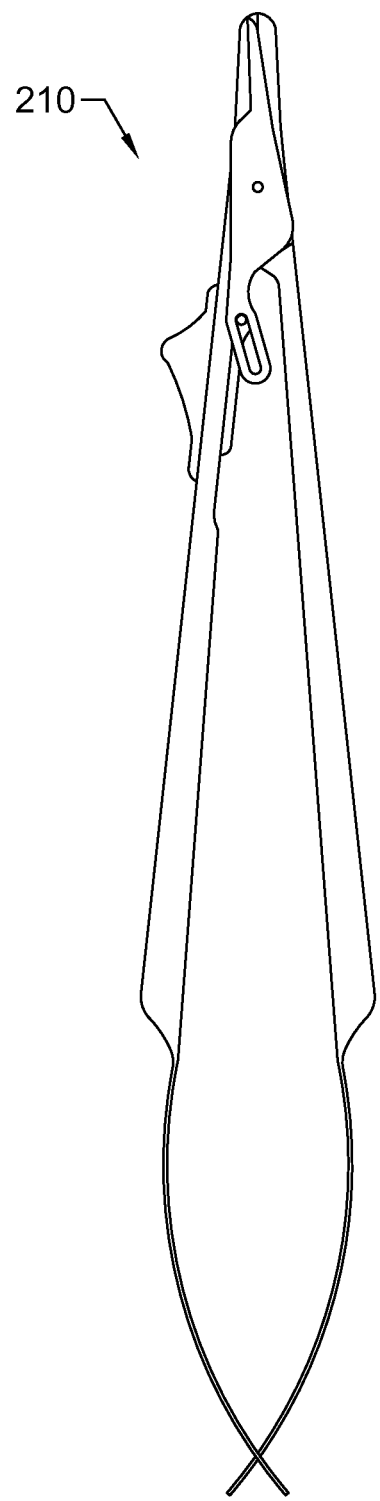
FIG. 46 shows a front view of the third embodiment with cutting mechanism engaged and the jaws closed.
Figures 47, 48, 49:
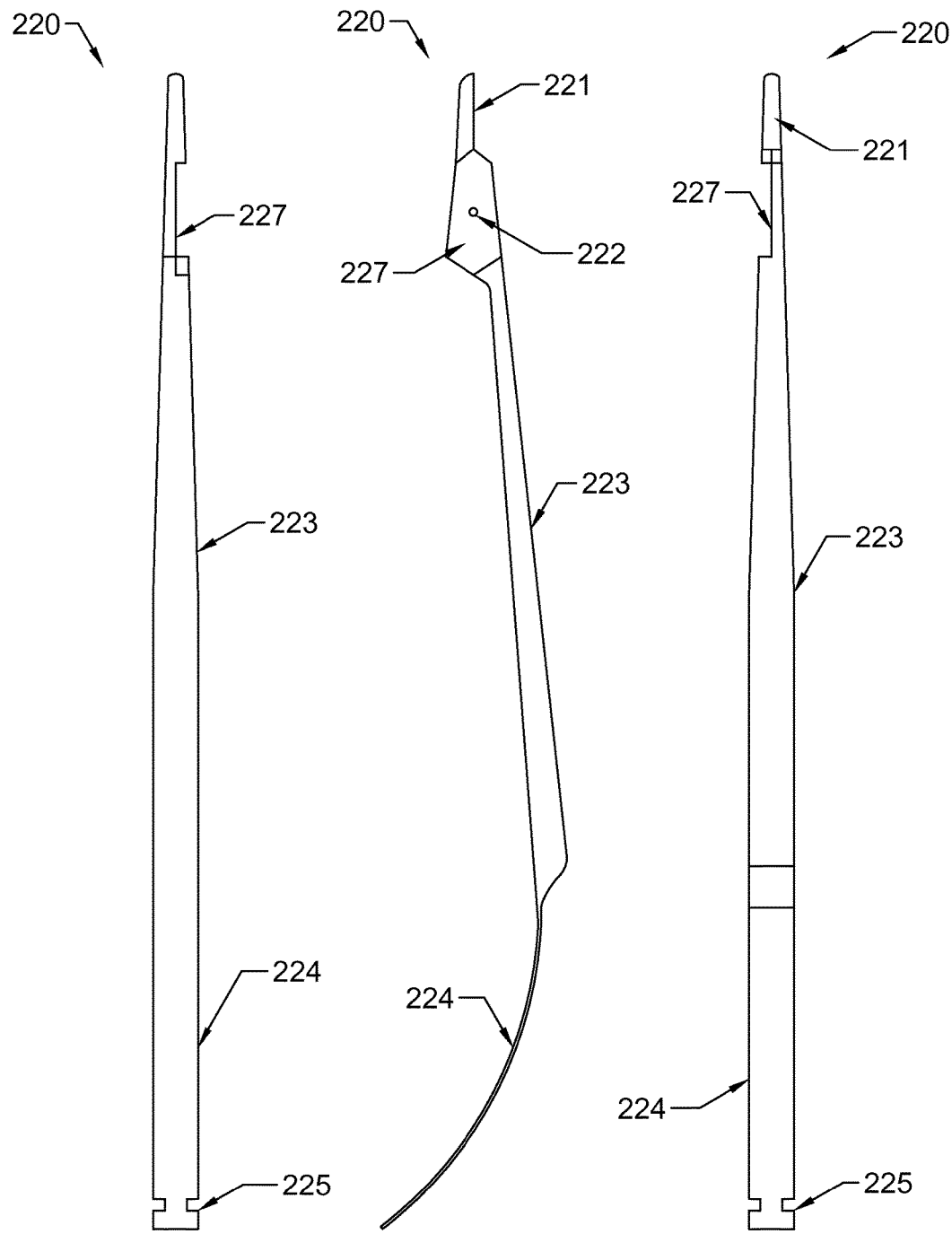
FIG. 47 shows a left side view of the third and fourth embodiment standard grasping limb.
FIG. 48 shows a front view of the third and fourth embodiment standard grasping limb.
FIG. 49 shows a right side view of the third and fourth embodiment standard grasping limb.
Figure 50:
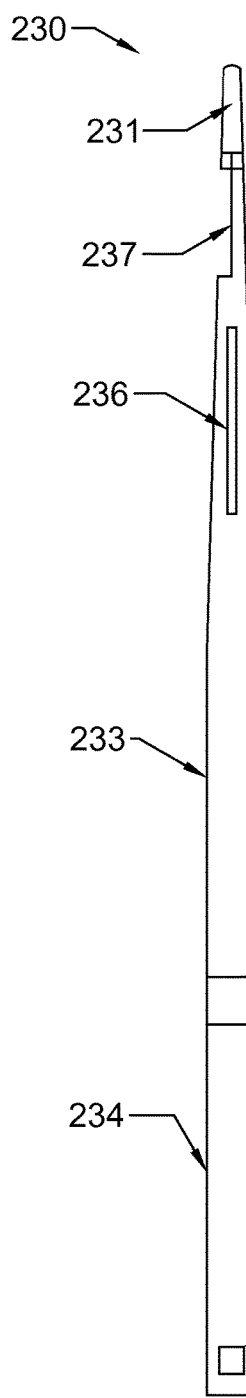
FIG. 50 shows a left side view of the third embodiment convertible grasping limb.
Figure 51:
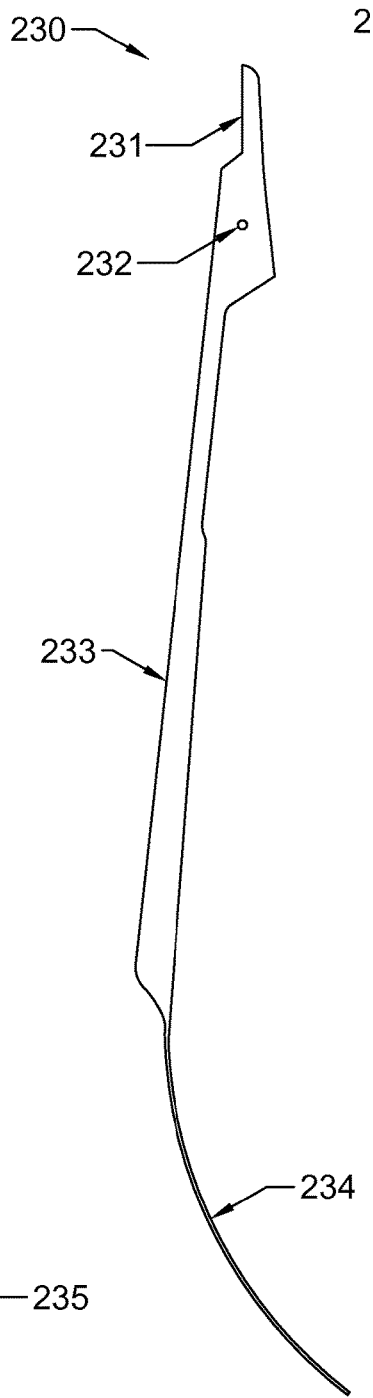
FIG. 51 shows a front view of the third embodiment convertible grasping limb.
Figure 52:
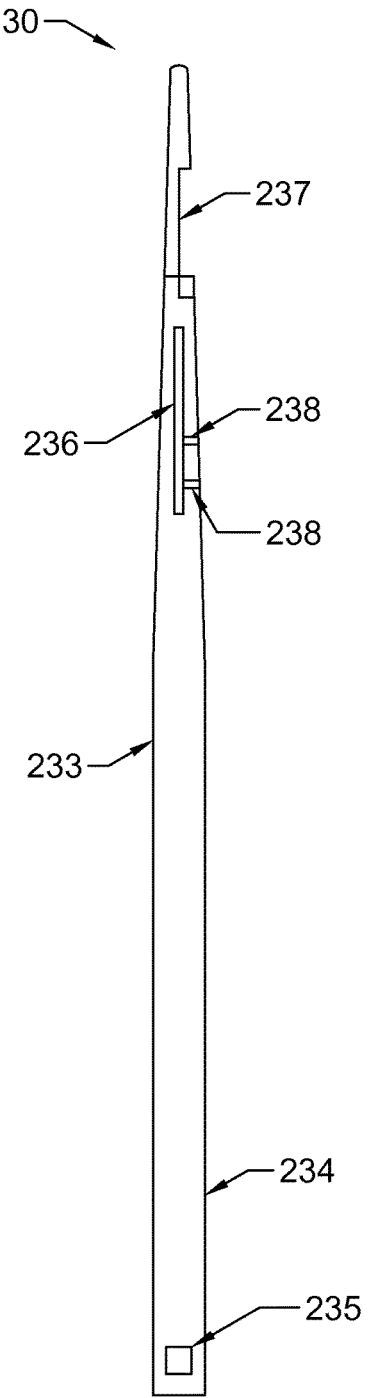
FIG. 52 shows a right side view of the third embodiment convertible grasping limb.

The same invention can be applied to microsurgical needle holders. The grasping jaws and cutting shear or shears can be sized and mounted onto microsurgical needle holders in the same fashion. (FIG. 41) The distal end preferably incorporates the new design of grasping and cutting while proximally the shape typically has more parallel limbs. The operator uses the grasping functions preferably by squeezing the limbs 220, 230 of the device between the fingers and thumb thus closing the working jaws. (FIG. 43) Typically there is a return spring 224, 234 on the limbs 220, 230 either squeezing force. For the new invention, the cutting shear 241 can be applied, typically rotating about the same main hinge 250 of the instrument 210. For activation it may be desirable to have a slide mechanism for easy use by the operator to engage the cutting function. This can be accomplished by having a slide 270 affixed to the convertible limb 230 of the instrument just proximal to the articulation of the device. The slide 270 may penetrate the convertible limb 230 to have a portion lying adjacent to the limb on the inside and one portion one the outside with an ergonomically shaped area 260 for the operator to activate it. The slide mechanism 270 can then be attached to the end of the cutting limb 240 proximal to the main hinge 250 with a sliding pin 271. The sliding pin 271 can be arranged so as to penetrate and attach to an oblique slot 244 in the cutting limb 240. The instrument can be used in a typical fashion for holding and passing surgical needles and tying surgical knots. When the operator desires cutting action the index finger is then used to slide the mechanism distally. That then forces the sliding pin 271 toward the main hinge 250 of the device in the oblique slot 244 of the cutting limb 240. As the pin 271 slides toward the hinge, it applies pressure in the oblique slot causing the cutting limb 240 to rotate. The rotation of the cutting limb 240 engages the cutting shear 241 distally into a position of action lying within the working jaws of the instrument 210. (FIG. 44) The surgical instrument 210 is then effectively converted from a grasping device to a cutting device. The operator can then simply squeeze the main limbs of the instrument, whereby the cutting shear 241 will cut against the opposite grasping jaw 221 essentially using it in the same fashion as scissors. (FIG. 45) Once the cutting actions are complete the device is easily converted back to its grasping function by moving the slide toward the operator. The sliding pin 271 will then force the cutting limb 240 to rotate into an inactive position by applying force in the slot 244. The rotation of the limb 240 then rotates the cutting shear 241 distally into its resting position typically next to one of the working jaws. The instrument can then be employed once again for grasping needles, suture or other materials. (FIG. 43) When deactivated, the cutting shear rests in a protected position alongside the convertible jaw, protecting it from cutting until reactivated. Additionally it may be advantageous to have a leaf spring 280 slide into a detent 238 or other mechanism whereby when the slide is employed to activate and/or deactivate the cutting mechanism, a positive tactile or audible feedback such as a "click" is afforded to the operator. It is usually desirable to form microsurgery instruments such as this from titanium or other non-magnetic material so as to avoid any magnetic effects on the microsurgical needles.

This instrument 210 will allow efficient grasping and cutting actions with a microsurgical styled instrument. Dual functions of grasping, needle driving and tying along with the ability to cut suture safely and efficiently is particularly advantageous for microsurgery where the field of vision of the operator is limited to that of the microscope and changing instruments can be particularly intrusive to the procedure.

Fourth Embodiment

Figures 68, 69, 70:
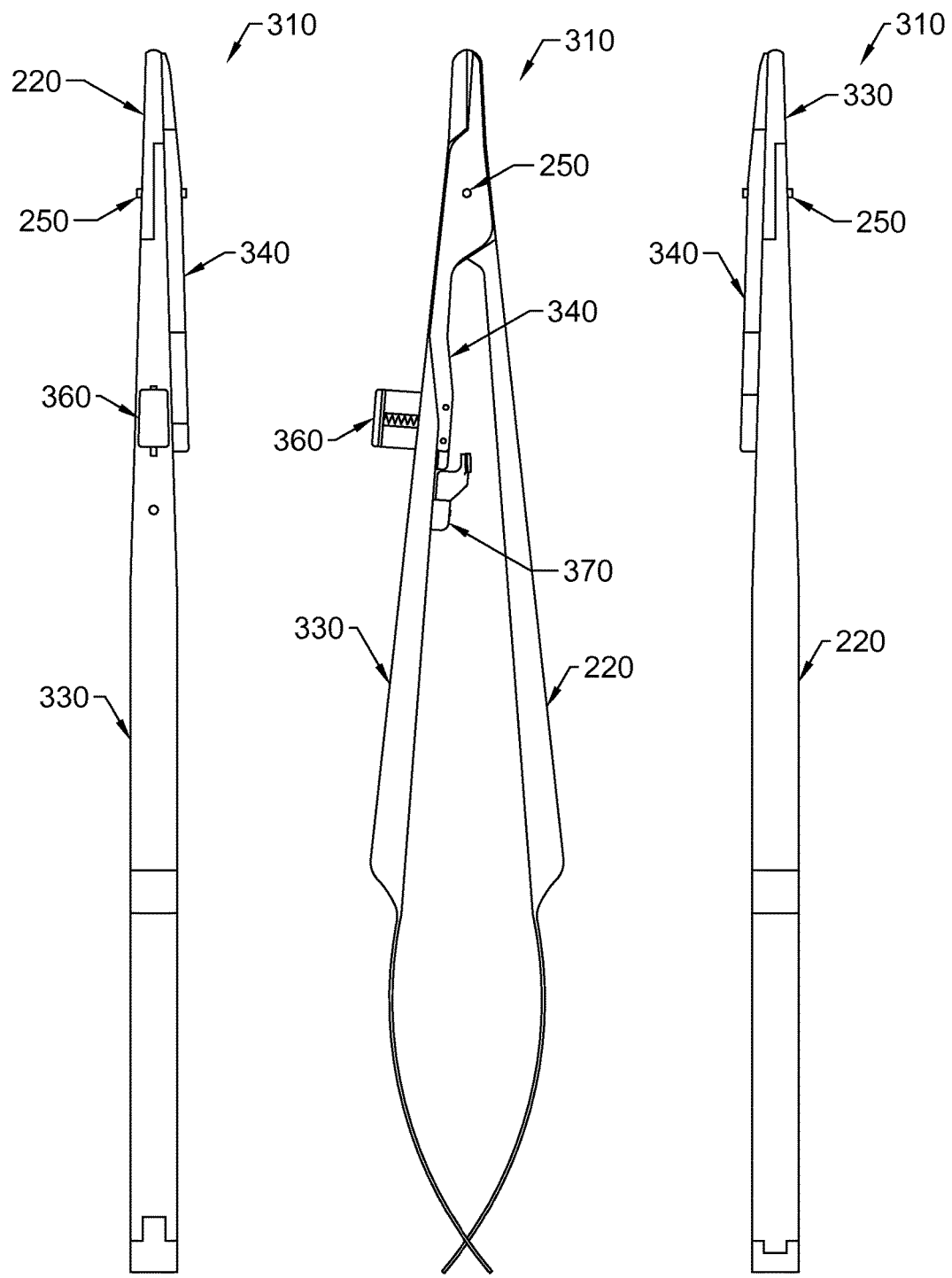
FIG. 68 shows a left side view of the fourth embodiment microsurgical type combined needle holder with cutting mechanism featuring push button activation.
FIG. 69 shows a front view of the fourth embodiment with the grasping mechanism closed.
FIG. 70 shows a right side view of the fourth embodiment.
Figure 71:
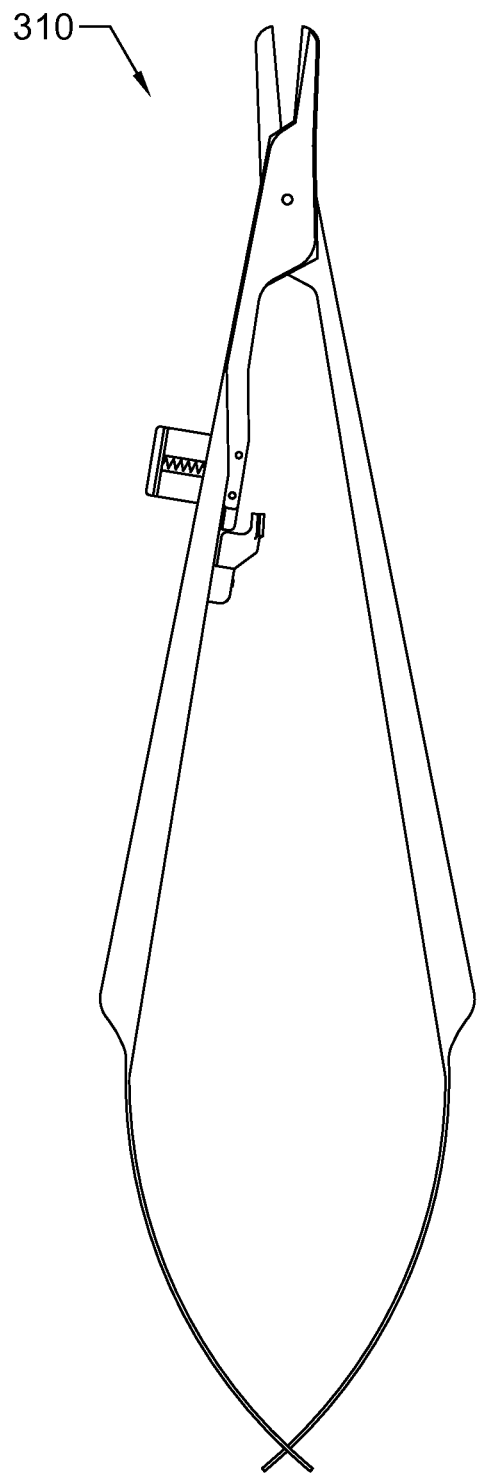
FIG. 71 shows a front view of the fourth embodiment with the grasping jaws open.
Figure 72:
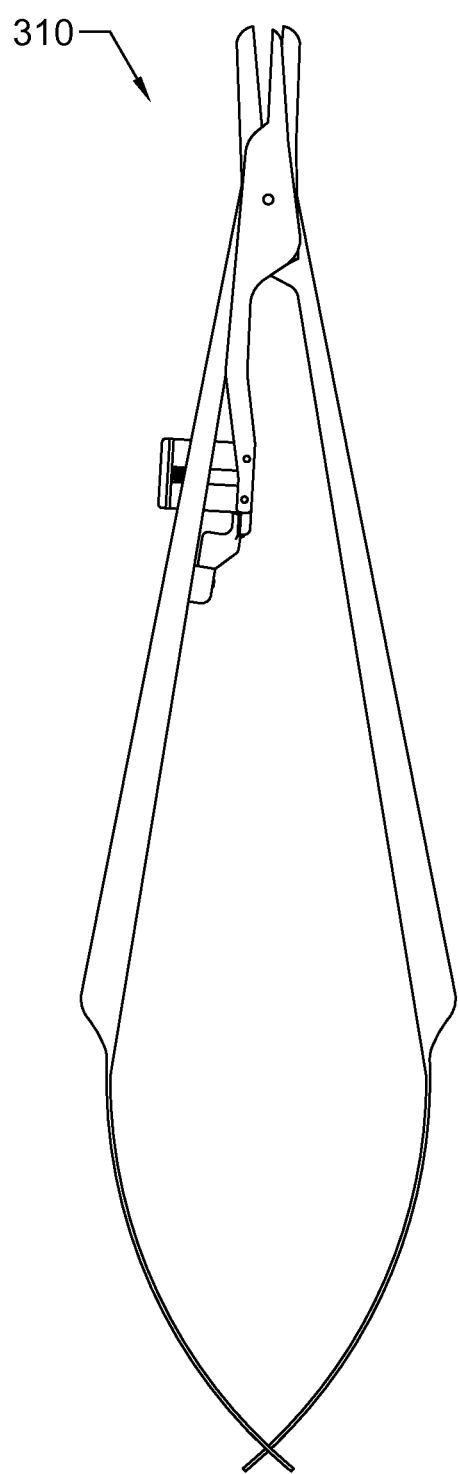
FIG. 72 shows a front view of the fourth embodiment with the grasping jaws open and the cutting mechanism engaged.
Figure 73:
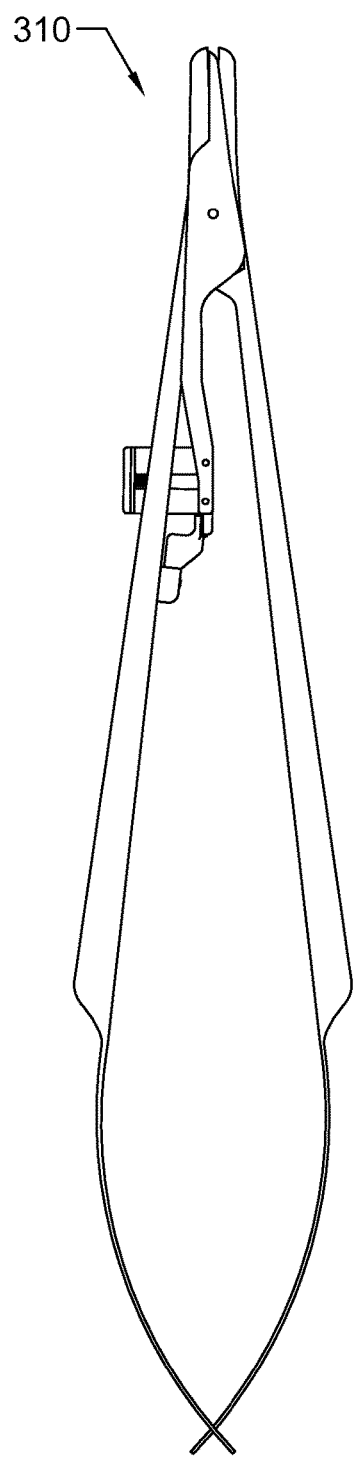
FIG. 73 shows a front view of the fourth embodiment with the cutting mechanism engaged and the device cutting distally.
Figure 74:
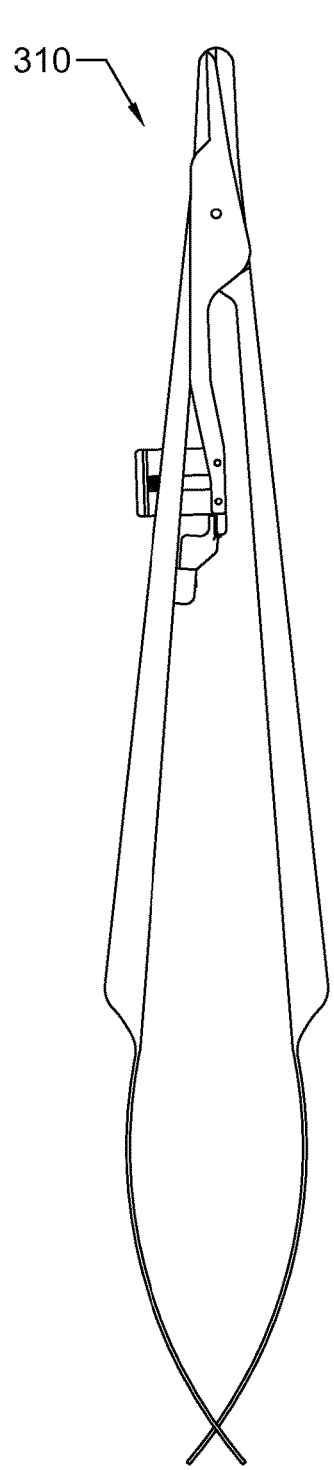
FIG. 74 shows a front view of the fourth embodiment with the cutting mechanism engaged and the jaws closed.
Figure 75:
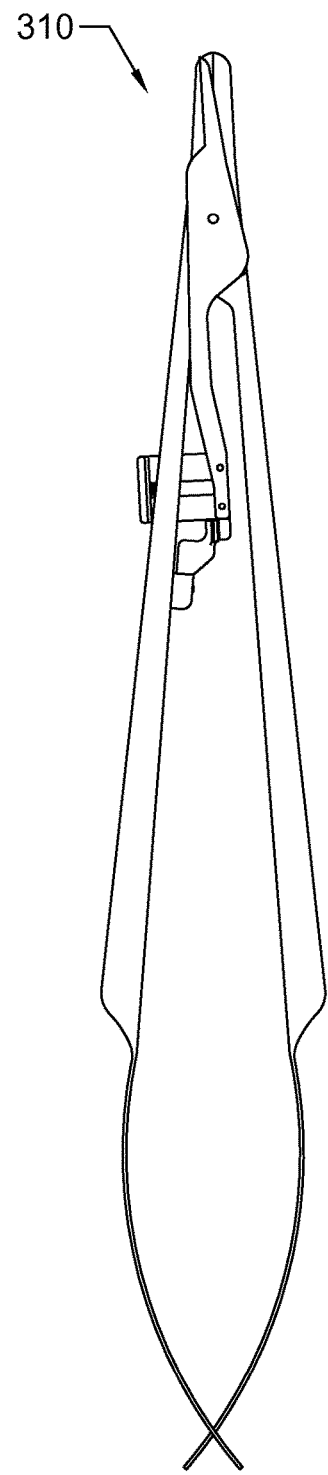
FIG. 75 shows a front view of the fourth embodiment with the cutting mechanism engaged, the jaws closed, and the activation button fully depressed to bypass the latch mechanism allowing automatic return of the cutting shear.
Figure 76:
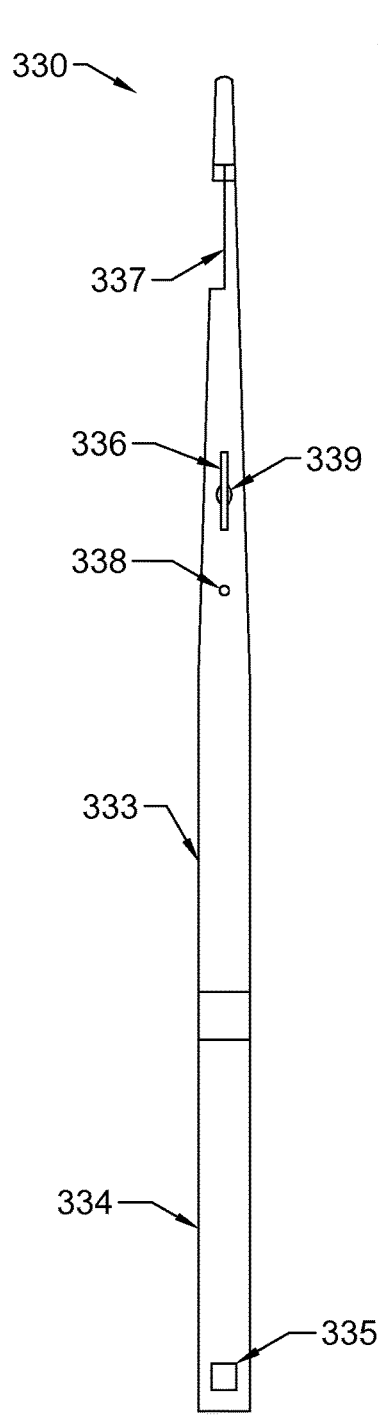
FIG. 76 shows a left side view of the fourth embodiment convertible grasping limb.
Figure 77:
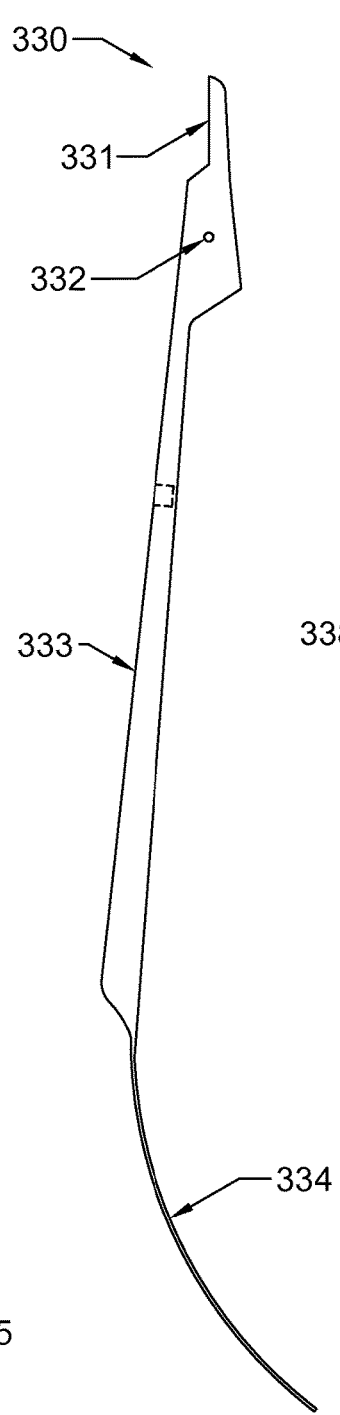
FIG. 77 shows a front view of the fourth embodiment convertible grasping limb.
Figure 78:
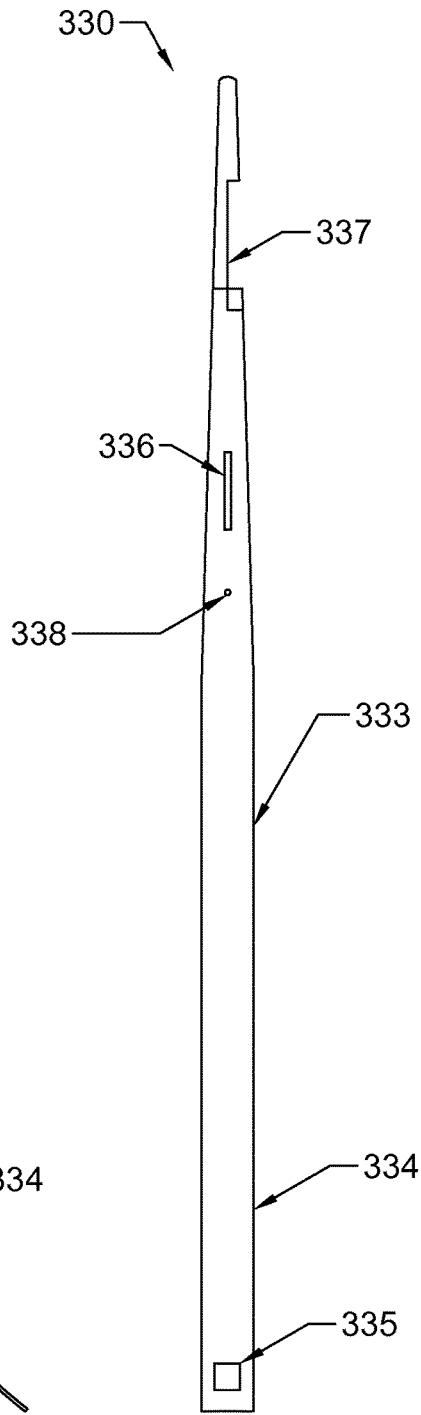
FIG. 78 shows a right side view of the fourth embodiment convertible grasping limb.
Figures 79, 80, 81, 82:
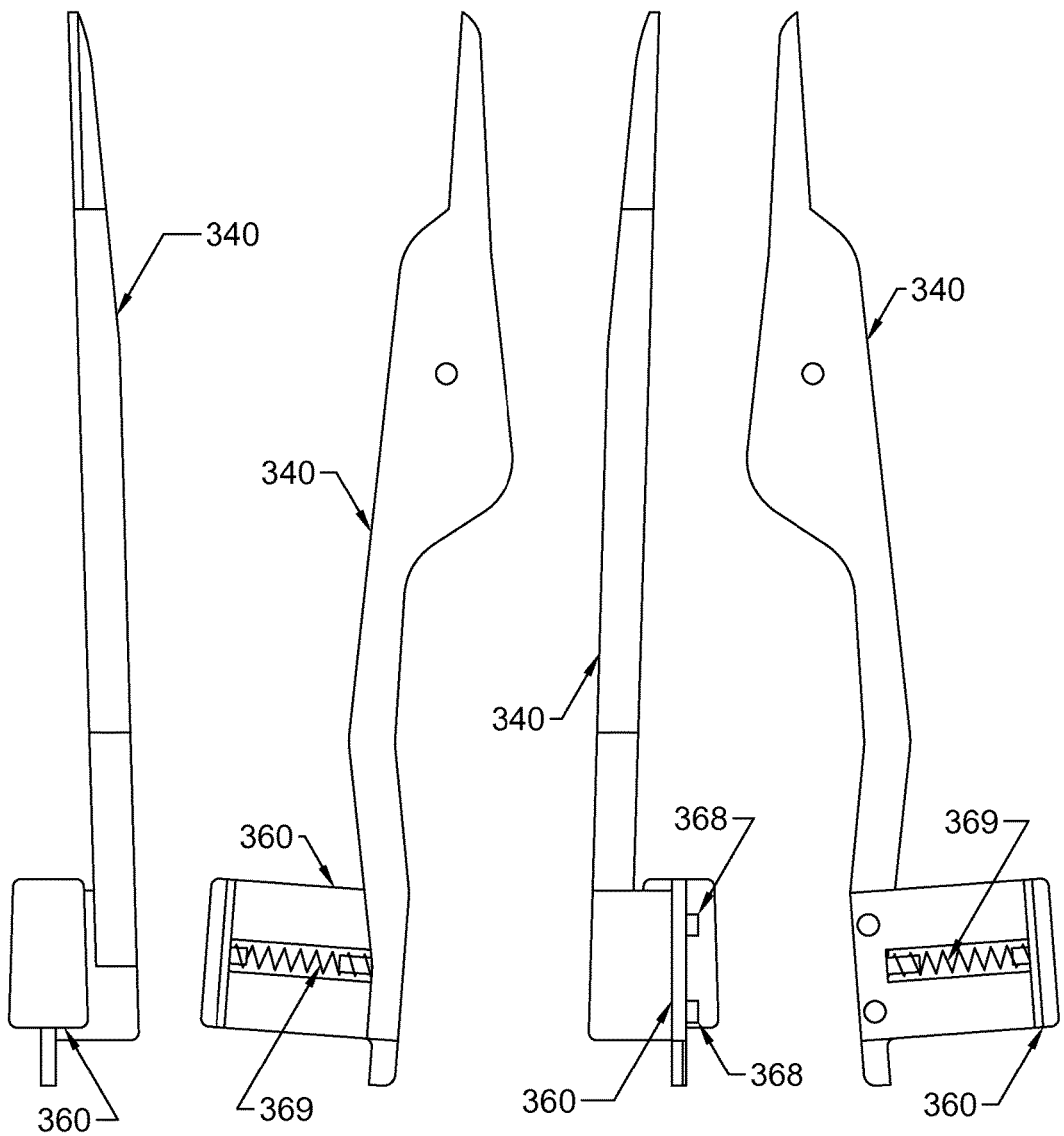
FIG. 79 shows a left side view of the fourth embodiment cutting limb and push button activation assembly.
FIG. 80 shows a front view of the fourth embodiment cutting limb and push button activation assembly.
FIG. 81 shows a right side view of the fourth embodiment cutting limb and push button activation assembly.
FIG. 82 shows a back view of the fourth embodiment cutting limb and push button activation assembly.
Figures 83, 84, 85, 86:
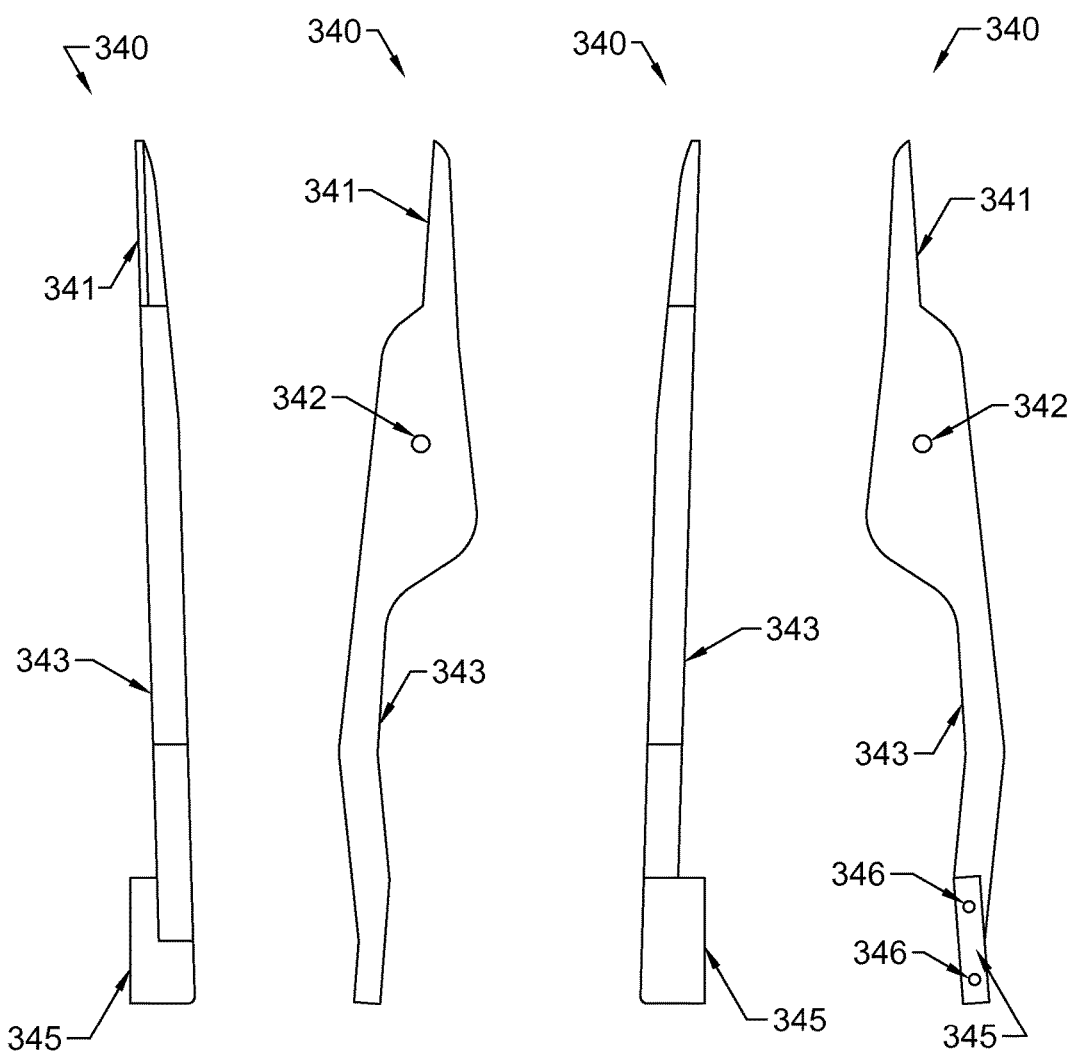
FIG. 83 shows a left side view of the fourth embodiment cutting limb.
FIG. 84 shows a front view of the fourth embodiment cutting limb.
FIG. 85 shows a right side view of the fourth embodiment cutting limb.
FIG. 86 shows a back view of the fourth embodiment cutting limb.
Figure 93:
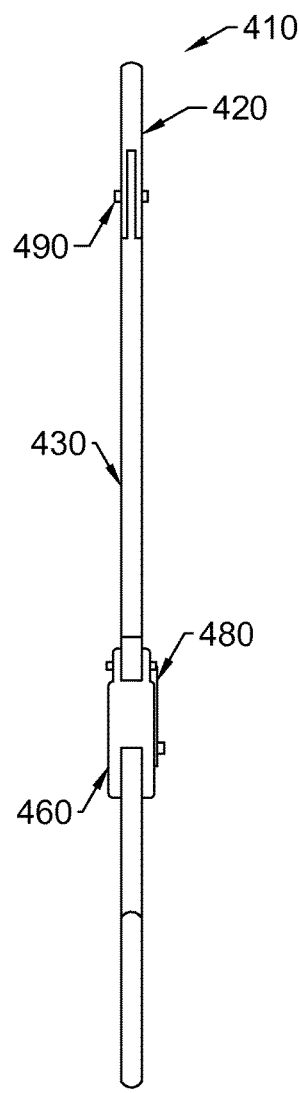
FIG. 93 shows a left side view of the fifth embodiment combined needle holder with cutting blade located within the grasping jaw.

Yet another embodiment may be desirable for activation of the cutting shear with a push-on push-off mechanism. This apparatus 310 consists of a similar microsurgical type needle holder to the previous embodiment 210. The two grasping jaws 221, 331 are preferably hinged distally and attached to semi-parallel limbs proximally. The cutting limb 340 may be hinged on the same axis. Proximally, the cutting limb 340 is connected to a push button device 360 in the shaft 333 of the convertible grasping limb 330. (FIG. 69) The instrument is preferably used in a typical fashion for grasping functions by squeezing and releasing the main limbs 220, 330 which also preferably have a return spring 224, 334. (FIG. 71) In order to activate the cutting function, the operator simply presses the activation button 360 squeezing it in the same direction to close the limbs. By pressing the mechanism, the cutting limb 340 and therefore the cutting shear 341 are rotated about the hinge 250. The cutting shear 341 is activated into position past the convertible grasping jaw 331 and then allows cutting distally in the main working jaws of the instrument. (FIG. 72) The cutting action takes place in the same area of the jaws as was used for grasping and with the same general motion and plane of action as would be employed for similar scissor instruments. The push button activation mechanism 360 preferably incorporates a blade 362 to catch on a bypass spring latch 370 that locks the cutting limb into an activated position, functioning similarly to locking microsurgical instruments. As it is engaged, the bypass latch 370 preferably has a positive click for audible and tactile feedback for activation of the cutting action. Once the blade 362 is locked into the latch catch 371, the attached cutting limb 340 is held firmly into its activated position allowing cutting and resisting rotation by the latch. (FIG. 73) When grasping operation is again desired, the cutting mechanism is deactivated, preferably in the same manner. Preferably the operator presses the activation push button 360 further to cause the blade 362 to release from the bypass latch catch 371. As the cutting limb 340 and button 360 are rotated further, the blade disengages 362 from the latch 370 preferably with an audible click. (FIG. 75) Now that it is released the pressure can be lifted from the activation button. A reset spring 369 inside the button mechanism preferably will automatically return the cutting limb 340 and shear 341 back to an inactive position. The instrument 310 is once again ready to perform safe grasping functions.

This embodiment 310 provides a very fast and natural action to convert the needle holders into a cutting device. All that is required for operation is a press with the index finger of the operator on a push mechanism. This mechanism is located near the natural position for the finger with use of the device. This will allow for more expeditious use of the single instrument without the need to swap instruments to perform cutting.

Fifth Embodiment

It may be desirable for the design to incorporate the cutting blade internally within at least one of the grasping jaws. This allows for a symmetrical profile to the working end of the device. In use the operator activates the cutting mechanism, causing the cutting blade to advance out of the grasping jaw. The blade then lies within the jaws for use in dividing material in the main working jaws grasping area. When grasping is desired the cutting blade is then retracted back into the grasping jaw, converting it back into a safe grasping device. It may be desirable for the cutting blade assembly to be constructed in such a way that the assembly or just the distal blade is removable and replaceable by the operator or assistant. Additionally, the blade may be fabricated of material allowing sharpening and repeat use or fabricated of material intended for disposal following single use. Furthermore, the design could be configured such that the instrument uses commonly available disposable blades for its cutting action. This design is also applicable to endoscopic, laparoscopic, arthroscopic, or robotic instruments. The grasping jaw with internal cutting blade is preferably fitted onto the end of the minimally invasive instrument. It is then employed by the operator utilizing controls on the proximal end of the instrument or robotic controls. The internal blade in at least one of the jaws then slides, rotates or otherwise advances into a cutting position within the jaws. Cutting actions then take place in the same area of the jaws as was used for grasping. The cutting blade is deactivated in a similar fashion and the instrument returns to grasping functions. Thus, the operator is able to simply select and apply either grasping or cutting functions in the same working area of the new device.

Figure 94:
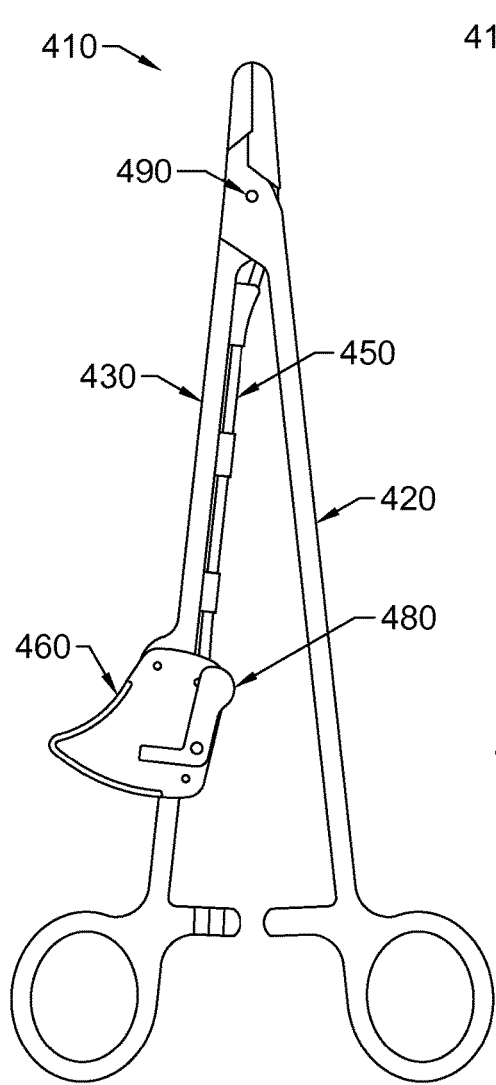
FIG. 94 shows a front view of the fifth embodiment with the grasping jaws closed.
Figure 95:
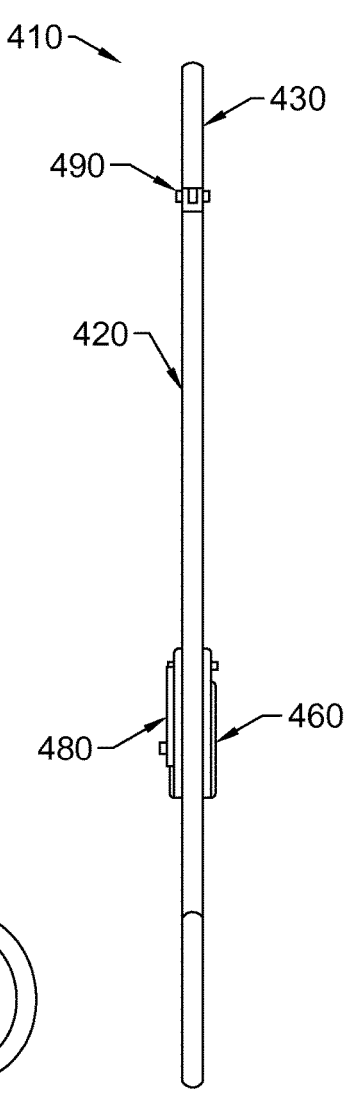
FIG. 95 shows a right side view of the fifth embodiment.
Figure 114:
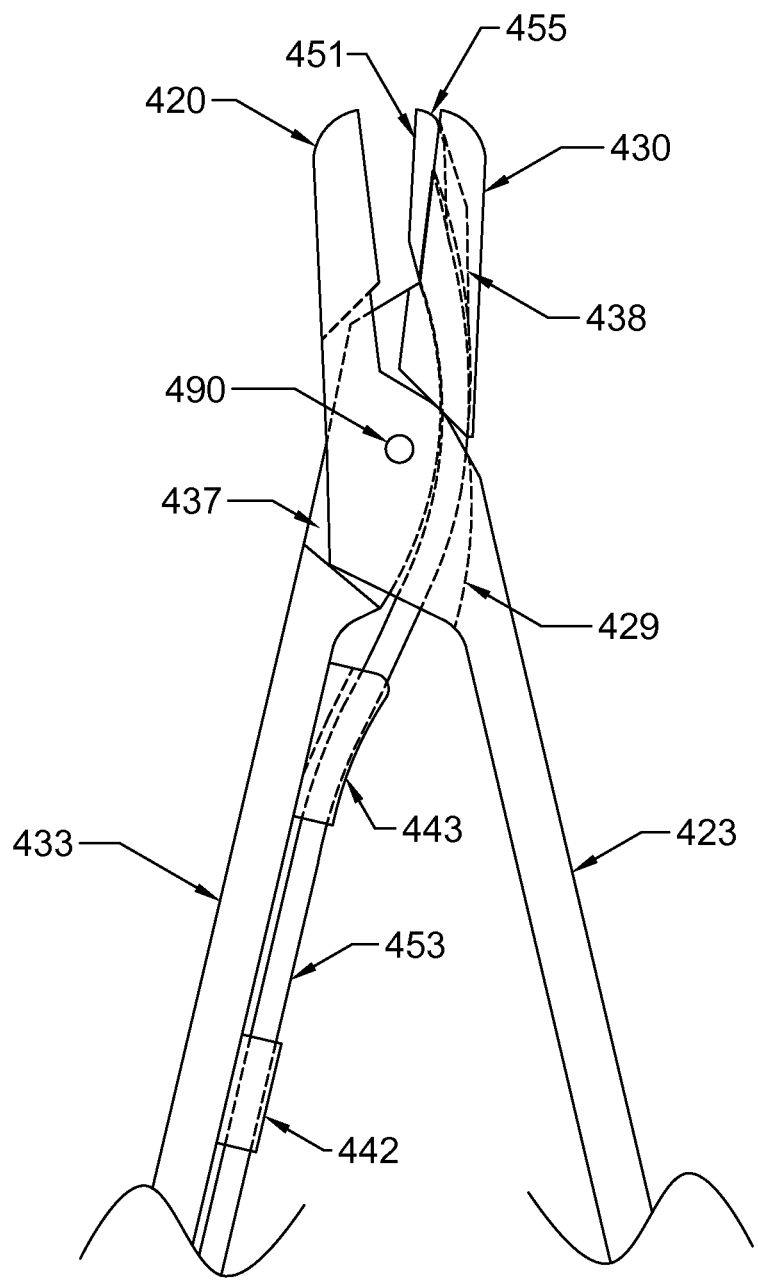
FIG. 114 shows a detail view of the fifth embodiment action with the jaws open and the cutting blade deployed.

An embodiment designed for use as a hand held needle holder is presented as follows: The device 410 is constructed with two grasping jaws distally connected by a main hinge 490. (FIG. 94) The proximal limbs are preferably used by the operator in a standard fashion to open and close the grasping jaws. If desired, finger rings 425, 435 and ratcheting locking teeth 426, 436 are provided. In this embodiment, one of the jaws 431 is preferably convertible to a cutting apparatus and contains an internally mounted cutting blade 451. The other standard jaw 421 is preferably used for grasping as well as a stable surface for cutting against. The cutting blade 451 is preferably configured on the end of the cutting limb 450 which preferably extends from within the convertible jaw 431 then around the main hinge 490 of the device 410 to lie adjacent to the shaft 433 of the convertible limb proximally. (FIG. 114) The cutting limb 450 then preferably passes through guides 441, 442, 443 as needed preferably keeping it straight and close to the convertible limb. In this embodiment, the cutting limb is preferably formed of a semi-rigid material, such as stainless spring steel, to allow enough flexibility to pass around the main hinge and course through the guides on the convertible limb.

Figure 101:
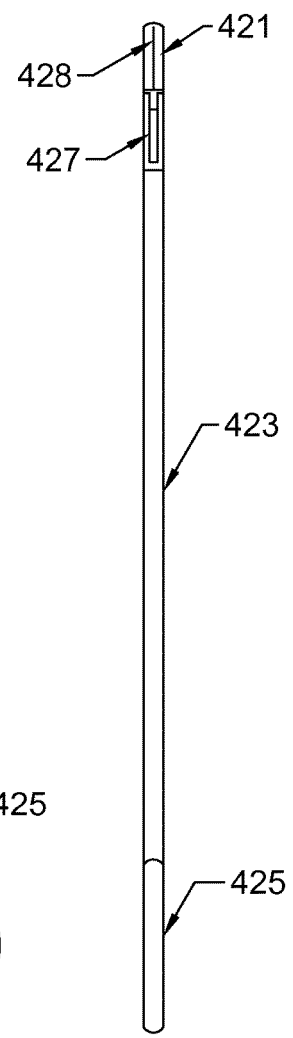
FIG. 101 shows a right side view of the fifth embodiment standard grasping limb.
Figures 105, 106, 107:
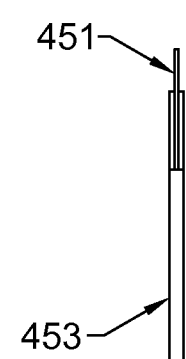
FIG. 105 shows a left side view of the fifth embodiment cutting limb and blade.
FIG. 106 shows a front view of the fifth embodiment cutting limb and blade.
FIG. 107 shows a right side view of the fifth embodiment cutting limb and blade.
Figure 115:
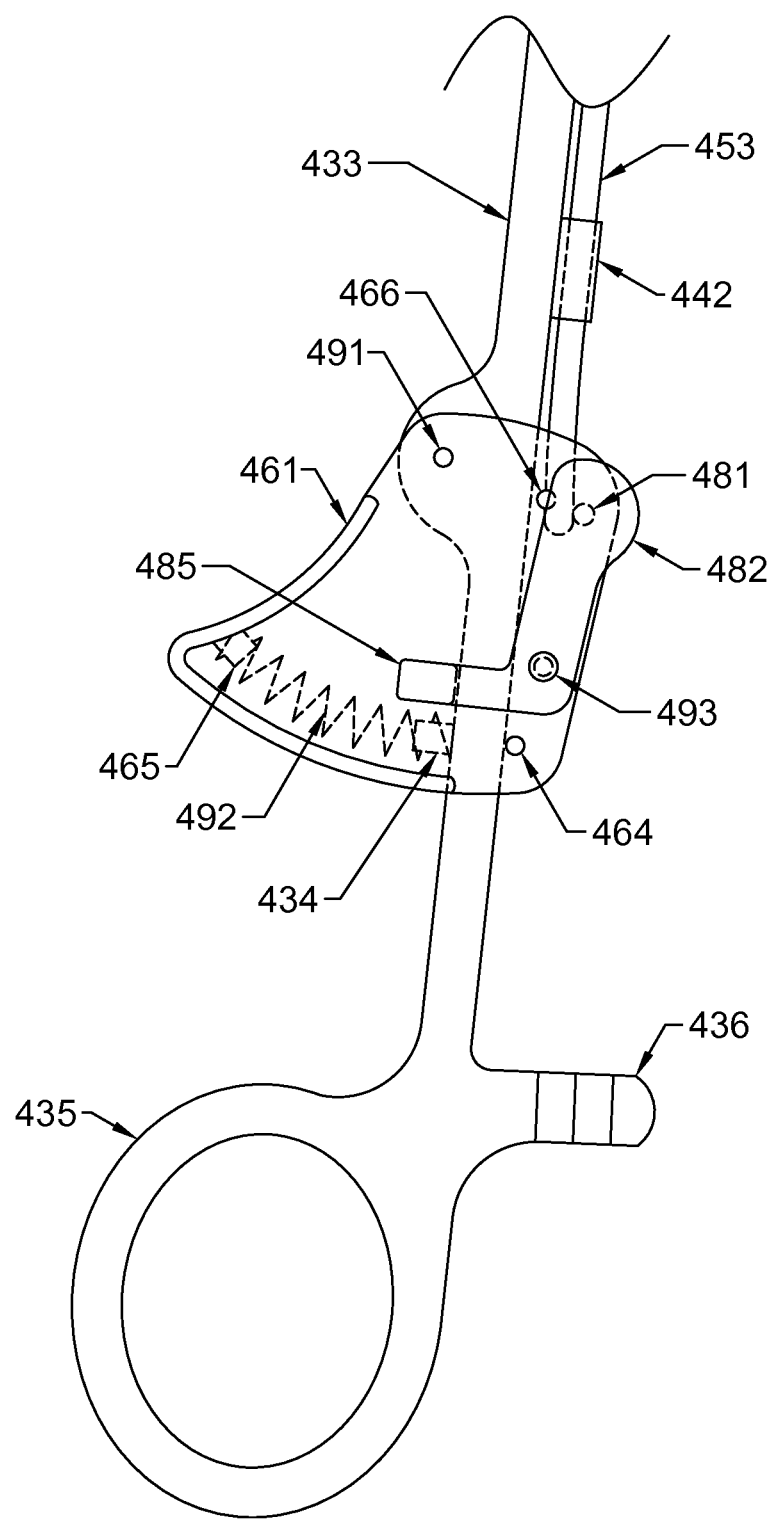
FIG. 115 shows a detail view of the fifth embodiment trigger mechanism and cutting limb attachment.

Proximally, on the convertible limb a trigger mechanism 460 is preferably provided similar to that described in the second embodiment 110. (FIG. 115) The trigger mechanism 460 is preferably hinged on the convertible limb 430 via a pin 491 and preferably has an area provided for the operator to depress 461. The trigger housing preferably wraps around the convertible limb shaft 433 where it preferably attaches to the proximal end of the cutting limb 450. Attachment for the cutting limb is provided in this design preferably with a semicircular recess 454 near the end of the cutting limb 450. The recess 454 is preferably fitted against a bearing pin 466 on the trigger housing and a second retaining pin 481 is preferably seated on the opposite side of the recess in the cutting limb 456. This affords a secure attachment of the cutting limb 450 to the trigger mechanism 460, allowing for the necessary rotation of the mechanism in use. When the trigger mechanism 460 is rotated by the operator, preferably the attached cutting limb 450 is advanced or retracted by the motion. The cutting limb retaining pin 481 is preferably appended to a combined retaining pin and feedback spring 480 preferably with a finger tab 482 on the side of the trigger housing 463 allowing ease of removal. (FIG. 112) The distal end of the cutting limb 450 preferably lies within a channel 438 in the convertible grasping jaw. The channel 438 guides the cutting limb and attached blade 451 as it is advanced and retracted by the operator. (FIG. 114) The channel 438 is preferably configured in such a manner that advancement of the cutting limb directs the cutting blade 451 from within the convertible grasping jaw 431 to lie within working area of the jaws. While the blade 451 is advanced, closing the instrument jaws preferably causes the cutting blade 451 to cut against the standard grasping jaw 421. A fine recess 428 in the standard grasping jaw may be provided to seat the cutting blade 451 assisting in cutting and maintaining its proper shape. (FIG. 101) It may be desirable to provide an insert of somewhat softer material within this recess to further maintain the sharpness of the blade. The cutting blade 451 is preferably thinner than the attached cutting limb 450 and preferably incorporates a fin 455 distally, which seats within a corresponding channel 438 in the convertible grasping jaw 431. This may be provided to enhance lateral stability of the blade while cutting.

Figures 96, 97:
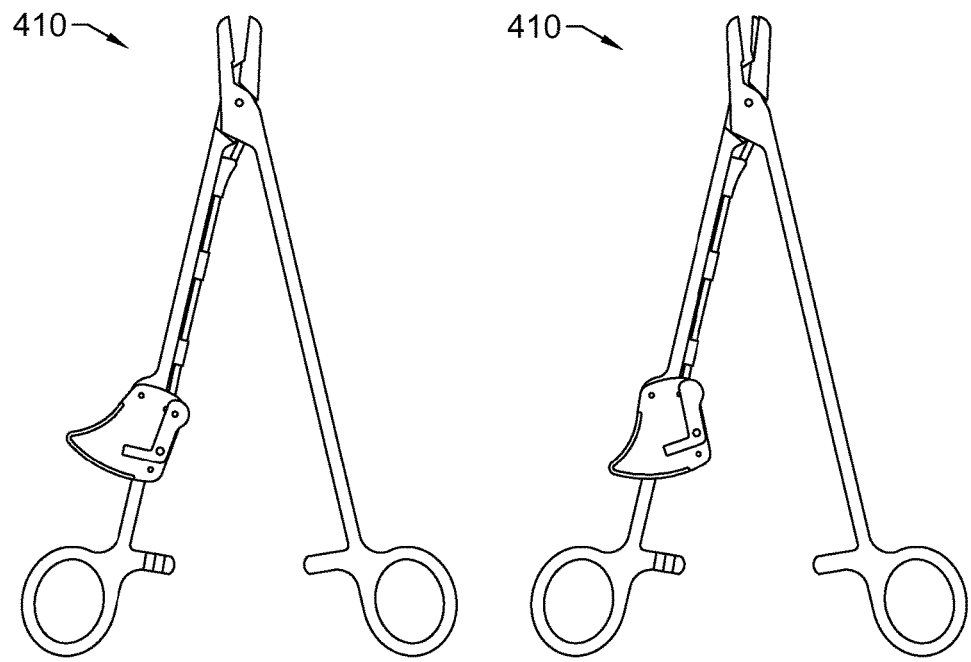
FIG. 96 shows a front view of the fifth embodiment with the grasping jaws open.
FIG. 97 shows a front view of the fifth embodiment with the trigger activated and the integrated cutting blade deployed.
Figure 98:
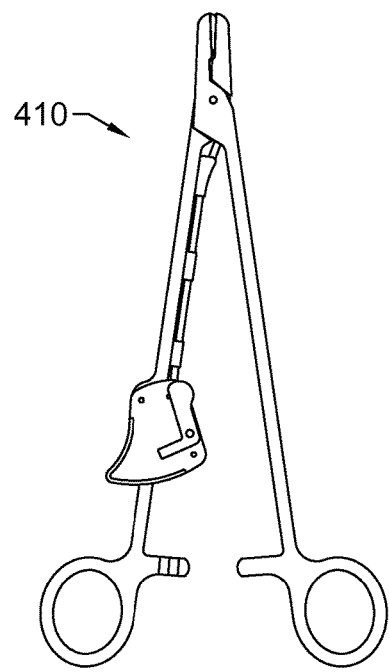
FIG. 98 shows a front view of the fifth embodiment in the cutting position with the cutting blade deployed.
Figure 99:
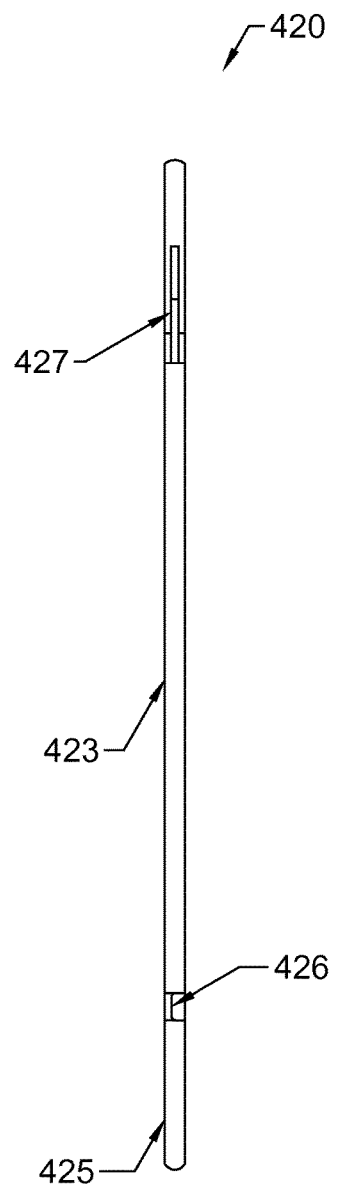
FIG. 99 shows a left side view of the fifth embodiment standard grasping limb.
Figure 100:
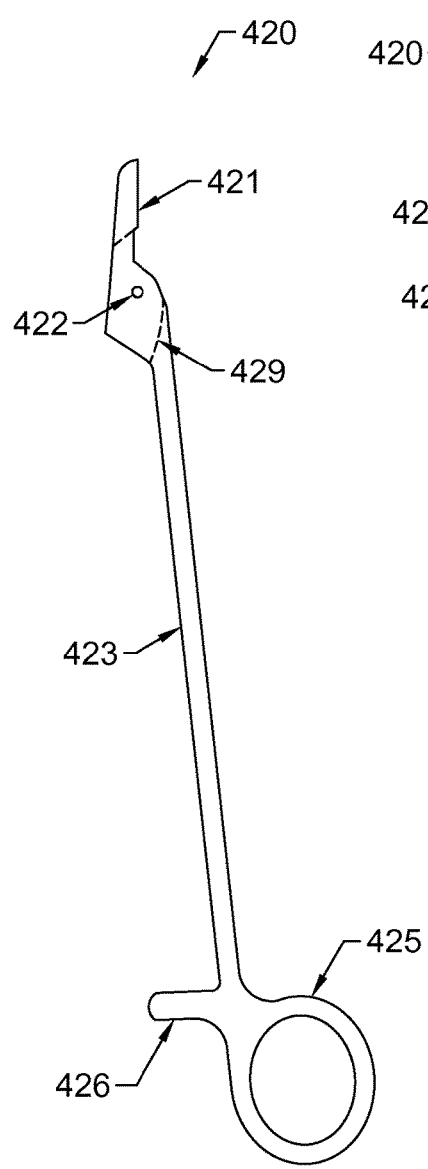
FIG. 100 shows a front view of the fifth embodiment standard grasping limb.

Operation of this embodiment is preferably as follows. In its normal configuration, the device is operated in the standard fashion as a needle holder for grasping needles and advancing them through tissue as well as grasping suture for tying surgical knots. (FIG. 96) The operator opens and closes the jaws with the use of the proximal rings 425, 435 and as desired may latch the jaws shut by advancing the rings together causing the ratcheting teeth 426, 436 to engage. The locking teeth are disengaged by applying a perpendicular force to the rings. When cutting function is desired, the operator then depresses the finger activation area 461 on the trigger mechanism, causing it to rotate. (FIG. 97) The trigger housing then rotates around the convertible limb. An internal reset spring 492 is provided from the spring post 465 on the trigger housing to the spring post 434 on the convertible limb. The reset spring 492 is compressed by the action of the operator depressing the trigger. Upon rotation of the trigger mechanism, the feedback spring head 485 preferably passes over the convertible limb shaft 433 providing audible and tactile feedback to the operator for activation and deactivation of the cutting function. As the trigger housing rotates, the cutting limb 450 is advanced by way of the bearing pin 466 within the trigger housing. Advancement of the cutting limb distally then deploys the cutting blade 451 out of the convertible jaw 431 to lie within the working area. (FIG. 114) As the operator holds the trigger 460 depressed, the blade remains activated and the instrument is converted into a cutter. Importantly, the cutting action occurs within the main grasping area of the jaws. The operator can then cut material within the jaws repeatedly as desired. The cutting action is performed by holding the trigger depressed and opening and closing the limbs in a familiar fashion such as using a pair of scissors. (FIG. 98) Once cutting is complete, the operator simply releases the trigger mechanism. The reset spring 492 within the housing then expands rotating the trigger mechanism 460 back to its resting position. Correspondingly, the attached cutting limb 450 is retracted by the movement of the bearing pin 466. The cutting blade 451 is retracted and withdrawn into the convertible jaw 431 by the retraction of the cutting limb. The device is converted back to grasping function. (FIG. 96) Once deactivated and withdrawn, the blade is protected from additional cutting until reactivated. As the trigger mechanism rotates fully the feedback spring head 485 provides feedback of deactivation of the cutting function as it passes over the convertible limb shaft 433. The instrument can then be used safely for grasping actions in the same important area of the jaws that was used for cutting.

When replacement of the cutting blade is desired, the process can be quickly performed by the operator or an assistant without tools. It is desirable to provide replacement cutting blades in sterile packaging allowing replacement to take place while still within the sterile field. First, for removal, the instrument is opened allowing access to the right side of the trigger mechanism. The finger tab 482 on the retaining pin spring is forced toward the front of the instrument preferably with digital pressure. The spring flexes and allows the retaining pin 481 to slide out of its corresponding hole in the trigger housing 467 and away from the end of the cutting limb. Once the cutting limb is released by moving the retaining pin 481, it can be lifted out of the slot 468 in the trigger mechanism away from the bearing pin 466. The cutting limb 450 is then manually advanced distally causing the blade to advance into the opening of the jaws of the instrument. Once it is advanced sufficiently for the blade to clear the jaws and allow access to the cutting limb distally within the jaws, it can then be safely grasped and removed by sliding it out fully from the distal end. A sterile replacement cutting blade is opened onto the sterile field. For replacement, the proximal end of the new cutting limb is inserted into the channel 438 in the convertible jaws 431 with the bearing recess 454 facing the hinge. The cutting limb 450 is advanced proximally into the channel 438 and is guided around the hinge pin by the shape of the channel and the interior surface of the standard limb 429. The cutting limb proximal end is then fed into the distal guide 443 on the convertible limb. In order to access the guide the cutting limb preferably flexes somewhat. Digital pressure is preferably used to direct the cutting limb into the guide as it is advanced or, if needed, an additional instrument commonly present on the surgical field can be used, such as a hemostat or other grasping forceps. Once, within the cutting guide 443 the cutting limb 450 is preferably further moved proximally through the remaining guides 442, 441 and toward the trigger mechanism. As it is advanced, the cutting blade 451 is directed into its proper position within the convertible grasping jaw 431. Proximally, the retaining pin 481 is once again disengaged preferably by use of the finger tab 482. The cutting limb is then slid into place in the trigger mechanism slot 468 with the bearing recess 454 fitting over the bearing pin 466. The finger tab 482 is released and the retaining pin 481 then is forced over the cutting limb retaining surface 456 and into the hole 467 on the other side of the trigger housing slot 468. The new cutting limb and blade are now fully secured and the instrument can be closed again and utilized normally as intended.

Sixth Embodiment

It may be preferable for the combination cutting and grasping needle holder to incorporate a blade within the hinge area near the jaws which slides into position to provide cutting in the grasping area of the jaws. This additional embodiment is described as follows: The device is constructed with two grasping jaws distally connected by a main hinge. (FIG. 117) The proximal limbs are preferably used by the operator in a standard fashion to open and close the grasping jaws. As desired, finger rings 525, 535 and ratcheting locking teeth 526, 536 are provided. The cutting blade 551 is preferably located on the end of the cutting limb 550 and preferably situated within the jaws near the main hinge 590 of the device. The cutting limb 550 preferably lies adjacent to the convertible limb 530 distally and then narrows and passes into the jaw hinge area alongside a narrowed flange 541 on the convertible limb preferably outfitted with a slot 542 to guide the cutting blade into position. When the cutting limb is not activated it preferably lies within the hinge mechanism situated between the sides of the standard limb 527. The cutting blade 551 is situated clear of the grasping jaws 521, 531 when deactivated. The distal aspect of the guide flange 541 is preferably situated at the proximal extent of the grasping area and covers the distal end of the blade 551 and prevents material from contact with the blade while the device is in normal grasping use. The cutting blade preferably incorporates a bearing surface 552 and a stabilizing fin 556. For activation of the cutting mechanism, the device is preferably opened in a standard fashion with the proximal limbs. The jaws are opened far enough for the distal surface of the slot for the convertible limb on the standard limb 529 to clear the cutting blade 551. Once sufficiently open, the cutting limb 550 is preferably advanced introducing the cutting blade into the working area of the jaws. Distal motion of the cutting limb guide post 555 is preferably directed by the guide slot 542. The cutting blade guide fin 556 preferably protrudes into the guide channel in the convertible jaw 538. The cutting blade fin and similarly the guide channel are preferably configured with a distal recess which aids in directing the distal portion of the cutting blade into a firmly seated position. Once firmly seated, the bearing surface of the blade 552 rests against the grasping surface of the convertible jaw 531. The cutting blade 551 is preferably angled so that when the standard grasping jaw 521 is closed against it to perform cutting the two surfaces are parallel. Activation of the cutting limb in this embodiment is preferably performed with the use of a sliding trigger mechanism 560 although, if desired, it could be outfitted with a trigger similar to the previous embodiment. The trigger mechanism is preferably incorporated around the proximal end of the cutting limb 550 which lies against the border of the convertible limb 530. It is further preferably attached to the convertible limb by a sliding pin 562 in a guide slot 534. The trigger mechanism preferably incorporates a finger activation area 561 on the front, back and side. The body of the trigger mechanism 563 is preferably formed around in the convertible limb shaft 533 in a clevis fashion preferably attached with the sliding pin 562 and a more distal spring loaded retaining pin 571. The mechanism preferably slides proximally and distally guided by the slot 534 and the two pins 562, 571 causing corresponding movement of the cutting limb 550 via its attachment in the bearing recess 564. A reset spring 580 is preferably provided in the guide slot 534 situated on a spring post 539 distally and resting against the sliding pin 562 proximally. The reset spring preferably is compressed with activation of the trigger mechanism and cutting blade and is held compressed while cutting is performed. Once pressure is released from the mechanism the reset spring will force the sliding pin 562 and trigger mechanism 560 proximally, deactivating the cutting blade 551. It may be desirable to exchange the cutting limb for a shaper blade. This is preferably accomplished by manually disengaging the retaining pin 571 with digital pressure on the tab 572. Once the pin is released from the housing, it can then be rotated over the convertible limb, lifting the bearing recess 564 off of the cutting limb bearing peg 554. The cutting limb is then disconnected and can be slid distally. Rotation of the trigger mechanism is limited by the opening stop surface 566 which abuts the convertible limb shaft 533. It is preferably arranged so that rotation of the trigger housing is limited such the retaining pin 571 is prevented from engaging on the outside of the convertible limb shaft 533.

Figure 119:
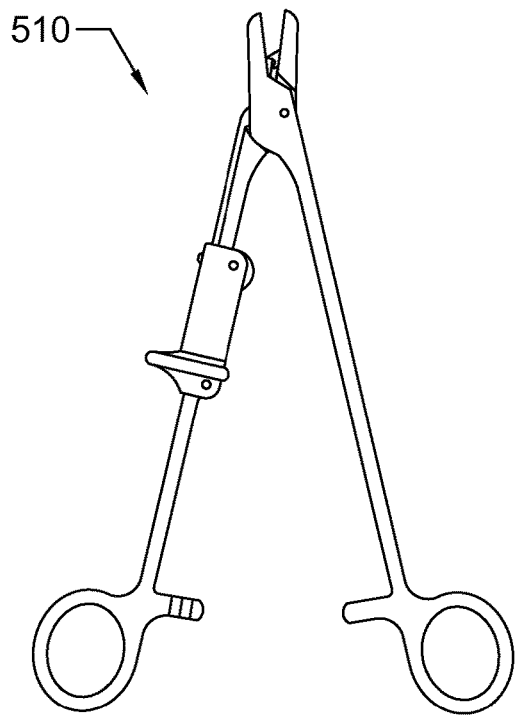
Figure 120:
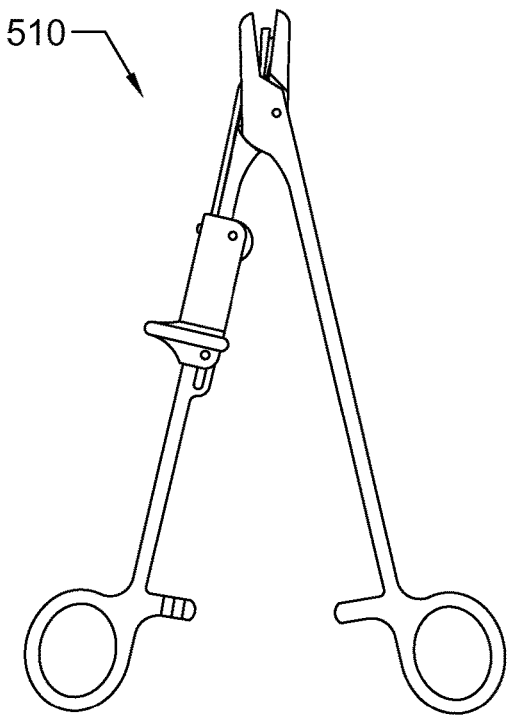
Figure 121:
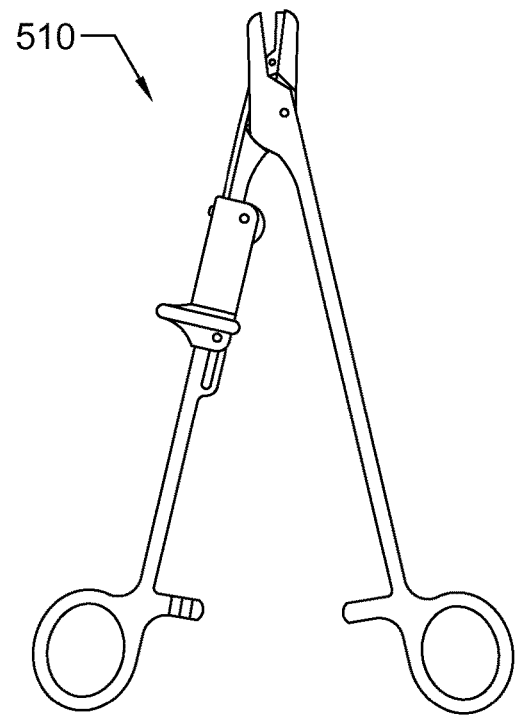
Figure 122:
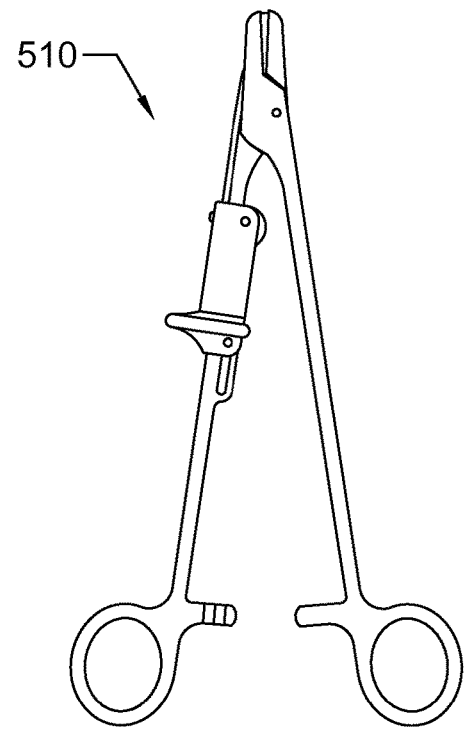
Figure 123:
Figure 124:
Figure 125:
Figures 126, 127, 128:
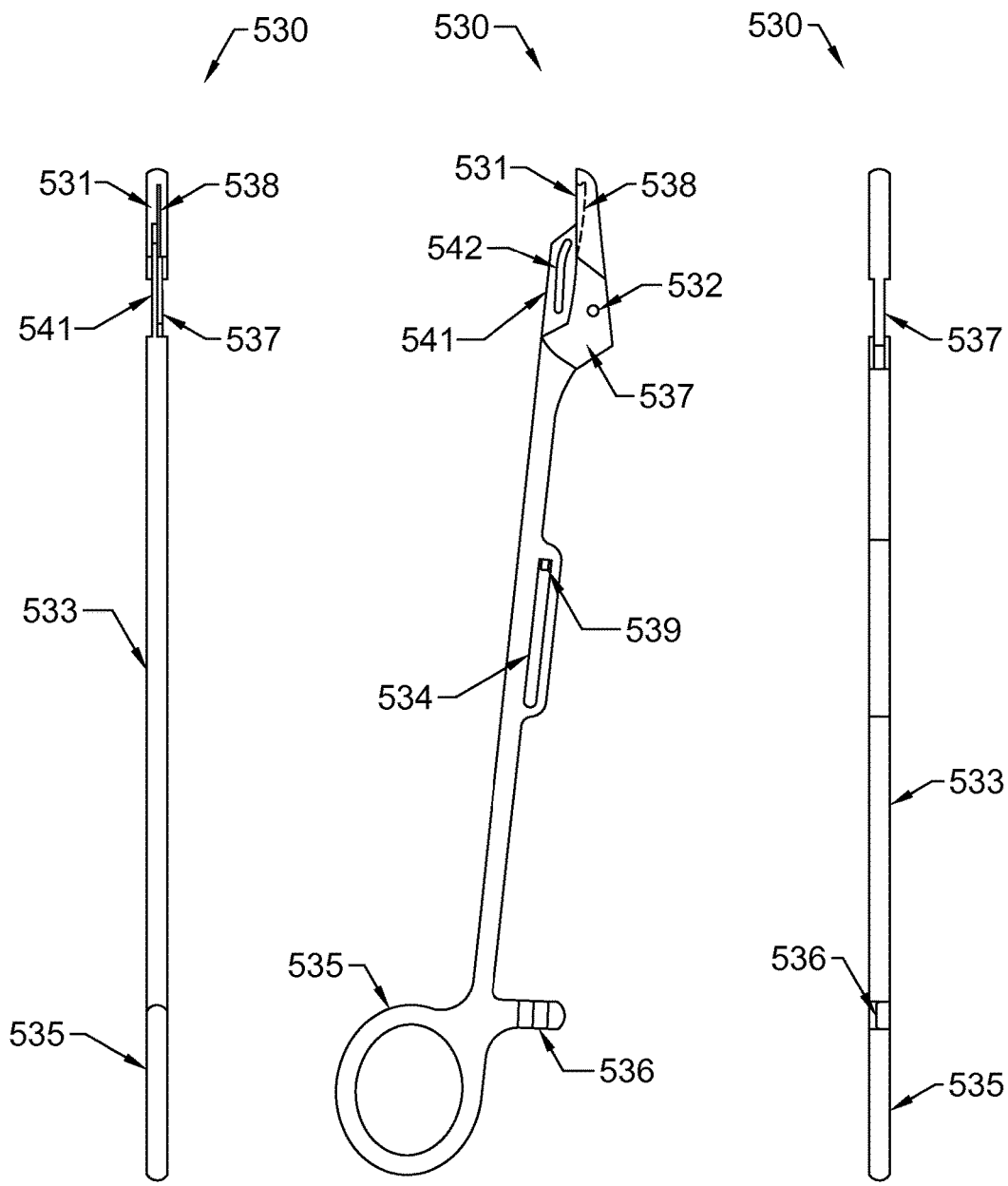

Operation of this embodiment is preferably as follows. In its normal configuration, the device is operated in the standard fashion as a needle holder for activities such as grasping needles and advancing them through tissue as well as grasping suture for tying surgical knots. (FIG. 119) The operator opens and closes the jaws with the use of the proximal finger rings 525, 535 and as desired may latch the jaws shut by advancing the rings together causing the ratcheting teeth 526, 536 to engage. The locking teeth are typically disengaged by applying a perpendicular force to the rings. When cutting function is desired, the jaws are opened somewhat for delivery of the cutting blade 551 and the operator then presses the finger activation area 561 on the trigger mechanism, forcing it distally. (FIG. 120) The cutting limb 550 is forced distally and similarly the cutting blade 551 is introduced into the grasping jaws. It is preferably guided into position by the guide flange 541, cutting blade post 555 in the guide slot 542, and the cutting blade fin 556 in the corresponding guide channel 538. Once the cutting blade is fully seated, the bearing surface 552 rests against the convertible jaw grasping surface 531. This preferably allows for stability to resist the necessary forces of cutting actions. As the operator holds the trigger mechanism 560 distally, the blade remains activated and the instrument is converted into a cutter. (FIG. 121) Importantly, the cutting action occurs within the main grasping area of the jaws. The operator can then cut material within the jaws repeatedly as desired. The cutting action is performed by holding the trigger 560 distally and opening and closing the limbs in a familiar fashion such as using a pair of scissors. (FIG. 122) Once cutting is complete, the operator simply opens the main jaws somewhat and releases pressure on the trigger mechanism. The reset spring 580 within the guide slot 534 then expands forcing the sliding pin 562 and the trigger mechanism back to its resting position. Correspondingly, the attached cutting limb 550 is retracted by its attachment in the bearing recess 564. The cutting blade 551 is retracted back into its resting position near the main hinge 590, guided by the post 555 in the guide slot 542. Once the blade is withdrawn safely alongside the guide flange 541 and out of the grasping jaws, they can be closed again. The device is converted back to grasping function. (FIG. 119) The instrument can then be used safely for grasping actions in the same important area of the jaws that was used for cutting. The cutting blade is protected from cutting material while it is deactivated.

When replacement of the cutting blade is desired, the process can be quickly performed by the operator or an assistant without tools. It is desirable to provide replacement cutting blades in sterile packaging allowing replacement to take place while still within the sterile field. First, for removal, the instrument is fully opened allowing access to the right side of the trigger mechanism. (FIG. 138) The finger tab 572 on the retaining pin spring is forced toward the back of the instrument preferably with digital pressure. The spring flexes and allows the retaining pin 571 to slide out of its corresponding hole 565 in the trigger housing and away from the convertible limb shaft 533. Once the retaining pin 571 is cleared over the convertible limb shaft 533, the trigger housing can be rotated away from the convertible limb lifting the bearing recess 564 off of the bearing peg 554 on the cutting limb. The cutting limb 550 is then disconnected and can be slid distally manually. The cutting limb and attached blade are then preferably arranged with the post 555 in the distal half of the guide slot 542. With the jaws fully open the post 555 can be disengaged by preferably applying pressure towards the front of the instrument, flexing the cutting blade and limb somewhat to clear the post from the guide slot 542. Once the post is disengaged the cutting limb and blade are preferably withdrawn distally and removed. A sterile replacement cutting blade is opened onto the sterile field. For replacement, the proximal end of the new cutting limb is inserted into the slot in the standard limb with the jaws open. It is advanced proximally bringing the cutting blade guide post 555 up to the guide flange 541. The blade is then preferably flexed slightly to allow the guide post 555 to clear the flange and insert into the guide slot 542. The cutting limb and blade are then slid proximally, fully retracting the blade. The trigger housing is then rotated back onto the bearing peg 554 of the cutting limb securing it in the recess 564. The retaining pin 571 then springs back into position against the convertible limb shaft 533. The new cutting limb and blade are now fully secured and the instrument can be closed again and utilized normally as intended.

Seventh Embodiment

The next embodiment 610 of this invention describes an application of the invention similar in function to the first embodiment 10 however with a simplified design. This embodiment may be preferable for disposable instrument fabrication for simplicity and economy. Similar to the others, this embodiment depicts the invention on a standard set of needle holders (or needle drivers.) (FIG. 140) The apparatus consists of a pair of grasping jaws 21, 631 connected by a hinge 50 near the jaws. The proximal ends of the standard 20 and convertible grasping 630 limbs are presented for use by the operator to open and close the grasping jaws of the device. (FIG. 142) Finger rings 25, 635 and ratcheting locking teeth 26, 636 are preferably provided on the proximal ends of the limbs. Separating and opposing the proximal limbs activates the jaws, strongly opening and closing them. Similarly, this embodiment of the invention employs a cutting device 641 adjacent to the jaws of the instrument. This embodiment preferably employs a one piece cutting limb 640 with a curved shaft proximally which incorporates a return spring and feedback mechanism. (FIG. 150) This cutting limb 640 may be attached to and rotate about the main hinge 50 of the device or may be connected about a different axis and or plane of action. The distal aspect of the cutting limb 640 is preferably formed as in the first embodiment 10. However, proximally the cutting limb shaft preferably bows outward 644 in the same general direction as the finger ring. The cutting limb then curves back around distally parallel to the shaft of the convertible cutting limb and then proceeds to lie on the inner side of the convertible limb facing the standard grasping limb 646. Finally the cutting limb preferably terminates in a clevis shape 647 with the opening facing the front of the device allowing it to grasp onto the convertible limb shaft 633. The left side of the clevis 647 has an extension 648 which protrudes out toward the front of the device limiting movement of the distal shaft 643. Additionally the cutting limb preferably incorporates a small bend toward the rear 645 near its proximal turn which upon activation of the cutting limb then passes over the shaft of the convertible limb 633. Operation of this embodiment 610 is similar to that of the first embodiment 10 in that the device can be used in a standard fashion as a pair of needle holders by the operator opening and closing the grasping limbs and jaws in the usual fashion. (FIG. 142) When cutting function is desired the instrument is quickly converted into a cutting device. (FIG. 143) The operator preferably depresses the bowed portion of the cutting limb shaft 644 in a similar fashion to the activation tab 44 of the first embodiment 10. It is suggested that this will be performed with the index finger of the operator as the thumb and ring finger are typically placed in the "finger rings." Pressing the cutting limb 644 preferably causes it to rotate about the hinge 50 moving the cutting shear 641 into an activated position distally. As the cutting limb 640 rotates, the terminal end of the shaft 646 (connected to the convertible limb 633 by the clevis 647) then preferably flexes in a spring like fashion. Additionally the bent portion of the proximal end of the cutting limb 645 preferably passes over the convertible limb shaft 633 providing tactile and/or audible feedback of activation of the cutting shear 641. Once the operator has depressed the cutting limb shaft 644 and activated the cutting shear 641 the device can be repeatedly used as a cutting instrument. (FIG. 144) Repeat cutting is performed by the operator preferably holding down the cutting limb 644 and opening and closing the proximal limbs similar to a pair of scissors, with the cutting function taking place in the same main operating area near the end of the instrument as was used for grasping. Once cutting function is no longer desired the operator can simply release the pressure on the cutting limb 644. Automatic and safe return of the device to a grasping function is preferably accomplished by the terminal end of the cutting limb 646 which flexed in a spring like fashion. Upon release of pressure on the cutting limb 644, the terminal end 646 functions as a return spring and forces the cutting limb 640, and therefore the cutting shear 641, to rotate back into its resting position. Finally, as the cutting shear 641 is rotated back to its inactive position the bent end of the cutting limb shaft 645 preferably passes over the shaft of the convertible limb 633 providing tactile and/or audible feedback that the device is safely reset back to a grasping function. (FIG. 142) Importantly, once deactivated by rotating the shear 641 into its resting position, it is inherently protected from cutting or damaging other material by resting the shear against the side of the convertible jaw 631. The extension 648 on the left side of the clevis 647 preferably protrudes out past the convertible limb shaft 633 and prevents further rotation of the cutting limb shaft 643. This rotation limit assures that the shear 641 does not open too far preventing unwanted exposure of the shear on the outside of the convertible jaw

631. The instrument 610 can then be used in its usual fashion operating repeatedly as a grasper, including locking until such time as cutting is once more desired. The cutting mechanism can then be reapplied when desired in the same fashion.

PARTS LIST

The following is a list of parts and materials suitable for use in the present invention:

| Item | Description | Preferred Material |
|---|---|---|
| 10 | First embodiment combined needle holder with cutting mechanism | Stainless steel |
| 20 | Standard grasping limb, first, second and seventh embodiments | Stainless steel |
| 21 | Grasping surface | Tungsten carbide |
| 22 | Hinge pin hole | |
| 23 | Standard limb shaft | |
| 25 | Finger ring | |
| 26 | Latching teeth | |
| 27 | Recess area for convertible limb | |
| 30 | Convertible grasping limb | Stainless steel |
| 31 | Grasping surface | Tungsten carbide |
| 32 | Hinge pin hole | |
| 33 | Convertible limb shaft | |
| 34 | Spring post | |
| 35 | Finger ring | |
| 36 | Latching teeth | |
| 37 | Slot for standard limb | |
| 40 | Cutting limb | Stainless steel |
| 41 | Cutting shear edge | |
| 42 | Hinge pin hole | |
| 43 | Cutting limb shaft | |
| 44 | Activation tab | |
| 45 | Retaining pin | |
| 46 | Spring post | |
| 47 | Hole for feedback leaf spring head | |
| 48 | Hole for leaf spring screw | |
| 50 | Hinge pin | Stainless steel |
| 60 | Feedback leaf spring | Stainless Spring |
| 61 | Feedback leaf spring head | |
| 62 | Feedback leaf spring screw hole | |
| 63 | Feedback leaf spring body | |
| 64 | Leaf spring attachment screw | Stainless steel |
| 70 | Reset spring | Stainless Spring |
| 110 | Second embodiment combined needle holder with cutting mechanism featuring trigger activation | Stainless steel |
| 130 | Convertible grasping limb | Stainless steel |
| 131 | Grasping surface | Tungsten carbide |
| 132 | Hinge pin hole | |
| 133 | Convertible limb shaft | |
| 134 | Spring post | |
| 135 | Finger ring | |
| 136 | Latching teeth | |
| 137 | Slot for standard limb | |
| 138 | Trigger hinge pin hole | |
| 140 | Cutting limb | Stainless steel |
| 141 | Cutting shear edge | |
| 142 | Hinge pin hole | |
| 143 | Cutting limb shaft | |
| 144 | Bearing slot | |
| 160 | Trigger mechanism | Stainless steel |
| 161 | Trigger activation area | |
| 162 | Trigger hinge pin hole | |
| 163 | Trigger body | |
| 164 | Trigger bearing pin hole | |
| 165 | Spring post | |
| 166 | Hole for feedback leaf spring head | |
| 167 | Hole for leaf spring screw | |
| 170 | Trigger hinge pin | Stainless steel |
| 180 | Trigger bearing pin | Stainless steel |
| 190 | Reset spring | Stainless spring |
| 210 | Third embodiment microsurgical type combined needle holder with cutting mechanism using slide activation | Titanium |
| 220 | Standard grasping limb, third and fourth embodiments | Titanium |
| 221 | Grasping surface | |
| 222 | Hinge pin hole | |
| 223 | Standard limb shaft | |
| 224 | Return spring | |
| 225 | Connection tab | |
| 227 | Recess area for convertible limb | |
| 230 | Convertible grasping limb | Titanium |
| 231 | Grasping surface | |
| 232 | Hinge pin hole | |
| 233 | Convertible limb shaft | |
| 234 | Return spring | |
| 235 | Connection slot | |
| 236 | Opening for slide mechanism | |
| 237 | Recess area for convertible limb | |
| 238 | Position detent | |
| 240 | Cutting limb | Titanium |
| 241 | Cutting shear edge | |
| 242 | Hinge pin hole | |
| 243 | Cutting limb shaft | |
| 244 | Bearing slot | |
| 250 | Hinge pin | Titanium |
| 260 | Slide cap | |
| 261 | Slide cap body | |
| 262 | Slide activation area | |
| 263 | Slide cap slot | |
| 264 | Slide cap screw holes | |
| 270 | Slide body | Titanium |
| 271 | Slide bearing pin | |
| 272 | Slide tab | |
| 273 | Slide fin | |
| 275 | Slide fin screw holes | |
| 276 | Recess for detent sprint | |
| 277 | Hole for detent spring screw | |
| 280 | Detent spring | Titanium |
| 281 | Detent bearing surface | |
| 282 | Detent spring screw hole | |
| 283 | Detent leaf spring shaft | |
| 310 | Fourth embodiment microsurgical type combined needle holder with cutting mechanism featuring push button activation | Titanium |
| 330 | Convertible grasping limb | Titanium |
| 331 | Grasping surface | |
| 332 | Hinge pin hole | |
| 333 | Convertible limb shaft | |
| 334 | Return spring | |
| 335 | Connection slot | |
| 336 | Slot for button mechanism | |
| 337 | Recess area for convertible limb | |
| 338 | Bypass latch screw hole | |
| 339 | Reset spring recess | |
| 340 | Cutting limb | Titanium |
| 341 | Cutting shear edge | |
| 342 | Hinge pin hole | |
| 343 | Cutting limb shaft | |
| 345 | Activation button attachment surface | |
| 346 | Screw holes | |
| 360 | Activation button | Titanium |
| 361 | Button activation surface | |
| 362 | Latch blade | |
| 363 | Activation button body | |
| 364 | Cutting limb screw holes | |
| 365 | Spring posts | |
| 368 | Attachment screws | |
| 369 | Reset spring | Stainless Spring |
| 370 | Bypass latch mechanism | Titanium |
| 371 | Bypass latch catch | |
| 372 | Bypass latch spring | |
| 373 | Bypass latch body | |
| 374 | Screw hole | |
| 410 | Fifth embodiment combined needle holder with cutting blade within grasping jaw | Stainless steel |
| 420 | Standard grasping limb | Stainless steel |

| Item | Description | Preferred Material |
|---|---|---|
| 421 | Grasping surface | Tungsten carbide |
| 422 | Hinge pin hole | |
| 423 | Standard limb shaft | |
| 425 | Finger ring | |
| 426 | Latching teeth | |
| 427 | Slot for convertible limb | |
| 428 | Cutting blade recess | |
| 429 | Cutting limb guide | |
| 430 | Convertible grasping limb | Stainless steel |
| 431 | Grasping surface | Tungsten carbide |
| 432 | Hinge pin hole | |
| 433 | Convertible limb shaft | |
| 434 | Spring post | |
| 435 | Finger ring | |
| 436 | Latching teeth | |
| 437 | Recess for standard limb | |
| 438 | Guide channel for cutting limb and blade | |
| 439 | Trigger hinge pin hole | |
| 441 | Proximal cutting limb guide | |
| 442 | Middle cutting limb guide | |
| 443 | Distal cutting limb guide | |
| 450 | Cutting limb | Stainless steel |
| 451 | Cutting blade edge | |
| 452 | Cutting limb distal bearing surface | |
| 453 | Cutting limb shaft | |
| 454 | Bearing pin recess | |
| 455 | Cutting blade fin | |
| 456 | Cutting limb retaining surface | |
| 460 | Trigger mechanism | Stainless steel |
| 461 | Trigger activation area | |
| 462 | Trigger hinge pin hole | |
| 463 | Trigger body | |
| 464 | Trigger retaining pin | |
| 465 | Spring post | |
| 466 | Bearing pin | |
| 467 | Retaining pin hole | |
| 468 | Cutting limb slot | |
| 469 | Screw hole for retaining pin and feedback spring | |
| 470 | Hole for feedback spring head | |
| 480 | Retaining pin and feedback spring | Stainless steel |
| 481 | Retaining pin | |
| 482 | Finger release tab | |
| 483 | Spring body | |
| 484 | Screw hole | |
| 485 | Feedback spring head | |
| 490 | Hinge pin | Stainless steel |
| 491 | Trigger hinge pin | |
| 492 | Reset spring | Stainless spring |
| 510 | Sixth embodiment combined needle holder with sliding blade in jaws | Stainless steel |
| 520 | Standard grasping limb | |
| 521 | Grasping surface | Tungsten carbide |
| 522 | Hinge pin hole | |
| 523 | Standard limb shaft | |
| 525 | Finger ring | |
| 526 | Latching teeth | |
| 527 | Slot for convertible limb | |
| 528 | Cutting blade recess | |
| 529 | Distal surface of slot for convertible limb | |
| 530 | Convertible grasping limb | |
| 531 | Grasping surface | Tungsten carbide |
| 532 | Hinge pin hole | |
| 533 | Convertible limb shaft | |
| 534 | Slot for trigger sliding pin | |
| 535 | Finger ring | |
| 536 | Latching teeth | |
| 537 | Recess for standard limb | |
| 538 | Guide channel for cutting blade fin | |
| 539 | Spring post | |
| 541 | Cutting limb guide flange | |
| 542 | Cutting limb post slot | |
| 550 | Cutting limb | |
| 551 | Cutting blade edge | |
| 552 | Cutting limb distal bearing surface | |
| 553 | Cutting limb shaft | |
| 554 | Bearing peg | |
| 555 | Cutting limb guide post | |
| 556 | Cutting blade stabilizing fin | |
| 557 | Cutting limb neck | |
| 560 | Trigger mechanism | |
| 561 | Trigger activation area | |
| 562 | Trigger slide pin hole | |
| 563 | Trigger body | |
| 564 | Cutting limb bearing recess | |
| 565 | Retaining pin hole | |
| 566 | Trigger mechanism opening stop surface | |
| 567 | Convertible limb slot | |
| 568 | Retaining pin spring screw hole | |
| 570 | Retaining pin spring | |
| 571 | Retaining pin | |
| 572 | Finger release tab | |
| 573 | Leaf spring | |
| 574 | Screw hole | |
| 580 | Reset spring | Stainless Spring |
| 590 | Hinge pin | |
| 610 | Seventh embodiment combined needle holder with cutting mechanism | Stainless steel |
| 630 | Convertible grasping limb | Stainless steel |
| 631 | Grasping surface | Tungsten carbide |
| 632 | Hinge pin hole | |
| 633 | Convertible limb shaft | |
| 635 | Finger ring | |
| 636 | Latching teeth | |
| 637 | Slot for standard limb | |
| 640 | Cutting limb | Stainless steel |
| 641 | Cutting shear edge | |
| 642 | Hinge pin hole | |
| 643 | Cutting limb shaft | |
| 644 | Cutting limb bowed activation area | |
| 645 | Cutting limb proximal bend | |
| 646 | Cutting limb terminal end, return spring | |
| 647 | Attachment clevis | |
| 648 | Clevis extension rotation stop | |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

I claim:

1. A surgical instrument, comprising:
    a) an instrument body having a distal end, a proximal end, a first grasping section having a grasping jaw and a second grasping section having a grasping jaw, the first and second grasping sections pivotally connected with a hinge, the instrument body configured to provide combined grasping and cutting functions;
    b) each said jaw being movable with a respective one of said sections about said hinge to enable grasping of material between the grasping jaws;
    c) a cutting member having a blade and connected to the hinge, wherein the blade is positioned next to the grasping jaws and functionally adjacent to the first grasping section;
    d) each said grasping section having a handle that enables a user to grasp the instrument body at said handles and move the grasping sections between opened and closed positions, said closed position being a grasping position that closes the jaws upon an article to be grasped;

e) wherein the cutting member and the blade are movable with the first grasping section with manipulation by the user moving the first handle;

f) a cutting blade actuator next to the handles and mounted on the first grasping section; and g) wherein the cutting of material with the blade can be done repeatedly by moving the actuator independently of said handles.

2. The surgical instrument of claim 1 further comprising one or more of the following: the handles in the form of finger rings for an operator at the proximal end of the instrument body; and/or a latch device at the proximal end to hold the instrument in a closed position.

3. The surgical instrument of claim 1, wherein each said handle is in the form of a ring, wherein the rings are angled on the proximal end.

4. The surgical instrument of claim 1 wherein the blade is moveable by an operator utilizing the actuator to convert the instrument from a grasping function into a cutting function.

5. The surgical instrument of claim 1 wherein said actuator positioned to contact and move the cutting member to said cutting position, and returns the cutting member to an inactive position when the user releases the actuator.

6. The surgical instrument of claim 1 wherein the instrument provides a tactile and/or audible "click" to an operator indicating activation and deactivation of the cutting member.

7. The surgical instrument of claim 1, wherein the instrument is formed of durable material for repeat use and sterilization for surgical procedures.

8. The surgical instrument of claim 1 wherein the instrument is formed of material suitable for single use.

9. The surgical instrument of claim 1 wherein the handle of each said grasping section has a grasping surface, said grasping surface able to be held between the user's thumb and fingers.

10. A surgical instrument, comprising:

a) an instrument body having first and second sections that are pivotally connected at a hinge, the first section having a first jaw and a first handle opposite said first jaw, the second section having a second jaw and a second handle opposite said second jaw, wherein the hinge is in between the handles and the jaws;

b) the jaws being movable with manipulation by a user moving the handles between opened and closed positions, said closed position closing the jaws to enable grasping;

c) a cutting member having a cutting member body and a blade wherein the cutting member attaches to the first section at the hinge;

d) the cutting member being movable with the first section with manipulation by the user moving the first handle;

e) wherein the blade is positioned adjacent to the jaws;

f) a cutting member actuator next to the handles and mounted on the first section, wherein movement of the actuator by the user moves the blade to a cutting position and returns the blade to a storage position; and g) wherein the actuator is movable independently of said handles.

11. The surgical instrument of claim 10 wherein the hinge is positioned closer to the jaws than the handles.

* * * * *